US012751974B2

(12) United States Patent
Tamai et al.

(10) Patent No.: US 12,751,974 B2
(45) Date of Patent: Oct. 6, 2026

(54) COMPOSITION FOR USE IN TREATING DYSTROPHIC EPIDERMOLYSIS BULLOSA

(71) Applicant: OSAKA UNIVERSITY, Osaka (JP)

(72) Inventors: Katsuto Tamai, Suita (JP); Yasushi Kikuchi, Suita (JP); Tomoki Tamakoshi, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 1321 days.

(21) Appl. No.: 17/423,285

(22) PCT Filed: Jan. 17, 2020

(86) PCT No.: PCT/JP2020/001433
§ 371 (c)(1),
(2) Date: Jul. 15, 2021

(87) PCT Pub. No.: WO2020/149395
PCT Pub. Date: Jul. 23, 2020

(65) Prior Publication Data

US 2022/0088083 A1 Mar. 24, 2022

(30) Foreign Application Priority Data

Jan. 18, 2019 (JP) ................................ 2019-007201

(51) Int. Cl.

| | |
|---|---|
| ***A61K 35/28*** | (2015.01) |
| ***A61K 9/00*** | (2006.01) |
| ***A61K 38/39*** | (2006.01) |
| ***A61P 17/00*** | (2006.01) |
| ***C07H 21/02*** | (2006.01) |
| ***C12N 15/90*** | (2006.01) |

(52) U.S. Cl.
CPC ............ *A61K 35/28* (2013.01); *A61K 9/0019* (2013.01); *A61K 38/39* (2013.01); *A61P 17/00* (2018.01); *C07H 21/02* (2013.01); *C12N 15/907* (2013.01)

(58) Field of Classification Search
CPC ................................ A61K 35/28; A61P 17/00
See application file for complete search history.

(56) References Cited

U.S. PATENT DOCUMENTS

| | | | |
|---|---|---|---|
| 5,536,656 | A | 7/1996 | Kemp et al. |
| 6,150,163 | A | 11/2000 | McPherson et al. |
| 6,682,907 | B1 | 1/2004 | Charneau et al. |
| 7,981,671 | B2 | 7/2011 | Charneau et al. |
| 8,093,042 | B2 | 1/2012 | Charneau et al. |
| 8,367,068 | B2 | 2/2013 | Charneau et al. |
| 8,460,678 | B2 | 6/2013 | Charneau et al. |
| 8,512,994 | B2 | 8/2013 | Charneau et al. |
| 8,687,359 | B2 | 4/2014 | Zhang |
| 8,697,359 | B1 | 4/2014 | Zhang |
| 8,841,126 | B2 | 9/2014 | Dodo et al. |
| 8,852,915 | B2 | 10/2014 | Chono et al. |
| 9,228,206 | B2 | 1/2016 | Dodo et al. |
| 9,393,257 | B2 | 7/2016 | Osborn et al. |
| 9,637,739 | B2 | 5/2017 | Siksnys et al. |
| 9,877,990 | B2 | 1/2018 | Krishnan et al. |
| 10,155,016 | B2 | 12/2018 | Krishnan et al. |
| 10,172,880 | B2 | 1/2019 | Osborn et al. |
| 10,266,850 | B2 | 4/2019 | Soudna et al. |
| 10,441,614 | B2 | 10/2019 | Doudna et al. |
| 11,185,564 | B2 | 11/2021 | Krishnan et al. |
| 2005/0182003 | A1 | 8/2005 | Amagai et al. |
| 2006/0040347 | A1 | 2/2006 | Charneau et al. |
| 2009/0011485 | A1 | 1/2009 | Chono et al. |
| 2009/0263900 | A1 | 10/2009 | DeKelver et al. |
| 2013/0109096 | A1 | 5/2013 | Dodo et al. |
| 2013/0326645 | A1 | 12/2013 | Cost et al. |
| 2014/0256798 | A1 | 9/2014 | Osborn et al. |
| 2014/0315294 | A1 | 10/2014 | Marceau et al. |
| 2015/0056705 | A1 | 2/2015 | Conway et al. |
| 2015/0284727 | A1 | 10/2015 | Kim et al. |
| 2016/0367588 | A1 | 12/2016 | Osborn et al. |
| 2018/0104186 | A1 | 4/2018 | Badiavas |
| 2018/0142262 | A1 | 5/2018 | Webber et al. |

(Continued)

FOREIGN PATENT DOCUMENTS

| | | |
|---|---|---|
| CN | 102695797 | 9/2012 |
| CN | 107904208 | 4/2018 |

(Continued)

OTHER PUBLICATIONS

Petrova, Anastasia, et al. "Lentiviral mediated collagen VII expression in allogeneic MSCs restores anchoring fibrils in a recessive dystrophic epidermolysis bullosa skin graft model." Molecular Therapy. vol. 26. No. 5. 50 Hampshire St, Floor 5, Cambridge, MA 02139 USA: Cell Press, 2018. (Year: 2018).*
Mamidi, Murali Krishna, et al. "Allogeneic and autologous mode of stem cell transplantation in regenerative medicine: Which way to go?." Medical hypotheses 83.6 (2014): 787-791. (Year: 2014).*
Kawachi, Masako et al. "Development of tissue-targeting hemagglutinating virus of Japan envelope vector for successful delivery of therapeutic gene to mouse skin." Human gene therapy vol. 18, 10 (2007): 881-94. (Year: 2007).*
www.fda.gov/drugs/data-standards-manual-monographs/route-administration; last accessed Apr. 14, 2026 (Year: 2026).*
Amado et al., "Anti-Human Immunodeficiency Virus Hematopoietic Progenitor Cell-Delivered Ribozyme in a Phase I Study: Myeloid and Lymphoid Reconstitution in Human Immunodeficiency Virus Type-1-infected Patients", Human Gene Therapy, vol. 15, Mar. 2004, pp. 251-262.

(Continued)

*Primary Examiner* — Robert M Kelly
*Assistant Examiner* — Allison Marie Johnson
(74) *Attorney, Agent, or Firm* — Wenderoth, Lind & Ponack, L.L.P.

(57) ABSTRACT

The present disclosure relates to a composition for use in the treatment of dystrophic epidermolysis bullosa, comprising a cell obtained from a patient with dystrophic epidermolysis bullosa, wherein the cell is a mesenchymal stem cell and genetically modified to produce type VII collagen. The present disclosure also relates to a composition for use in the treatment of dystrophic epidermolysis bullosa, comprising a cell that produces type VII collagen, wherein the composition is to be administered into a blister.

19 Claims, 6 Drawing Sheets

Specification includes a Sequence Listing.

(56) References Cited

U.S. PATENT DOCUMENTS

| | | | |
|---|---|---|---|
| 2019/0192636 A1 | 6/2019 | Dailey et al. | |
| 2019/0365929 A1 | 12/2019 | Lundberg et al. | |
| 2019/0382724 A1 | 12/2019 | Siprashvili et al. | |
| 2020/0038486 A1 | 2/2020 | Tamai et al. | |
| 2020/0206272 A1 | 7/2020 | Shimizu et al. | |
| 2021/0054376 A1 | 2/2021 | Rawlings et al. | |
| 2021/0115112 A1 | 4/2021 | Kono et al. | |
| 2021/0324420 A1 | 10/2021 | Nahada et al. | |
| 2022/0088083 A1 | 3/2022 | Tamai et al. | |
| 2022/0226438 A1* | 7/2022 | Hansson | A61K 47/28 |
| 2023/0045590 A1 | 2/2023 | Oro et al. | |

FOREIGN PATENT DOCUMENTS

| | | | |
|---|---|---|---|
| EP | 1 847 596 | 5/2012 | |
| EP | 2 589 656 | 4/2016 | |
| EP | 2 782 997 | 1/2018 | |
| EP | 2 961 262 | 7/2019 | |
| EP | 3 400 287 | 12/2020 | |
| EP | 3 851 532 | 7/2021 | |
| EP | 3 882 347 | 9/2021 | |
| JP | 5-53505 | 8/1993 | |
| JP | 7-47043 | 5/1995 | |
| JP | 2003-306448 | 10/2003 | |
| JP | 3564461 | 6/2004 | |
| JP | 2004-217587 | 8/2004 | |
| JP | 3638614 | 1/2005 | |
| JP | 3709487 | 8/2005 | |
| JP | 4436024 | 1/2010 | |
| JP | 4571306 | 8/2010 | |
| JP | 2011-518555 | 6/2011 | |
| JP | 5615321 | 9/2014 | |
| JP | 2015-516162 | 6/2015 | |
| JP | 5778147 | 7/2015 | |
| JP | 2016-512960 | 5/2016 | |
| JP | 2016-521975 | 7/2016 | |
| JP | 2016-222681 | 12/2016 | |
| JP | 6175055 | 7/2017 | |
| JP | 2017-526723 | 9/2017 | |
| JP | 6280869 | 1/2018 | |
| JP | 6343605 | 5/2018 | |
| JP | 6423338 | 10/2018 | |
| JP | 6290106 | 2/2019 | |
| JP | 6480874 | 2/2019 | |
| JP | 2019-506925 | 3/2019 | |
| JP | 2019-508454 | 3/2019 | |
| JP | 6517143 | 4/2019 | |
| JP | 2019-513689 | 5/2019 | |
| JP | 6545621 | 6/2019 | |
| JP | 2019-142819 | 8/2019 | |
| JP | 2019-235362 | 12/2019 | |
| JP | 6665088 | 2/2020 | |
| JP | 6855037 | 3/2021 | |
| JP | 6970086 | 11/2021 | |
| WO | 91/16010 | 10/1991 | |
| WO | 96/39101 | 12/1996 | |
| WO | 01/27304 | 4/2001 | |
| WO | 2009/131632 | 10/2009 | |
| WO | 2010/148050 | 12/2010 | |
| WO | 2011/140526 | 11/2011 | |
| WO | 2013/001041 | 1/2013 | |
| WO | 2013/127964 | 9/2013 | |
| WO | 2013/142578 | 9/2013 | |
| WO | 2013/169802 | 11/2013 | |
| WO | 2013/176772 | 11/2013 | |
| WO | 2014/093661 | 6/2014 | |
| WO | 2014/134412 | 9/2014 | |
| WO | 2014/186585 | 11/2014 | |
| WO | 2014/204725 | 12/2014 | |
| WO | 2015/038075 | 3/2015 | |
| WO | WO-2017035416 A2 * | 3/2017 | A61P 43/00 |
| WO | 2017/120147 | 7/2017 | |
| WO | 2017/161180 | 9/2017 | |
| WO | 2017/176336 | 10/2017 | |
| WO | WO-2017176336 A1 * | 10/2017 | A61K 35/763 |
| WO | 2018/007871 | 1/2018 | |
| WO | 2018/154413 | 8/2018 | |
| WO | WO-2018154413 A1 * | 8/2018 | A61K 35/28 |
| WO | 2018/186480 | 10/2018 | |
| WO | 2018/213502 | 11/2018 | |
| WO | 2018/235834 | 12/2018 | |
| WO | 2019/060719 | 3/2019 | |
| WO | 2019/122931 | 6/2019 | |
| WO | 2019/210042 | 10/2019 | |
| WO | 2020/100361 | 5/2020 | |
| WO | 2020/149395 | 7/2020 | |
| WO | 2021/058492 | 4/2021 | |
| WO | 6893945 | 6/2021 | |
| WO | 2022/232643 | 11/2022 | |

OTHER PUBLICATIONS

Zeng et al., "Highly branched poly(b-amino ester)s for gene delivery in hereditary skin diseases", Advanced Drug Delivery Reviews, vol. 176, (2021) 113842, pp. 1-17.

Palfi et al., "Long-term safety and tolerability of ProSavin, a lentiviral vector-based gene therapy for Parkinson's disease: a dose escalation, open-label, phase 1/2 trial", Lancet, vol. 383, Mar. 29, 2014, pp. 1138-1146.

Benjamin et al., "Genome-edited, donor-derived allogeneic anti-CD19 chimeric antigen receptor T cells in paediatric and adult B-cell acute lymphoblastic leukaemia: results of two phase 1 studies", Lancet, vol. 396, Dec. 12, 2020, pp. 1885-1894.

Fenard et al., "Infectivity enhancement of different HIV-1-based lentiviral pseudotypes in presence of the cationic amphipathic peptide LAH4-L1", Journal of Virological Methods, vol. 189, 2013, pp. 375-378.

Chou et al., "Highly branched poly(β-amino ester)s for skin gene therapy", Journal of Controlled Release, vol. 244, 2016, pp. 336-346.

Kuhl et al., "High Local Concentrations of Intradermal MSCs Restore Skin Integrity and Facilitate Wound Healing in Dystrophic Epidermolysis Bullosa", Molecular Therapy, vol. 23, No. 8, Aug. 2015, pp. 1368-1379.

Prel et al., "Highly efficient in vitro and in vivo delivery of functional RNAs using new versatile MS2-chimeric retrovirus-like particles", Molecular Therapy—Methods & Clinical Development, 2015, 15039, pp. 1-15.

Ben Fidler, "10 clinical trials to watch in the first half of 2022", 10 clinical trials to watch in the first half of 2022 | BioPharma Dive, Jan. 3, 2022, pp. 1-12.

Annual Report Pursuant to Section 13 or 15(d) of the Securities Exchange Act of 1934 For the fiscal year ended Dec. 31, 2015, Fibrocell Science, Inc., pp. 1-89.

Delivering commercial gene-therapy vector, Oxford BioMedica, hardmaneco, Mar. 31, 2017, pp. 1-52.

Ravin et al., "Lentiviral hematopoietic stem cell gene therapy for X-linked severe combined immunodeficiency", Science Translational Medicine, Apr. 20, 2016, vol. 8, Issue 335, 335ra57, pp. 1-12.

CN Cartier et al., "Hematopoietic Stem Cell Gene Therapy with a Lentiviral Vector in X-Linked Adrenoleukodystrophy", Science, Nov. 2009, vol. 326, pp. 818-824.

Joe Hughes, PhD, "Refining Platforms for Accelerated Viral Vector Production and Release", Wuxi AppTec, pp. 1-15.

Abeona Therapeutics Announces Publication of Positive Long-Term Data from Phase 1/2a Clinical Trial Evaluating EB-101 Gene Therapy for Recessive Dystrophic Epidermolysis Bullosa, Abeona Therapeutics, Oct. 15, 2019, pp. 1-4.

Pawliuk et al., "Correction of Sickle Cell Disease in Transgenic Mouse Models by Gene Therapy", Science, Dec. 2001, VolL 294, pp. 2368-2372.

Poirot et al., "Multiplex Genome-Edited T-cell Manufacturing Platform for "Off-the-Shelf" Adoptive T-cell Immunotherapies", Cancer Res, vol. 75, No. Sep. 18, 15, 2015, pp. 3853-3865.

Boro Dropulic', "Lentiviral Vectors: Their Molecular Design, Safety, and Use in Laboratory and Preclinical Research", Human Gene Therapy, Jun. 2011, pp. 649-657.

(56) References Cited

OTHER PUBLICATIONS

Enblad et al., "Phase I/IIa Trial Using CD19-Targeted Third-Generation Car T Cells for Lymphoma and Leukemia", Clin Cancer Res; vol. 24, No. 24, Dec. 15, 2018, pp. 6185-6195.
Adair et al., "Novel lineage depletion preserves autologous blood stem cells for gene therapy of Fanconi anemia complementation group A", haematologica | 2018; vol. 103, No. 11, pp. 1806-1814.
Azzouz et al., "Multicistronic Lentiviral Vector-Mediated Striatal Gene Transfer of Aromatic L-Amino Acid Decarboxylase, Tyrosine Hydroxylase, and GTP Cyclohydrolase I Induces Sustained Transgene Expression, Dopamine Production, and Functional Improvement in a Rat Model of Parkinson's Disease", The Journal of Neuroscience, Dec. 1, 2002, vol. 22, pp. 10302-10312.
Ramos et al., "Clinical and immunological responses after CD30-specific chimeric antigen receptor-redirected lymphocytes", The Journal of Clinical Investigation, vol. 127, No. 9, Sep. 2017, pp. 3461-3471.
Trading Update & Gene Therapy Agreement, Amryt Pharma Plc, Mar. 15, 2018, pp. 1-5.
Annual Report Pursuant to Section 13 or 15(d) of the Securities Exchange Act of 1934 For the fiscal year ended Dec. 31, 2020, Krystal Biotech, Inc., pp. 1-230.
Mitrophanous et al., "Stable gene transfer to the nervous system using a non-primate lentiviral vector", Gene Therapy, 1999, vol. 6, pp. 1808-1818.
Mitsuyasu et al., "Phase I/II Clinical Trials Using Gene-Modified Adult Hematopoietic StemCells for HIV: Lessons Learnt", Stem Cells International, vol. 2011, Article ID 393698, pp. 1-8.
A Follow-up Study to Evaluate the Efficacy and Safety of ALLO-ASC-DFU in ALLO-ASC-EB-101 Clinical Trial, ClinicalTrials.gov, https://clinicaltrials.gov/ct2/show/NCT03183934?term=stem+cell&cond=Epidermolysis+Bullosa&draw=3&rank=10, Jun. 12, 2017, pp. 1-6.
Richard Junghans, "T-Cell Gene Therapy to Eradicate Disseminated Breast Cancers", May 2011, pp. 1-103.
"Allogeneic ABCB5-positive Stem Cells for Treatment of Epidermolysis Bullosa", ClinicalTrials.gov, https://clinicaltrials.gov/ct2/show/NCT03529877?term=stem+cell&cond=Epid ermolysis+Bullosa &draw=3&rank=7, Oct. 14, 2020, pp. 1-9.
"Allogeneic Stem Cell Transplantation (ALLOSCT) in Recessive Dystrophic Epidermolysis Bullosa (RDEB) (RDEB)", ClinicalTrials.gov, https://clinicaltrials.gov/ct2/show/NCT00881556?term=stem+cell&cond=Epidermolysis+Bullosa&draw=3&rank=5, Feb. 15, 2012, pp. 1-7.
"Alnylam, awaiting key study data, builds case for its next rare disease drug", BioPharma Dive, https://www.biopharmadive.com/news/alnylam-vutrisiran-ttr-18-month-results/617516, Jan. 21, 2022, pp. 1-3.
Katuto Tamai, "Development of non-invasive and highly efficient mesenchymal stem cell gene therapy for severe recessive dystrophic epidermolysis bullosa", AMED Achievement report, https://amedfind.amed.go.jp/amed/search/task_search_details.html, Published online on Nov. 27, 2019, and its English translation and its English machine translation.
"Development of non-invasive and highly efficient mesenchymal stem cell gene therapy for severe recessive dystrophic epidermolysis bullosa", AMED Achievement report, https://amedfind.amed.go.jp/amed/search/task_search_details.html, Published online on Nov. 27, 2019, and its English translation and its English machine translation.
Amryt Pharma plc Annual Report 2020, Amryt Pharma, pp. 1-140.
Corporate Overview, Amryt Pharma, Sep. 2021, pp. 1-51.
Bank et al., A Phase I/II Clinical Trial of -Globin Gene Therapy for -Thalassemia, Ann. N.Y. Acad. Sci., vol. 1054, 2005, New York Academy of Sciences., pp. 308-316.
"Anti-CD 19 Chimeric Antigen Receptor T Cells for Treatment of Relapsed or Refractory Non-Hodgkin Lymphoma", ClinicalTrials.gov, https://clinicaltrials.gov/ct2/show/NCT04545762?term=NCT04545762&draw=2&rank=1, Sep. 22, 2020, pp. 1-11.
Approved Cellular and Gene Therapy Products, Approved Cellular and Gene Therapy Products | FDA, https://www.fda.govbiologics/cellular-gene-therapy-products/approved-cellular-and-gene-therapy-products, pp. 1-2.
Marinkovich et al., "Pre-Clinical Development of a Genetically-Modified Human Dermal Fibroblast (FCX-007) for the Treatment of Recessive Dystrophic Epidermolysis Bullosa", Intrexon, Fibrocell Science, pp. 1.
Dre,et al., "Global Assessment of Biological Engineering & Manufacturing", WTEC Report, Jul. 2015, pp. 1-246.
"Biochemical Correction of Severe EB by Allo HSCT and "Off-the-shelf" MSCs", ClinicalTrials.gov, https://clinicaltrials.gov/ct2/show/NCT01033552?term=stem+cell&cond=Epid ermolysis+Bullosa &draw=3&rank=9, Nov. 13, 2020, pp. 1-9.
Owaki et al., "Cell sheet engineering for regenerative medicine: Current challenges and strategies", Wiley-VCH Verlag GmbH & Co. KGaA, Weinheim, Biotechnol. J. 2014, 9, pp. 904-914.
Summary Notification Information Format for the Release of Genetically Modified Organisms Other Than Higher Plants in Accordance With Article 11 of Directive 2001/18/EC, pp. 1-19.
Shoshana Dubnow, "Boehringer Ingelheim takes next step in development of cystic fibrosis gene therapy", BioPharma Dive, https://www.biopharmadive.com/news/boehringer-ingelheim-cystic-fibrosis-gene-therapy/608488, Oct. 19, 2021, pp. 1-3.
Bonafont et al., "Clinically Relevant Correction of Recessive Dystrophic Epidermolysis Bullosa by Dual sgRNA CRISPR/Cas9-Mediated Gene Editing", Molecular Therapy vol. 27 No. 5 May 2019, pp. 986-998.
Viral Vector Manufacturing Market Global Forecast to 2023, Markets and Markets, pp. 1-27.
Peter Marinkovich, MD., "In Vivo Correction of Dystrophic Epidermolysis Bullosa by direct cutaneous COL7A1 gene replacement: results of Phase 1/2 trial", Standford Medicine, pp. 1-21.
Elizalde et al., "Lentiviral vectors: key challenges and new developments", Cell & Gene Therapy Insights 2021; 7(6), pp. 667-677.
CGMP Viral Product Development and Manufacturing, Millipore Sigma, pp. 1-2.
PrecisionX™ T7 Cas9 SmartNuclease Vector System (Tagged and Untagged) Catalog#s CAS7xxA/R/G-1 User Manual, SBI System Biosciences, pp. 1-30.
"Cell and Gene Therapy Development and Manufacturing", Miltenyi Biotec, pp. 1-8.
Naeem et al., "Latest Developed Strategies to Minimize the Off-Target Effects in CRISPR-Cas-Mediated Genome Editing", Cells 2020, 9, 1608, pp. 1-23, Published: Jul. 2, 2020.
"Viral Vector Manufacturing Overview of Capabilities", Merck, Aug. 2021, pp. 1-32.
Negre et al., "Preclinical Evaluation of Efficacy and Safety of an Improved Lentiviral Vector for the Treatment of ß-Thalassemia and Sickle Cell Disease", Bentham Science Publishers, Current Gene Therapy, 2015, 15, pp. 64-81.
Chamorro et al., "Gene Editing for the Efficient Correction of a Recurrent COL7A1 Mutation in Recessive Dystrophic Epidermolysis Bullosa Keratinocytes", Molecular Therapy-Nucleic Acids (2016) 5, e307, pp. 1-13.
Chen et al., "Restoration of type VII collagen expression and function in dystrophic epidermolysis bullosa", Nature Genetics, Published online Nov. 11, 2002, pp. 670-675.
Milone et al., "Clinical use of lentiviral vectors", Leukemia 2018, pp. 1-43.
BioReliance® pharma and biopharma manufacturing and testing services, Merck, pp. 1-34.
Hope Henderson: CRISPR Clinical Trials: A 2021 Update, Mar. 3, 2021, CRISPR Clinical Trials, Innovative Genomics Institute (IGI), https://innovativegenomics.org/news/crispr-clinical-trials-2021/, pp. 1-22.
Jaconb Bell, "Cystic fibrosis group partners with Moderna founder to find better, potentially curative treatments", BioPharma Dive, https://www.biopharmadive.com/news/flagship-cystic-fibrosis-foundation-partnership/609413, Nov. 3, 2021, pp. 1-4.
Mazarakis et al., "Rabies virus glycoprotein pseudotyping of lentiviral vectors enables retrograde axonal transport and access to the

(56) References Cited

OTHER PUBLICATIONS nervous system after peripheral delivery", Human Molecular Genetics, 2001, vol. 10, No. 19, pp. 2109-2121.
Rashidghamat et al., "Phase I/II open-label trial of intravenous allogeneic mesenchymal stromal cell therapy in adults with recessive dystrophic epidermolysis bullosa", J Am Acad Dermatol Aug. 2020, pp. 447-454.
Murauer et al., "Functional Correction of Type VII Collagen Expression in Dystrophic Epidermolysis Bullosa", Journal of Investigative Dermatology (2011), vol. 131, pp. 74-83.
Petrof et al., "Potential of systemic allogeneic mesenchymal stromal cell therapy for children with recessive dystrophic epidermolysis bullosa", J Invest Dermatol. Sep. 2015; 135(9), pp. 2319-2321.
Titeux et al., "SIN Retroviral Vectors Expressing COL7A1 Under Human Promoters for Ex Vivo Gene Therapy of Recessive Dystrophic Epidermolysis Bullosa", Molecular Therapy vol. 18 No. 8, Aug. 2010, pp. 1509-1518.
Osborn et al., "TALEN-based Gene Correction for Epidermolysis Bullosa", Molecular Therapy vol. 21 no. 6, Jun. 2013, pp. 1151-1159.
Ortiz-Urda et al., "Stable nonviral genetic correction of inherited human skin disease", Nature Medicine vol. 8 No. 10 Oct. 2002, pp. 1166-1170.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. Nov. 5, 2003, pp. 1021-1028.
Baldeschi et al., "Genetic correction of canine dystrophic epidermolysis bullosa mediated by retroviral vectors", Human Molecular Genetics, 2003, vol. 12, No. 15, pp. 1897-1905.
El-Darouti et al., "Treatment of dystrophic epidermolysis bullosa with bone marrow non-hematopoeitic stem cells: a randomized controlled trial, Dermatologic Therapy", vol. 29, 2016, pp. 96-100.
Woodley et al., "Intradermal Injection of Lentiviral Vectors Corrects Regenerated Human Dystrophic Epidermolysis Bullosa Skin Tissue in Vivo", Molecular Therapy vol. 10, No. 2, Aug. 2004, pp. 318-326.
Tang et al., "Third-generation CD28/4-1BB chimeric antigen receptor T cells for chemotherapy relapsed or refractory acute lymphoblastic leukaemia: a non-randomised, open-label phase I trial protocol", Tang X-Y, et al. BMJ Open 2016; 6:e013904, pp. 1-7.
Prisco et al., "HSV-1 mediated COL7A1 (KB103) delivery to keratinocytes and fibroblasts for recessive dystrophic epidermolysis bullosa (RDEB) therapy: preparations for Phase-I clinical trials", Krystal Biotech, pp. 1.
Ex Vivo Gene Therapy Clinical Trial for RDEB Using Genetically Corrected Autologous Skin Equivalent Grafts (EBGraft), ClinicalTrials.gov, https://clinicaltrials.gov/ct2/show/NCT04186650?term=vector&cond=Epidermolysis+Bullosa&draw=2&rank=1, Jan. 28, 2020, pp. 1-9.
Jackson et al., "Automated Manufacture of Autologous CD19 CAR-T Cells for Treatment of Non-hodgkin Lymphoma", Frontiers in Immunology, Aug. 2020 | vol. 11 |Article 1941, pp. 1-13.
McGrath et al., "Phase I study of lentiviral-mediated COL7A1 gene-modified autologous fibroblasts in adults with recessive dystrophic epidermolysis bullosa (RDEB)"., Lenticol-F Final Study Report: V1.0,Mar. 11, 2019, pp. 1-35.
Tomas et al., "Development and characterisation of cGMP-compliant stable packaging cell line for inducible lentiviral vector production", Oxgene, pp. 1.
Lin et al., "Scalable and high titre lentiviral vector production from cGMP compliant clonal suspension HEK 293 cell line", Oxgene, pp. 1.
Throm et al., "Efficient construction of producer cell lines for a SIN lentiviral vector for SCID-X1 gene therapy by concatemeric array transfection", Blood. May 21, 2009. 113(21): 5104-5110, pp. 1-16.
Georgiadis et al., "Lentiviral Engineered Fibroblasts Expressing Codon-Optimized COL7A1 Restore Anchoring Fibrils in RDEB", Journal of Investigative Dermatology (2016), vol. 136, pp. 284-292.
Goto et al., "Fibroblasts Show More Potential as Target Cells than Keratinocytes in COL7A1 Gene Therapy of Dystrophic Epidermolysis Bullosa", Journal of Investigative Dermatology (2006), vol. 126, pp. 766-772.
Zanta-Boussif et al., "Validation of a mutated PRE sequence allowing high and sustained transgene expression while abrogating WHV-X protein synthesis: application to the gene therapy of WAS", Gene Therapy (2009) 16, pp. 605-619.
Next Generation Therapies and related Life Sciences topics, Tohmatsu Limited., pp. 1-59.
Hainzl et al., "COL7A1 Editing via CRISPR/Cas9 in Recessive Dystrophic Epidermolysis Bullosa", Molecular Therapy vol. 25 No. 11 Nov. 2017, pp. 2573-2588.
White et al., "A Guide to Approaching Regulatory Considerations for Lentiviral-Mediated Gene Therapies", Human Gene Therapy Methods, vol. 28 No. 4, 2017 by Mary Ann Liebert, Inc., pp. 163-176.
Hirsch et al., "Regeneration of the entire human epidermis using transgenic stem cells", Nov. 16, 2017, vol. 551, Nature, pp. 327-346.
Campochiaro et al., "Lentiviral Vector Gene Transfer of Endostatin/Angiostatin for Macular Degeneration (GEM) Study", Human Gene Therapy, vol. 28 No. 1, 2017 by Mary Ann Liebert, Inc., pp. 99-111.
Friedman et al., "Effective Targeting of Multiple B-Cell Maturation Antigen-Expressing Hematological Malignances by Anti-B-Cell Maturation Antigen Chimeric Antigen Receptor T Cells", Human Gene Therapy, vol. 29 No. 5, 2018 by Mary Ann Liebert, Inc., pp. 585-601.
Parket et al., "Test-Retest Variability of Functional and Structural Parameters in Patients with Stargardt Disease Participating in the SAR422459 Gene Therapy Trial", TVST|2016| vol. 5|No. 5|Article 10, pp. 1-11.
Assessment of clinical research involving gene therapeutics in the Netherlands, Viral vectors, Jun. 2016, pp. 1-54.
Ben Fidler, "Intellia, with first results, delivers a 'landmark' for CRISPR gene editing", BioPharma Dive, https://www.biopharmadive.com/news/intellia-crispr-gene-editing-study-ttr-amyloidosis/602292, Jun. 26, 2021, pp. 1-10.
Izmiryan et al., "Ex Vivo COL7A1 Correction for Recessive Dystrophic Epidermolysis Bullosa Using CRISPR/Cas9 and Homology-Directed Repair", Molecular Therapy: Nucleic Acids vol. Sep. 12, 2018, pp. 554-576.
A Izmiryan et al., "Meganuclease-Mediated COL7A1 Gene Correction for Recessive Dystrophic Epidermolysis Bullosa", Journal of Investigative Dermatology (2016), vol. 136, pp. 872-875.
Ramos et al., "Clinical responses with T lymphocytes targeting malignancy-associated κ light chains", The Journal of Clinical Investigation, vol. 126 No. 7 Jul. 2016, pp. 2588-2596.
Imren et al., "High-level ß-globin expression and preferred intragenic integration after lentiviral transduction of human cord blood stem cells", The Journal of Clinical Investigation, vol. 114, No. 7, Oct. 2004, pp. 953-962.
Lwin et al., "Safety and early efficacy outcomes for lentiviral fibroblast gene therapy in recessive dystrophic epidermolysis bullosa", JCI Insight 2019; 4(11): e126243, pp. 1-19, Published: Jun. 6, 2019.
Eichstadt et al., "Phase 1/2a clinical trial of gene-corrected autologous cell therapy for recessive dystrophic epidermolysis bullosa", JCI Insight 2019; 4(19): e130554, pp. 1-10.
Gene Therapy's Next Big Challenge: Manufacturing, In Vivo, Dec. 2018, pp. 1-5.
Dull et al., "A Third-Generation Lentivirus Vector with a Conditional Packaging System", Journal of Virology, Nov. 1998, pp. 8463-8471.
Kevin McFarthing, "Clinical Trial Highlights", Journal of Parkinson's Disease 9 (2019), pp. 251-264.
Krystal, The Leader in Redosable Gene Therapy for Rare Disease, KB407 for Cystic Fibrosis, Krystal Biotech, Inc., Nov. 2020, pp. 1-20.
"Analyzing the Key Companies and the Emerging Gene Therapy in the Dermatology Segment", Key Companies in the Cell and Gene Therapy for Dermatology, https://www.delveinsight.com/blog/companies-investigating-gene-therapy-in-dermatology, Oct. 22, 2021, pp. 1-10.

(56) References Cited

OTHER PUBLICATIONS

Kocher et al., "Improved Double-Nicking Strategies for COL7A1-Editing by Homologous Recombination", Molecular Therapy: Nucleic Acids vol. 18 Dec. 2019, pp. 496-516.
Kocher et al., "Predictable CRISPR/Cas9-Mediated COL7A1 Reframing for Dystrophic Epidermolysis Bullosa", Journal of Investigative Dermatology (2020), pp. 1-14.
Donald B. Kohn, M.D., "Gene Therapy for Primary Immune Deficiencies", University of California, Los Angeles, pp. 1-32.
Krystal, The Leader in Redosable Gene Therapy for Rare Disease, Krystal Biotech, Inc., Jan. 2022, pp. 1-32.
Krystal, The Leader in Redosable Gene Therapy for Rare Disease, Krystal Biotech, Inc., Oct. 2021, pp. 1-30.
Kunii et al., "Various strategies of effector accumulation to improve the efficiency of genome editing and derivative methodologies", In Vitro Cellular & Developmental Biology—Animal (2020) 56, pp. 359-366.
Kymriah : Assessment report, European Medicines Agency, Jun. 28, 2018., pp. 1-197.
Latella et al., "Correction of Recessive Dystrophic Epidermolysis Bullosa by Transposon-Mediated Integration of COL7A1 in Transplantable Patient-Derived Primary Keratinocytes", Journal of Investigative Dermatology (2017), vol. 137, pp. 836-844.
Patel et al., "Considerations for Bioreactor Process Development and Scale-Up for Transient Transfection-Based Lentivirus Production in Suspension", MilliporeSigma, pp. 1-8.
LentiBoostTM, Lentiviral Transduction Enhancer Product Manual, Sirion Biotech, pp. 1-6.
LentiBOOST® Pharma Grade Lentivirus Transduction Enhancer Solution, 200 Transductions, Mayflower Bioscience, pp. 1, Jun. 19, 2021.
LentiBOOST™, Sirion Biotech, pp. 1-7, https://www.sirion-biotech.com/technologies/enhancer/lentiboost/, Date of retrieval: Jun. 19, 2021.
Lentiviral Vector Services, Milteyi Biotec, Dec. 24, 2020, pp. 1-14.
Lentiviral Vectors: finding the good in everyone, Lentivirus Vectors Brochure Sep. 2018, pp. 1-2.
Mary Gearing, "Lentiviral Vector Uses and Overview", May 19, 2016, Addgene blog, https://blog.addgene.org/lentiviral-vector-uses-and-overview?_ga=2.199794989.2049451008.1605845064-1524189158.1605845064, pp. 1-7.
Maurizio Federico, "Lentivirus Gene Engineering Protocols", Methods in Molecular Biology, vol. 229, Humana Press Inc., pp. 1-290.
Gene Therapies: The Next Generation on Medicine, List of 88 Gene Therapies | American Gene Technologies, https://www.americangene.com/blog/the-future-of-medicine-the-88-gene-therapies-in-development/, Posted By: AGT, On: Oct. 20, 2020, pp. 1-45.
Lwin et al., "Safety and early efficacy outcomes for lentiviral fibroblast gene therapy in recessive dystrophic epidermolysis bullosa", JCI Insight. 2019;4(11):e126243, Published: Jun. 6, 2019., pp. 1-21.
MACS GMP Vectofusin®-1, Miltenyi Biotec, https://www.miltenyibiotec.com/JP-en/products/macs-gmp-vectofusin-1.html?countryRedirected=1#gref, pp. 1-2, Date of retrieval: Jun. 19, 2021.
Levine et al., "Global Manufacturing of CAR T Cell Therapy", Molecular Therapy: Methods & Clinical Development vol. Mar. 4, 2017, pp. 92-101.
Kloss et al., "Dominant-Negative TGF-b Receptor Enhances PSMA-Targeted Human CAR T Cell Proliferation And Augments Prostate Cancer Eradication", Molecular Therapy vol. 26 No. 7 Jul. 2018, pp. 1855-1866.
George Smith, "Aking the Move: Bringing Cell and Gene Therapy Development Programs to the United States", IQVIA., pp. 1-12.
Tony Hitchcock, "Manufacturing Plasmid DNA: Ensuring Adequate Supplies for Gene and Cell Therapies", Oct. 17, 2016, BioProcess InternationalBioProcess International, https://bioprocessintl.com/manufacturing/cell-therapies/manufacturing-plasmid-dna-ensuring-adequate-supplies-gene-cell-therapies/, pp. 1-15.
Mavilio et al., "Correction of junctional epidermolysis bullosa by transplantation of genetically modified epidermal stem cells", Nature Medicine vol. 12, No. 12, Dec. 2006, pp. 1397-1402, published online Nov. 19, 2006.
Finn et al., "A Single Administration of CRISPR/Cas9 Lipid Nanoparticles Achieves Robust and Persistent In Vivo Genome Editing", Cell Reports 22, Feb. 27, 2018, pp. 2227-2235.
Marinkovich et al., "Assessment of Safety in Repeat Dosing of an In Vivo Topical Gene Therapy for the Treatment of Recessive Dystrophic Epidermolysis Bullosa (RDEB) in a Phase I/II Trial", Krystal, pp. 1.
Uchida et al., "Cas9 protein delivery non-integrating lentiviral vectors for gene correction in sickle cell disease", Molecular Therapy: Methods & Clinical Development vol. 21, Jun. 2021, pp. 121-171.
Melo et al., "Somatic Correction of Junctional Epidermolysis Bullosa by a Highly Recombinogenic AAV Variant", Molecular Therapy, pp. 1-9, advance online publication Jan. 28, 2014.
Ben Fidler, "Moderna, teaming with a startup, wades further into gene editing", BioPharma Dive, https://www.biopharmadive.com/news/moderna-metagenomi-gene-editing-deal/609311, Nov. 2, 2021, pp. 1-3.
MolMed, "Leading the way in Cell & Gene therapy", Nov. 2019, pp. 1-31.
Dan shores, mRNA IP and Competitive Landscape: 2021 in Review—Part I, Update on Moderna, BioTech, and Cure Vac, https://www.ipwatchdog.com/2021/12/21/mrna-ip-competitive-landscape-2021-review-part-update-moderna-biontech-curevac/id=141032/, Dec. 21, 2021, pp. 1-14.
MSC EVs in Dystrophic Epidermolysis Bullosa, Clinical Trials.gov, https://clinicaltrials.gov/ct2/show/NCT04173650?term=stem+cell&cond=Epid ermolysis+Bullosa&draw=3&rank=12, Mar. 24, 2020, pp. 1-6.
MT2015-20: Biochemical Correction of Severe EB by Allo HSCT and Serial Donor MSCs, Clinical Trials.gov, https://clinicaltrials.gov/ct2/show/NCT02582775?term=stem+cell&cond=Epidermolysis+Bullosa&draw=3&rank=11, Apr. 2, 2020, pp. 1-15.
Milone et al., "Chimeric Receptors Containing CD137 Signal Transduction Domains Mediate Enhanced Survival of T Cells and Increased Antileukemic Efficacy In Vivo", Molecular Therapy vol. 17 No. 8, Aug. 2009, pp. 1453-1464.
Montiel-Equihua et al., "The β-Globin Locus Control Region in Combination With the EFla Short Promoter Allows Enhanced Lentiviral Vector-mediated Erythroid Gene Expression With Conserved Multilineage Activity", Molecular Therapy vol. 20 No. 7, Jul. 2012, pp. 1400-1409.
Santilli et al., "Biochemical Correction of X-CGD by a Novel Chimeric Promoter Regulating High Levels of Transgene Expression in Myeloid Cells", Molecular Therapy, vol. 19 No. 1, Jan. 2011, pp. 122-132.
Harrison et al., "Hematopoietic Stem Cell Gene Therapy for the Multisystemic Lysosomal Storage Disorder Cystinosis", Molecular Therapy vol. 21 No. 2, Feb. 2013, pp. 433-444.
Carbonaro et al., "Preclinical Demonstration of Lentiviral Vector-mediated Correction of Immunological and Metabolic Abnormalities in Models of Adenosine Deaminase Deficiency", Molecular Therapy vol. 22 No. 3, Mar. 2014, pp. 607-622.
Candotti et al., "Gene therapy for adenosine deaminase-deficient severe combined immune deficiency: clinical comparison of retroviral vectors and treatment plans", Blood, Nov. 1, 2012, vol. 120, No. 18, pp. 3635-3646.
Phase I study of lentiviral-mediated COL7A1 gene-modified autologous fibroblasts in adults with recessive dystrophic epidermolysis bullosa (RDEB)., King's College London, Lenticol-F Version 4.0, Mar. 1, 2016, pp. 1-89.
Mamcarz et al., Lentiviral Gene Therapy Combined with Low-Dose Busulfan in Infants with SCID-X1, The New England Journal of Medicine, 380, Apr. 18, 2019, pp. 1525-1534.
Raje et al., "Anti-BCMA CAR T-Cell Therapy bb2121 in Relapsed or Refractory Multiple Myeloma", The New England Journal of Medicine, 380, May 2, 2019, pp. 1726-1737.

(56) References Cited

OTHER PUBLICATIONS

Frangoul et al., "CRISPR-Cas9 Gene Editing for Sickle Cell Disease and β-Thalassemia", The New England Journal of Medicine, 384, Jan. 21, 2021, pp. 252-260.
Next Generation Prime Editing Systems Move Closer Topossible Therapeutic Applications, Broad Institute, https://www.broadinstitute.org/news/next-generation-prime-editing-systems-move-closer-possible-therapeutic-applications, Oct. 14, 2021, pp. 1-5.
DiGiusto et al., "RNA-based gene therapy for HIV with lentiviral vector-modified CD34(+) cells in patients undergoing transplantation for AIDS-related lymphoma", Sci Transl. Med. Jun. 16, 2010; 2(36), pp. 1-18.
Robbins et al., "A pilot trial using lymphocytes genetically engineered with an NY-ESO-1-reactive T cell receptor: Long term follow up and correlates with response", Clin Cancer Res. Mar. 1, 2015; 21(5), pp. 1019-1027.
Posey Jr. et al., "Engineered CAR T Cells Targeting the Cancer-Associated Tn-Glycoform of the Membrane Mucin MUC1 Control Adenocarcinoma", Immunity. Jun. 21, 2016; 44(6), pp. 1444-1454.
Eichler, M.D., et al., "Hematopoietic Stem-Cell Gene Therapy for Cerebral Adrenoleukodystrophy", N Engl. J Med. Oct. 26, 2017; 377(17), pp. 1630-1638.
Moore et al., "Clinical and immunologic evaluation of three metastatic melanoma patients treated with autologous melanoma-reactive TCR-transduced T cells", Cancer Immunol Immunother. Feb. 2018; 67(2), pp. 311-325.
Scheffel et al., "N-acetyl cysteine protects anti-melanoma cytotoxic T cells from exhaustion induced by rapid expansion via the downmodulation of Foxol in an Akt dependent manner", Cancer Immunol Immunother. Apr. 2018; 67(4), pp. 691-702.
Mamcarz et al., "Lentiviral Gene Therapy Combined with Low-Dose Busulfan in Infants with SCID-X1", N Engl. J Med. Apr. 18, 2019; 380(16), pp. 1525-1534.
Miyahara et al., "Monolayered mesenchymal stem cells repair scarred myocardium after myocardial infarction", Nature Medicine vol. 12|No. 4|Apr. 2006, pp. 459-465, published online Apr. 2, 2006.
CTL019 (tisagenlecleucel) In pediatric and young adult patients with relapsed/refractory B-cell acute lymphoblastic leukemia, U.S. Food & Drug Administration Oncologic Drugs Advisory Committee, Jul. 12, 2017, Novartis, pp. 1-148.
Frequently Asked Questions—Viral Vectors—Novasep—Oct. 2020, pp. 1-13.
Viral Vectors: finding the good in everyone, Novasep SAS., pp. 1-3.
Gillmore et al., "CRISPR-Cas9 In Vivo Gene Editing for Transthyretin Amyloidosis", The New England Journal of Medicine, vol. 385, No. 6, Aug. 5, 2021, pp. 493-502.
GEM-2 bercolagene telserpavec (B-VEC, KB103) Phase I/ II Clinical Study Update, Oct. 29, 2019, Krystal, pp. 1-30.
FCX007 Interim Data Update, Fibrocell, pp. 1-17.
Corporate Presentation, May 15, 2019, Fibrocell, pp. 1-22.
Ortiz-Urda et al., "Injection of genetically engineered fibroblasts corrects regenerated human epidermolysis bullosa skin tissue", The Journal of Clinical Investigation |Jan. 2003 | vol. 111 | No. 2, pp. 251-255.
Ortiz-Urda et al., "Sustainable correction of junctional epidermolysis bullosa via transposon-mediated nonviral gene transfer", Gene Therapy (2003) 10, pp. 1099-1104.
Yu et al., "CART cell therapy for prostate cancer: status and promise", OncoTargets and Therapy, 2019, vol. 12, pp. 391-395.
STAR-D Gene Therapy Platform, Krystal Biotech, Inc., https://www.krystalbio.com/patients-and-families/our-star-d-platform/, pp. 1-2, Date of retrieval: Jan. 16, 2022.
Our Targets B-VEC for Dystrophic Epidermolysis Bullosa, Krystal Biotech, Inc, https://www.krystalbio.com/patients-and-families/our-targets/, pp. 1-3, Date of retrieval: Jan. 16, 2022.
Ni et al., "Generation of a packaging cell line for prolonged large-scale production of high-titer HIV-1-based lentiviral vector", The Journal of Gene Medicine, J Gene Med 2005; 7, pp. 818-834, Published online Feb. 3, 2005.
The LentiVector® Gene, Therapy Company, A leader in cell and gene therapy, Jun. 2021, Oxford Biomedica, pp. 1-53.
Viral vector CDMO, Oxford Biomedica, Jul. 2021, pp. 1-18.
LentiVector® platform, The first and leading commercial lentiviral-based gene delivery system, Oxford Biomedica plc, Jun. 2019, pp. 1-2.
Delivering life-changing gene therapies to patients, Oxford Biomedica plc, Jun. 2019, pp. 1-2, pp. 1-32.
Lentiviral Production, Platform to support design, development and delivery of gene therapies, Oxgene, pp. 1-2.
Joanne Fagg, "Epidermolysis bullosa gene therapies wait in the wings", Evaluate Vantage, Apr. 28, 2021, pp. 1-3.
Perdoni et al., "Gene editing toward the use of autologous therapies in recessive dystrophic epidermolysis bullosa", Translational Research vol. 168, Feb. 2016, pp. 50-58.
Petrova et al., "Human Mesenchymal Stromal Cells Engineered to Express Collagen VII Can Restore Anchoring Fibrils in Recessive Dystrophic Epidermolysis Bullosa Skin Graft Chimeras", Journal of Investigative Dermatology (2020), vol. 140, pp. 121-131.e6, accepted manuscript published online Jul. 19, 2019.
Ned Pagliarulo, Pfizer expands into gene editing with Beam research deal, Biopharma Dive, https://www.biopharmadive.com/news/pfizer-beam-gene-base-editing-deal-mrna/616866, Jan. 10, 2022, pp. 1-4.
Phase 3, Open-label Clinical Trial of EB-101 for the Treatment of Recessive Dystrophic Epidermolysis Bullosa (RDEB), Clinical Trials.gov, https://clinicaltrials.gov/ct2/show/NCT04227106?term=EB-101&draw=2&rank=1, Jan. 13, 2020, pp. 1-7.
MACS® GMP Vectofusin®-1, MACS Miltenyi Biotec, Issued: Aug. 2019, pp. 1-2.
Li et al., "Preclinical Development and Clinical-Scale Manufacturing of HIV Gag-Specific, Lentivirus Modified CD4 T Cells for HIV Functional Cure", Molecular Therapy: Methods & Clinical Development vol. 17 Jun. 2020, pp. 1048-1060.
Humeau et al., "Efficient Lentiviral Vector-Mediated Control of HIV-1 Replication in CD4 Lymphocytes from Diverse HIV+ Infected Patients Grouped According to CD4 Count and Viral Load", Molecular Therapy vol. 9, No. 6, Jun. 2004, pp. 1-12, Available online May 7, 2004.
Schambach et al., Equal Potency of Gammaretroviral and Lentiviral SIN Vectors for Expression of 06-Methylguanine-DNA Methyltransferase in Hematopoietic Cells, Molecular Therapy, 2006, vol. 13, No. 2, pp. 391-400.
Kelly et al., "Stem Cell Collection and Gene Transfer in Fanconi Anemia," Molecular Therapy vol. 15 no. 1, 211-219 Jan. 2007, pp. 211-219.
Milone et al., "Chimeric Receptors Containing CD137 Signal Transduction Domains Mediate Enhanced Survival of T Cells and Increased Antileukemic Efficacy In Vivo", Molecular Therapy vol. 17 No. 8, 1453-1464 Aug. 2009, pp. 1453-1464.
Kimpel et al., "Survival of the Fittest: Positive Selection of CD4+ T Cells Expressing a Membrane-Bound Fusion Inhibitor Following HIV-1 Infection", PLoS One, Aug. 2010 | vol. 5 | Issue 8 | e12357, pp. 1-11.
Zallocchi et al., "EIAV-Based Retinal Gene Therapy in the shakerl Mouse Model for Usher Syndrome Type 1B: Development of UshStat", Plos One, Apr. 2014 | vol. 9 | Issue 4, pp. 1-14.
K. Mitrophanous, "Progressing Gene Therapy Products to the Clinic—a Platform Based Approach", Oxford BioMedica, Oct. 2011, pp. 1-31.
Anzalone AV et al., "Prime Editing: An immature, yet already very exciting new gene editing tool", Nature, genOway, https://www.genoway.com/commentaries/prime-editing.htm, Oct. 2019., pp. 1-3.
Stephen A Rosenberg, M.D.., Ph.D., "An Assessment of the Safety and Feasibility of Administering T-Cells Expressing an Anti-CD19 Chimeric Antigen Receptor to Patients with B-Cell Lymphoma", Abbreviated Title: Anti-CD19 CAR PBL, Aug. 23, 2018, pp. 1-94.
Chen et al., "Restoration of type VII collagen expression and function in dystrophic epidermolysis bullosa", nature genetics vol. 32 Dec. 2002, pp. 670-675.
RetroNectin reagent overview, TaKaRa, pp. 1-4.
United States Securities and Exchange Commission, Form S-1 Registration Statement Under Registration Statement, Castle Creek Biosciences, Inc. Jul. 16, 2021.

(56) References Cited

OTHER PUBLICATIONS

Milone et al., "Clinical use of lentiviral vectors", Leukemia (2018) 32, pp. 1529-1541.
Kenjo et 1., "Low immunogenicity of LNP allows repeated administrations of CRISPR-Cas9 mRNA into skeletal muscle in mice", Nature Communications, (2021) 12:7101, pp. 1-13.
Porto et al., Base editing: advances and therapeutic opportunities, Nature Reviews, vol. 19 | Dec. 2020, pp. 839-859.
Hou et al., Lipid nanoparticles for mRNA delivery, Lipid nanoparticles for mRNA delivery, Nature Reviews Materials vol. 6, (2021), pp. 1078-1094.
Anzalone et al., "Search-and-replace genome editing without double-strand breaks or donor DNA", Nature | vol. 576 | Dec. 5, 2019, pp. 149-178.
Safety and Effectiveness Study of Allogeneic Umbilical Cord Blood-derived Mesenchymal Stem Cell in Patients With RDEB, ClinicalTrials.gov, https://clinicaltrials.gov/ct2/show/NCT04520022?term=stem+cell&cond=Epidermolysis+Bullosa&draw=3&rank=1, Aug. 20, 2020, pp. 1-7.
Safety Study of Gene-modified Autologous Fibroblasts in Recessive Dystrophic Epidermolysis Bullosa, ClinicalTrials.gov, https://clinicaltrials.gov/ct2/show/NCT02493816?term=vector&cond=Epider molysis+Bullosa&draw=2&rank=5, Jul. 10, 2015, pp. 1-7.
Global Viral Vector Manufacturing Market, Mordor Intelligence, pp. 1-35.
Viral Vector Manufacturing Market—Global Forecast to 2023, Marketsandmarkets, Jun. 2018, pp. 1-13.
Ned Pagliarulo, "Sarepta reveals gene editing alliance with biotech exploring alternative delivery methods", Biopharma Dive, https://www.biopharmadive.com/news/sarepta-genedit-gene-editing-neuromuscular-deal/618083/, Feb. 1, 2022, pp. 1-3.
Stadtmauer et al., "CRISPR-engineered T cells in patients with refractory cancer", Science 367, 1001 (2020) Feb. 28, 2020, pp. 1-12.
Siprashvili et al., "Long-Term Type VII Collagen Restoration to Human Epidermolysis Bullosa Skin Tissue", Human Gene Therapy 21(Oct. 2010), pp. 1299-1310.
Siprashvili et al., "Supplementary Online Content", JAMA. doi:10.1001/jama.2016.15588, 2016 American Medical Association, pp. 1-14.
Siprashvili et al., "Safety and Wound Outcomes Following Genetically Corrected Autologous Epidermal Grafts in Patients With Recessive Dystrophic Epidermolysis Bullosa", American Medical Association, JAMA. 2016;316(17), pp. 1808-1817.
Skin biopsy, Wikipedia, https://en.wikipedia.org/wiki/Skin_biopsy, pp. 1-6, Date of retrieval: Dec. 14, 2020.
Telugunta et al., "Cell Therapy Market", Allied Market Research, Sep. 2020, pp. 1-81.
Viral Vectors and Plasmid DNA Manufacturing Market, Allied Market Research, Published—Nov. 2017,pp. 1-53.
Ortiz-Urda et al., "Stable nonviral genetic correction of inherited human skin disease", Nature Medicine vol. 8 No. 10 Oct. 2002, pp. 1166-1170, Published online: Sep. 16, 2002.
Prior Clinical Studies, 2020, Stanford Medicine, https://med.stanford.edu/dermatology/research/research/research.html#pha se-1/2a-gene-therapy-for-rdeb, pp. 1-8, Date of retrieval: Dec. 28, 2020.
Study of Immune Tolerance and Capacity for Wound Healing of Patients With Recessive Dystrophic Epidermolysis Bullosa (RDEB) (RDEB), ClinicalTrials.gov, https://clinicaltrials.gov/ct2/show/NCT01874769?term=stem+cell&cond=Epidermolysis+Bullosa&draw=3&rank=13, Dec. 18, 2013, pp. 1-8.
Study to Evaluate the Safety of ALLO-ASC-DFU in the Subjects With Dystrophic Epidermolysis Bullosa, ClinicalTrials.gov, https://clinicaltrials.gov/ct2/show/NCT02579369?term=stem+cell&cond=Epidermolysis+Bullosa&draw=3&rank=8, Jan. 4, 2017, pp. 1-6.
Takashima et al., "Efficient Gene Reframing Therapy for Recessive Dystrophic Epidermolysis Bullosa with CRISPR/Cas9", Journal of Investigative Dermatology (2019), vol. 139, pp. 1711-1721.e4, published online May 24, 2019.
Andrew R. Byrnes, Ph.D., "The chemistry, manufacturing and controls (CMC) section of a gene therapy IND", Food and Drug Administration, pp. 1-23.
Titeux et al., "SIN Retroviral Vectors Expressing COL7A1 Under Human Promoters for Ex Vivo Gene Therapy of Recessive Dystrophic Epidermolysis Bullosa", Molecular Therapy vol. 18 No. 8, Aug. 2010, pp. 1509-1518, published online May 18, 2010.
Tmunity Announces First Patient Dosed in Phase 1 Clinical Trial with CART-TnMUCI, business wire, Jan. 15, 2020, pp. 1-2.
Topical Beremagene Geperpavec (KB103) Gene Therapy to Restore Functional Collagen VII for the Treatment of Dystrophic Epidermolysis Bullosa (GEM-1), ClinicalTrials.gove, https://clinicaltrials.gov/ct2/show/NCT03536143?term=vector&cond=Epider molysis+Bullosa&draw=2&rank=2, Mar. 13, 2020, pp. 1-6.
Viral Vector Manufacturing Market, 2020 Future Market Insights, pp. 1-25.
Viral Vectors, Non-Viral Vectors and Gene Therapy Manufacturing Market (3rd Edition), 2019-2030 (Focus on AAV, Adenoviral, Lentiviral, Retroviral, Plasmid DNA and Other Vectors, 2019 Roots Analysis, pp. 1-39.
Viral Vectors, Non-Viral Vectors and Gene Therapy Manufacturing Market (3rd Edition), 2019-2030 Focus on AAV, Adenoviral, Lentiviral, Retroviral, Plasmid DNA and Other Vectors, 2019, Roots Analysis, pp. 1-53.
Patel et al., "Considerations for Bioreactor Process Development and Scale-Up for Transient Transfection-Based Lentivirus Production in Suspension", Merck KGaA, pp. 1-8.
Webber et al., "CRISPR/Cas9-based genetic correction for recessive dystrophic epidermolysis bullosa", npj Regenerative Medicine (2016) 1, 16014, pp. 1-11.
Wu et al., "Efficient in vivo gene editing using ribonucleoproteins in skin stem cells of recessive dystrophic epidermolysis bullosa mouse model", PNAS | Feb. 14, 2017 | vol. 114 | No. 7, pp. 1660-1665.
Shoshana Dubnow, "Years later, a first-of-its-kind treatment shows the power, and limits, of gene therapy", Biopharma Dive, https://www.biopharmadive.com/news/luxturna-gene-therapy-eye-leber-lca/609832, Nov. 15, 2021, pp. 1-12.
Hanawa et al., "Efficient gene transfer into rhesus repopulating hematopoietic stem cells using a simian immunodeficiency virus-based lentiviral vector system", SIV Vector-Based Hematopoietic Cell Gene Transfer, Blood, Jun. 1, 2004 vol. 103, No. 11, pp. 4062-4069.
Carpenito et al., "Control of large, established tumor xenografts with genetically retargeted human T cells containing CD28 and CD137 domains", PNAS, Mar. 3, 2009, vol. 106, No. 9, pp. 3360-3365.
Assessment report, EMA/56140/2020, European Medicines Agency, Apr. 26, 2019, pp. 1-143.
Allogeneic Hematopoietic Stem Cell Transplant For Epidermolysis Bullosa, ClinicalTrials.gov, https://clinicaltrials.gov/ct2/show/NCT00478244?term=stem+cell&cond=Epid ermolysis+Bullosa&draw=3&rank=6, Dec. 28, 2017, pp. 1-9.
Tamai, K., "Development of non-invasive and highly efficient mesenchymal stem cell gene therapy for severe recessive dystrophic epidermolysis bullosa", AMED Achievement report, https://amedfind.amed.go.jp/amed/search/task_search_details.html, Published online on Nov. 27, 2019, and its English translation.
Extended European Search Report issued Aug. 25, 2022 in European Patent Application No. 20741062.2.
Petrova, Anastasia et al., "262. Lentiviral Mediated Collagen VII Expression in Allogeneic MSCS Restores Anchoring Fibrils in a Recessive Dystrophic Epidermolysis Bullosa Skin Graft Model", Molecular Therapy, May 2018, vol. 26, No. 5, Suppl. 1, pp. 123-124.
Tamai, Katsuto et al., "80. Transplanted Mesenchymal Stem Cells Provide Type VII Collagen in the Skin of Recessive Dystrophic Epidermolysis Bullosa", Molecular Therapy, May 2013, vol. 21, No. Suppl. 1, pp. S32-S33.
International Search Report issued Mar. 31, 2020 in International (PCT) Application No. PCT/JP2020/001433.
International Preliminary Report on Patentability issued Jun. 16, 2021 in International (PCT) Application No. PCT/JP2020/001433.

(56) References Cited

OTHER PUBLICATIONS

Küht, Tobias et al., "High Local Concentrations of Intradermal MSCs Restore Skin Integrity and Facilitate Wound Healing in Dystrophic Epidermolysis Bullosa", Mol. Ther., 2015, vol. 23, No. 8, pp. 1368-1379.
Petrova, Anastasia et al., "Human Mesenchymal Stromal Cells Engineered to Express Collagen VII Can Restore Anchoring Fibrils in Recessive Dystrophic Epidermolysis Bullosa Skin Graft Chimeras", Journal of Investigative Dermatology, 2020, vol. 140, No. 1, pp. 1-17.
Conget, Paulette et al., "Replenishment of type VII collagen and re-epithelialization of chronically ulcerated skin after intradermal administration of allogeneic mesenchymal stromal cells in two patients with recessive dystrophic epidermolysis bullosa", Cytotherapy, 2010, vol. 12, pp. 429-431.
Office Action issued Dec. 5, 2023 in corresponding Japanese Patent Application No. 2020-566497, with English machine translation, 11 pages.
Office Action and Search Report issued Dec. 6, 2023 in corresponding Chinese Patent Application No. 202080022396.3, with English translation, 43 pages.
Abdul-Wahab, A et al., Characterization and selection of a patient cohort for a phase 1/11 study of ex vivo gene therapy for recessive dystrophic epidermolysis bullosa (GENEGRAFT). British Journal of Dermatology, 2015, vol. 173, Suppl. SI. pp. 80, BG07.
Itoh, M et al., Footprint-free gene mutation correction in induced pluripotent stem cell (iPSC) derived from recessive dystrophic epidermolysis bullosa (RDEB) using the CRISPR/Cas9 and piggyBac transposon system, Journal of Dermatological Science, 2020, vol. 98. pp. 163-172.
Fidler, Ben, "In vivo cell therapy: expanding beyond CAR-T", BioPharma Dive, Oct. 18, 2022, 7 pages.
Pagliarulo, Ned, "We have to find a way FDA seeks solutions to aid bespoke gene therapy", BioPharma Dive, Oct. 13, 2020, 3 pages.
Gretzmeier, C et al., "Systemic Collagen VII Replacement Therapy for Advanced Recessive Dystrophic Epidermolysis Bullosa", Journal of Investigative Dermatology, 2022, vol. 142, pp. 1094-1102.
Berdeja JG, et al., "Ciltacabtagene autoleucel, a B-cell maturation antigen-directed chimeric antigen receptor T-cell therapy in patients with relapsed or refractory multiple myeloma (CARTITUDE-1): a phase Ib/2 open-label study", Lancet, 2021, vol. 398, pp. 314-324.
Berdeja, JG, et al. Ciltacabtagene autoleucel, a B-cell maturation antigen-directed chimeric antigen receptor T-cell therapy in patients with relapsed or refractory multiple myeloma (CARTITUDE-1): a phase 1b/2 open-label study. Lancet, 2021; Supplemen. published online Jun. 24, 2021. http://dx.doi.org/10.1016/S0140-6736(21)00933-8. 277 pages.
Fields, RG et al., "Surface modified poly(ß amino ester)-containing nanoparticles for plasmid DNA delivery", Journal of Controlled Release, 2012, vol. 164, pp. 41-48.
Sabo, P, et al.. "Mutant allele knockout with novel CRISPR nuclease promotes myelopoiesis in ELANE neutropenia", Molecular Therapy: Methods & Clinical Development, 2022, Vo. 26, pp. 119-131.
Legend Biotech, Legend Biotech Corporate Presentation, 2022, 26 pages.
Shin, JW et al., "Allele-specific silencing of the gain-of-function mutation in Huntington's disease using CRISPR-Cas9", JCI Insight. 2022, https://doi.org/10.1172/jci.insight.141042, 32 pages.
Caruso, SM et al., "CRISPR/Cas therapeutic strategies for autosomal dominant disorders", The Journal of Clinical Investigation, 2022, 132(9):e158287. https://doi.org/10.1172/JCI158287.
Krystal Biotech, Inc., Annual Report Pursuant to Section 13 or 15(d) of the Securities Exchange Act of 1934, K.A. Romano, Feb. 28, 2022, 186 pages.
2seventy bio, Inc .. Annual Report Pursuant to Section 13 or 15(d) of the Securities Exchange Act of 1934, C. Baird, Mar. 22, 2022, 221 pages.
Krystal Biotech, "Takeaways from Fireside Chat: PH3 Deb Data Presentation at AAD Mar. 26" Cowen Equity Research, Biotechnology, Mar. 7, 2022, 8 pages.
Krystal Biotech, "KB301 aesthetic data underscores market upside of Krystal's platform", B of A Securities, Mar. 22, 2022, 5 pages.
Biotech, "KRYS (Buy, PT $137): KB301 Aesthetics Data—Beauty Is in Eye of Beholder?" Chardan Research, Mar. 22, 2022, 7 pages.
Krystal Biotech, Inc. (KRYS)."KB301 Moves Forward With Encouraging Efficacy Safety; STAR-D Platform Validation Continues", H. C. Wainwright & Co., Mar. 22, 2022, 10 pages.
Krystal Biotech, Inc. (KRYS), "KB301 Reports Modest Aesthetics Efficacy in Challenging Elderly Population", SMBC Nikko Securities America. Inc., Mar. 22, 2022, 15 pages.
Krystal Biotech, Inc. "Phase I Results of KB301 Build on Mechanistic Data Presented Last Year, Jeune to Expand Into Three Phase II Trials", William Blair, Mar. 22, 2022, 5 pages.
Marinkovich, MP et al., "GEM-3: A Phase 3 Study of Beremagene Geperpavec (B-VEC), an Investigational, Topical Gene Therapy, for the Treatment of Dystrophic Epidermolysis Bullosa (DEB)", AAD 2022_GEM-3 Presentation_03272022 Final, 12 pages.
Assessment report: Abecma, International non-proprietary name: idecabtagene vicleucel, Procedure No. EMEA/H/C/004662/0000, European Medicines Agency, Committee for Medicinal Products for Human Use (CHMP), EMA/409800/20212021, Jun. 24, 2021.
"CRISPR/Cas Nucleases Product Guide", ALDEVRON. 21-CRISPR/Cas9-1. ALDEVRON.com, 8 pages.
"Helper and Packaging Plasmids for Viral Vectors Product Guide", ALDEVRON. ALDEVRON.com, 8 pages.
"Getting Started: Readiness Planning For Manufacturing" ALDEVRON. 20-FEP-1. ALDEVRON.com, 1 page.
"Whitepaper. Gene and Cell Therapy, Planning for Manufacturing Success Early, Plasmid DNA: Beginning with the end in mind." ALDEVRON. ALDEVRON.com, 13 pages.
Amryt Pharma plc, Annual Report and Accounts for the year ended Dec. 31, 2021, Company No. 12107859. 106 pages.
Amryt Pharma. Amryt Reports Q3 2022 Financial and Operational Results, Nov. 3, 2022, 38 pages.
Amryt Pharma. Corporate Overview, Nov. 2022, 35 pages.
Pagliarulo, N., "BioMarin signals lengthier FDA review for hemophilia gene therapy" BioPharma Dive, Nov. 8, 2022, 3 pages.
Gardner, J. "Bluebird's CFO resigns as cash woes raise doubts about its future" BioPharma Dive, Mar. 7, 2022, 4 pages.
Pagliarulo, N., "BridgeBio sale of FDA voucher good news for Bluebird, other biotech sellers" BioPharma Dive< May 13, 2022, 3 pages.
Pagliarulo, N., "Bristol Myers claims success in study testing earlier CAR-T use in multiple myeloma" BioPharma Dive, Aug. 10, 2022, 3 pages.
"MRNA Synthesis with Multi-Scale Production" ALDEVRON. 22-mRNA-1. ALDEVRON.com, 4 pages.
3rd Annual CRISPR 2.0 meeting announcement brochure_15.11. 2022. 13 pages.
Danaher Corporation, 2021 Overview. 36 pages.
Dermagraft, Human fibroblast-derived dermal substitute, Directions for Use, Organagenesis Inc., 11092/009. 2015. 32 pages.
Pagliarulo, N., "Editas to cut jobs, narrow research focus in restructuring" BioPharma Dive, Jan. 9, 2023, 3 pages.
Alvardo, D., "EMA weighs new safety guidance for Novartis' gene therapy Zolgensma" BioPharma Dive, Jan. 13, 2023, 2 pages.
Rastogi, T., "End of a Patent Battle, Beginning of a Licensing Fight For CRISPR" IPWatchdog, Mar. 7, 2022, 4 pages.
Alvardo, D., Ensoma buys a startup to advance 'in vivo' cell therapy work: BioPharma Dive, Jan. 6, 2023, 2 pages.
Bell, J., "European regulators back hemophilia gene therapy" BioPharma Dive, Dec. 16, 2022, 3 pages.
FDA approves Ferring's Adstiladrin as first gene therapy for bladder cancer, Dec. 23, 2022, www.genetherapynet.com/gene-therapy-news/742-fda-approves-ferring's-adstiladrin-as-first-gene-therapy-for-bladder-cancer.html. 3 pages.
Fidler, B. "FDA clears Intellia to start US tests of 'in vivo' gene editing drug," BioPharma Dive, Mar. 2, 2023, 3 pages.
Fidler, B. "FDA lifts pause on Beam plans to test base editing cancer therapy" BioPharma Dive, Dec. 2, 2022, 3 pages.
Gardner, J., "Gene editing biotechs face new uncertainty after CRISPR patent ruling" BioPharma Dive, Mar. 2, 2022, 4 pages.

(56) References Cited

OTHER PUBLICATIONS

Padliarulo, N., "Gene therapy approval won, Bluebird takes on next challenge: selling it" BioPharma Dive, Dec. 12, 2022, 4 pages.
Padliarulo, N., "Gene therapy approvals bring validation as field closes year on high" BioPharma Dive, Dec. 6, 2022, 4 pages.
Gene Therapy: From Set-Up Scale-Up handbook, RegMedNet. RegMedNet.com, 32 pages.
Courtney, DG et al., "CRISPR/Cas9 DNA cleavage at SNP-derived PAM enables both in vitro and in vivo KRT12 mutation-specific targeting", Gene Therapy (2016) vol. 23, pp. 108-112.
Negre, O et al., "Gene Therapy of the β-Hemoglobinopathies by Lentiviral Transfer of the $\beta^{A(T87Q)}$-Giobin Gene", Human Gene Therapy. 2016. vol. 27, No. 2, pp. 148-165.
Information about licensing CRISPR systems, including for clinical use, Broad Institute. https://www.broadinstitute.org/partnerships/office-strategic-alliances-and-partnering/information-about-licensing-crispr-genome-edi. 3 pages.
Fidler, B. "Intellia presses forward with new results for pioneering CRISPR drug" BioPharma Dive, Feb. 28, 2022, 7 pages.
Advanced Therapies Investment Report 2017, Phacilitate. O.M. Ball ed. 120 pages.
Makaryan, V et al., "Elastase inhibitors as potential therapies for ELANE-associated neutropenia", Journal of Leukocyte Biology, 2017, vol. 102, pp. 1143-1151.
Tang, J. et al., RDEB Gene Transfer Clinical Protocol (IRB #: 14563), Stanford Dermatology, IND# 13708, Version Date: Oct. 5, 2015, pp. 1-38.
Juno Therapeutics, Inc., Annual Report Pursuant to Section 13 or 15(d) of the Securities Exchange Act of 1934, H.E. Bishop CEO, Mar. 1, 2018, 196 pages.
Krystal Biotech, Inc. The Leader in Redosable Gene Therapy Corporate Deck Jul. 2022, 36 pages.
Libmeldy, Usual common name: Autologous CD34+ cell encoding ARSA gene, Procedure No. EMEA/H/C/005321/0000, European Medicines Agency, Committee for Medicinal Products for Human Use (CHMP), CHMP assessment report, EMA/584450/2020, Oct. 15, 2020, 157 pages.
"Mainstreaming cell and gene therapy—Realizing its potential" BioPharma Dive, Nov. 28, 2022, 6 pages.
Padliarulo, N., "Medicaid, with planned payment pilot, girds for influx of pricey gene therapies" BioPharma Dive, Feb. 21, 2023, 5 pages.
Mianne, J. et al., "CRISPR/Cas9-mediated gene knockout and interallelic gene conversion in human induced pluripotent stem cells using non-integrative bacteriophage-chimeric retrovirus-like particles", BMC Biology, 2022, 20:8, 15 pages.
Miltenyi Biotec, CliniMACS Prodigy Platform; Mastering the complexity of cell processing, product brochure, 12 pages.
Christie, KA et al., "Mutation-Independent Allele-Specific Editing by CRISPR-Cas9, a Novel Approach to Treat Autosomal Dominant Disease", Molecular Therapy, 2020, vol. 2, No. 8, 46 pages.
Monteys, AM et al., "CRISPR/Cas9 Editing of the Mutant Huntingtin Allele In Vitro and In Vivo", Molecular Therapy, 2017, vol. 25 No. 1, 62 pages.
Bell, J., "Moderna inks another gene editing deal" BioPharma Dive, Feb. 22, 2023, 3 pages.
Shores, D, "mRNA IP 2022 Year in Review: Pioneers Clash in Major Patent litigations", IPWatchdog, Jan. 1, 2023. 7 pages.
Guide, SV et al., "Trial of Beremagene Geperpavec (B-VEC) for Dystrophic Epidermolysis Bullosa", New England Journal Medicine, 2022, vol. 387, No. 24, pp. 2211-2219.
Padliarulo, N., "Novartis sales of Zolgensma gene therapy slow as market shifts" BioPharma Dive, Oct. 25, 2022, 3 pages.
Padliarulo, N., "Orchard turns to layoffs in cutting gene therapy research" BioPharma Dive, Mar. 30, 2022, 3 pages.
Oxford Biomedica, Annual report and accounts 2020, 192 pages.
Oxford Biomedica, Saving lives through innovative cell and gene therapy services, Annual report and accounts 2021.194 pages.
Patent License Agreement, Advanced Biohealing Inc. and Smith & Nephew, Inc. Exhibit 10.28, May 25, 2006, 14 pages.
Godbout, K et al., "Delivery of RNAs to Specific Organs by Lipid Nanoparticles for Gene Therapy", Pharmaceutics, 2022, vol. 14, 21 pages.
Eaglstein, WH et al., "Tissue Engineering and the Development of Apligraf, a Human Skin Equivalent", Clinical Therapeutics, 1997, vol. 19, No. 5, pp. 894-905.
Plasmid DNA Manufacturing Services, Nature Technology Corporation, 2 pages.
PL VX-Puro Vector Information, PT4002-5, Catalog No. 632164, Clontech, Jul. 1, 2010, 3 pages.
Silberklang, M, "Mechanisms of Wound Healing: Studies with the Bilayered Cellular Matrix, OrCeiTM", RD Presentation, 32 pages.
Alvarado, D. "Replay reveals second gene therapy spinout, debuting new biotech Telaria" BioPharma Dive, Nov. 21, 2022, 2 pages.
Gardner, J. "Roche's hemophilia gene therapy holds steady with longer-term data" BioPharma Dive, Dec. 12, 2022, 4 pages.
Bruckner, A et al., "The challenges of living with and managing epidermolysis bullosa: insights from patients and caregivers", Orphanet Journal of Rare Diseases (2020) vol. 15, No. 1, 15 pages.
Gurevich, I et al., "In vivo topical gene therapy for recessive dystrophic epidermolysis bullosa: a Phase 1 and 2 trial", Nature Medicine, https://doi.org/10.1038/s41591-022-01737-y.
Gardner, J. "Scientists home in on cause of Duchenne gene therapy side effect" BioPharma Dive, May 17, 2022, 3 pages.
Bluebird Bio, Inc., Current Report, US Securities and Exchange Commission, J. Cole, Dec. 1, 2016.
Legend Biotech Corporation, Annual Report Pursuant to Section 13 or 15(d) of the Securities Exchange Act of 1934, US Securities and Exchange Commission, L. Macomber, Mar. 31, 2022.
Padliarulo, N., Sickle cell pipeline narrows as gene therapy developers rethink research plans, BioPharma Dive, Feb. 23, 2023, 4 pages.
"Simplify IP for your gene therapy with OTS backbones, plasmids and enzymes" BioPharma Dive, Oct. 24, 2022, 4 pages.
Padliarulo, N., "Spark CEO Marrazzo, who led company to historic gene therapy approval, to step down" BioPharma Dive, Feb. 23, 2022, 4 pages.
Wikipedia page for: Strimvelis, "Autologous CD34+ enriched cell fraction that contains CD34+ cells transduced with retroviral vector that encodes for the human ADA cDNA sequence". Feb. 8, 2023, 4 pages.
Bell, J. "The expanding world of RNA therapies" BioPharma Dive, Aug. 23, 2022, 33 pages.
Jensen, K. "Trailing rivals, Editas shares first study data for sickle cell treatment" BioPharma Dive, Dec. 7, 2022, 2 pages.
Wikipedia page for: Valoctocogene roxaparvovec, Nov. 14, 2022, 4 pages.
GMP Manufacturing Services, VectorBuilder, CDMO corporate Dec. 2023 for client, 37 pages.
Nanoplasmid Platform, Vectors, Nature Technology Corporation, 6 pages.
Nanoplasmids R6K RNA-OUT Retrofits, Vectors-Viral Vector Transposon, Nature Technology Corporation, 2 pages.
Fidler, B. "Vertex tiptoes further into Duchenne research with Tevard deal" BioPharma Dive, Feb. 28, 2023, 3 pages.
Bell, J. "Vertex, looking to broaden its gene editing abilities, asks a young biotech for help" BioPharma Dive, Aug. 24, 2021, 3 pages.
Alvarado, D. "Verve shares slide after company reveals details on FDA trial hold" BioPharma Dive, Dec. 6, 2022, 2 pages.
Fitzgerald, JB et al., "What the PTAB's CRISPR-Cas9 Decision for Broad Institute Means for Gene Editing Patent Landscape", IPWatchdog, May 20, 2022, 5 pages.
Lu, XV, "Regulatory considerations for manufacturing and testing of investigational chimeric antigen receptor (CAR) T-cell products", U.S. Food and Drug Administration, Jan. 29, 2016, 38 pages.
Amryt Pharma, Amryt Reports Q3 2022 Financial and Operational Results.
Miltenyi Biotec, Cell & Gene Therapy Services, Lentiviral Vector Intro,_ Apr. 11, 2022, 21 pages.
Study to Evaluate Safety and Efficacy of ALLO-ASC-SHEET in Subjects With Dystrophic Epidermolysis Bullosa, ClinicalTrials. gov Identifier: NCT05157958, ClinicalTrials. gov, downloaded Mar. 16, 2022.

(56) References Cited

OTHER PUBLICATIONS

Alshehri, F et al., "A comparison of minicircle vectors expressing COL7A1 under the control of human promoters for the treatment of recessive dystrophic epidermolysis bullosa", Journal of Investigative Dermatology, 2017, vol. 137, No. 10, Supp. 2, S227, Abs. 200.
Zennou et al., "HIV-1 Genome Nuclear Import Is Mediated by a Central DNA Flap", Cell, vol. 101, Apr. 14, 2000, pp. 173-185.
Skysona—Assessment report, European Medicines Agency, May 20, 2021, pp. 1-136.
Branciaroli et al., "XLenti™ Stable Cell Lines or Lentivirus Manufacturing: new development, characterisation, and future goals", Oxgene, May 2021, p. 1.
Liu et al., "Development of improved transient and stable platforms for the scalable clinical manufacture of lentiviral vectors", Oxgene, Jul. 2021, p. 1.
Gurevich et al., "Successful In Vivo COL7A1 Gene Delivery And Correction of Recessive Dystrophic Epidermolysis Bullosa (RDEB) Skin Using An Off The Shelf HSV-1 Vector (KB103)", Elsevier Science Inc. 2018: S129, Stanford School of Medicine, p. 1.
Tamai, Katsuto, "Regenerative therapy and gene therapy for epidermolysis bullosa : current status and future perspective", Journal of Clinical and Experimental Medicine, May 5, 2018, vol. 265, No. 5, pp. 463-468, with English translation.
El-Darouti, Mohammad et al., "Treatment of dystrophic epidermolysis bullosa with bone marrow non-hematopoietic stem cells: a randomized controlled trial", Dermatologic Therapy, 2016, vol. 29, pp. 96-100.
Pope et al., "A consensus approach to wound care in epidermolysis bullosa", J Am Acad Dermatol, Nov. 2012, vol. 67, No. 5, pp. 904-917.
Noor Almaani et al., "Revertant Mosaicism in Recessive Dystrophic Epidermolysis Bullosa", Journal of Investigative Dermatology, vol. 130, pp. 1937-1940, Apr. 1, 2010.
Anna M.G. Pasmooij et al., "Revertant Mosaicism Due to a Second-Site Mutation in COL7 A 1 in a Patient with Recessive Dystrophic Epidermolysis Bullosa", Journal of Investigative Dermatology, vol. 130, pp. 2407-2411, Jun. 24, 2010.
Peter C. van den Akker et al., "Natural Gene Therapy in Dystrophic Epidermolysis Bullosa", Arch. Dermatol., vol. 148, No. 2, Feb. 2012, pp. 213-216.
Dimitra Kiritsi et al., "Mechanisms of Natural Gene Therapy in Dystrophic Epidermolysis Bullosa", journal of Investigative Dermatology, vol. 134, pp. 2097-2104, Apr. 3, 2014.
UMIN-CTR, Yasuyuki Fujita, "Pivotal study about efficiency and safety of JTEC-01 made from refertant mosaicism in epidermolysis bullosa," Jan. 26, 2016, pp. 1-12.
Wakana Matsumura et al., "Cultured Epidermal: Autografts from Clinically Revertant Skin as a Potential Wound Treatment for Recessive Dystrophic Epidermolysis Bullosa", Journal of Investigative Dermatology, vol. 139, pp. 2115-2124, 2019.
"Development of a new treatment method by regenerative medicine for refractory skin diseases", Press Release May 17, 2019, Hokkaido University Hospital with its English translation.
Anja Fritsch et al., "A hypomorphic mouse model of dystrophic epidermolysis bullosa reveals mechanisms of disease and response to fibroblast therapy", The Journal of Clinical Investigation, vol. 118, No. 5, May 2008, pp. 1669-1679.
Extended European Search Report issued Dec. 5, 2025, in corresponding European Patent Application No. 23743341.2.
Non-Final Office Action mailed Aug. 10, 2026 in U.S. Appl. No. 18/017,149, pp. 1-18.
Kikuchi et al., "Gene-Modified Blister Fluid-Derived Mesenchymal Stromal Cells for Treating Recessive Dystrophic Epidermolysis Bullosa", Journal of Investigative Dermatology, vol. 143, pp. 2447-2455 (2023).
Wenzel et al., "Genetically corrected iPSCs as cell therapy for recessive dystrophic epidermolysis bullos", Science Translational Medicine, Skin Disease, vol. 6, Issue 264, pp. 1-11 (Nov. 26, 2014).

* cited by examiner

COMPOSITION FOR USE IN TREATING DYSTROPHIC EPIDERMOLYSIS BULLOSA

TECHNICAL FIELD

The present application claims priority with respect to Japanese Patent Application No. 2019-007201, which is incorporated herein by reference in its entirety.

The present disclosure relates to compositions for use in treating dystrophic epidermolysis bullosa.

SEQUENCE LISTING

A sequence listing in electronic (ASCII text file) format is filed with this application and incorporated herein by reference. The name of the ASCII text file is "Sequence_Listing_2021-1339Ar"; the file was created on Dec. 12, 2024; the size of the file is 38,585 bytes.

BACKGROUND

Epidermolysis bullosa is a disease in which adhesive structural molecules responsible for adhesion of the skin tissue are lost or disappeared, and then the epidermis peels off from the dermis and blisters or skin ulcers occur when force is applied to the skin. The disease includes simple epidermolysis bullosa, in which the epidermis is torn to form blisters, junctional epidermolysis bullosa, in which the epidermis is peeled from the basement membrane to form blisters, and dystrophic epidermolysis bullosa, in which the basement membrane is peeled from the dermis.

Dystrophic epidermolysis bullosa is the most common type of epidermolysis bullosa, accounting for about 50% of all epidermolysis bullosa. It is a hereditary disease caused by a mutation in the COL7A1 gene, which encodes type VII collagen. In the structure of the skin, the epidermal basal cells at the bottom of the epidermis are bound to a sheet-like structure called the basement membrane. Type VII collagen forms fibers called anchoring fibrils in the dermis and connects the basement membrane and the dermis. Therefore, if there is an abnormality in the type VII collagen gene, the adhesive function between the basement membrane and the dermis is impaired, resulting in dystrophic epidermolysis bullosa, in which blisters form between the basement membrane and the dermis. Among dystrophic epidermolysis bullosa, severe recessive dystrophic epidermolysis bullosa is a very serious hereditary bullous skin disease that has continued burn-like skin symptoms throughout the body immediately after birth, and cutaneous spinous cell carcinoma (scar cancer) occurs frequently from around 30 years old and leads to death.

There is currently no effective treatment for epidermolysis bullosa, and the development of gene therapy that radically suppresses blistering is required. As such gene therapy, a therapeutic technique is disclosed in which skin cells of a patient are collected, genetically engineered to produce type VII collagen, cultured to form a skin sheet, and transplanted to the patient (Patent Document 1). Also, it has been proposed to subject mesenchymal stem cells lacking the type VII collagen activity to genome editing, differentiate the mesenchymal stem cells capable of producing type VII collagen thus obtained into keratinocytes or fibroblasts, culture the cells to form a skin sheet, and use the skin sheet for treating a patient (see Patent Document 2).

CITATION LIST

Patent Documents

Patent Document 1: WO2017/120147
Patent Document 2: WO2018/154413

SUMMARY OF INVENTION

Problem to be Solved

Manufacturing the skin sheet requires advanced process control and culture technology, and then involves high-difficulty and high-cost. Therapeutic agents that are easier to manufacture are required.

Solution to Problem

In one aspect, the present disclosure relates to a composition for use in the treatment of dystrophic epidermolysis bullosa, comprising a cell obtained from a patient with dystrophic epidermolysis bullosa, wherein the cell is a mesenchymal stem cell and genetically modified to produce type VII collagen.

In another aspect, the present disclosure relates to a composition for use in the treatment of dystrophic epidermolysis bullosa, comprising a cell that produces type VII collagen, wherein the composition is to be administered into a blister.

Effect of Invention

The present disclosure provides compositions for use in treating dystrophic epidermolysis bullosa.

DESCRIPTION OF EMBODIMENTS

Figure 1:
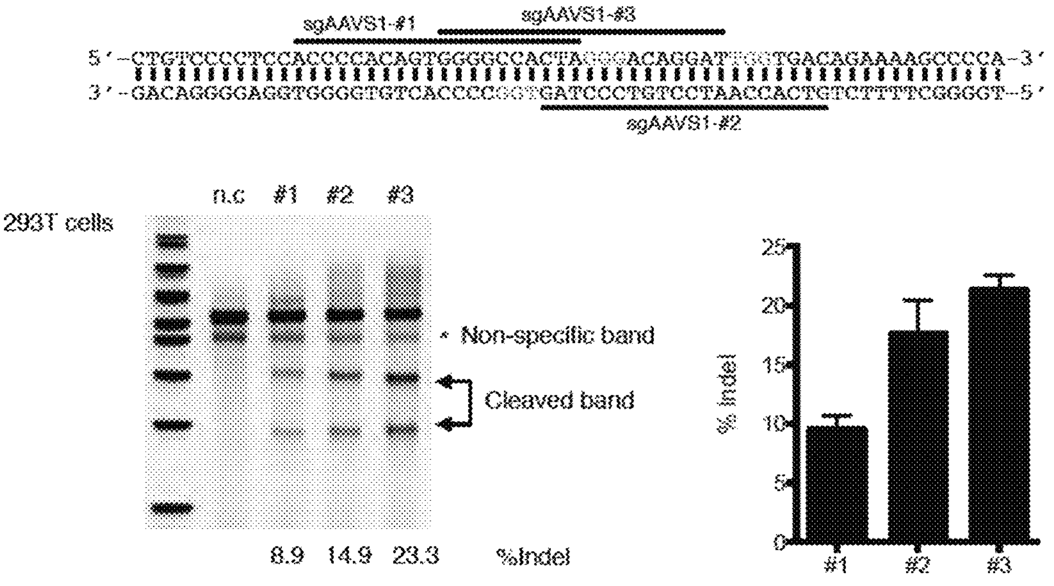
FIG. 1 shows the cleavage of genomic DNA by the designed sgRNAs (sgAAVS1-#1 to #3) and their cleavage efficiency. The top strand, SEQ ID NO: 6, and bottom strand, SEQ ID NO: 7 are shown.

Unless otherwise specified, the terms used in the present disclosure have meanings generally understood by those skilled in the art in the fields such as organic chemistry, medical science, pharmaceutical science, molecular biology, and microbiology. Definitions of some terms used in the present disclosure are provided below, and these definitions supersede the general understandings in the present disclosure.

Dystrophic epidermolysis bullosa is a hereditary disease caused by a mutation in the COL7A1 gene, which encodes type VII collagen, and is known to be characterized in that no type VII collagen is produced or type VII collagen with reduced function due to the mutation is produced. The type VII collagen forms fibers called anchoring fibrils in the dermis and connects the basement membrane and the dermis. The type VII collagen contains a first non-collagen region, a collagen region, and a second non-collagen region from the N-terminus, and forms a triple chain at the collagen region, which is characterized by a repeating sequence of glycine-X-Y. Two molecules bind to each other at the C-terminus and the N-terminus binds to the basement membrane. Examples of mutations include a mutation in which glycine in the collagen region is replaced by a different amino acid, a stop codon mutation that stops protein translation, and a splice site mutation. The mutation may be in one of the alleles or in both. Dystrophic epidermolysis bullosa includes dominant dystrophic epidermolysis bullosa and recessive dystrophic epidermolysis bullosa, and the recessive dystrophic epidermolysis bullosa include severe generalized recessive dystrophic epidermolysis bullosa and other generalized types with relatively mild symptoms. The dystrophic epidermolysis bullosa herein may be any type of dystrophic epidermolysis bullosa, and the causal mutation in the COL7A1 gene may be any mutation.

In the present disclosure, a cell that produces type VII collagen is used. As used herein, the term "cell that produces type VII collagen" means a cell that produces a functional type VII collagen (ie, a type VII collagen capable of forming anchoring fibrils). The cell that produces type VII collagen may be a cell that naturally produces type VII collagen or a cell that has been genetically modified to produce type VII collagen.

In the present disclosure, genetic modification of a cell means both modification of a gene in the genome of the cell and modification of the cell to express a gene from a nucleic acid construct outside the genome (such as a vector). That is, the expression "genetically modifying a cell to produce type VII collagen" includes modifying a cell to express type VII collagen from a COL7A1 gene in the genome, and modifying a cell to express type VII collagen from a COL7A1 gene in a nucleic acid construct outside the genome. Also, "a cell genetically modified to produce type VII collagen" includes a cell that expresses type VII collagen from a COL7A1 gene in the genome and a cell that expresses type VII collagen from a COL7A1 gene in a nucleic acid construct outside the genome.

Genetic modification of a cell can be carried out by introducing a COL7A1 gene or by correcting a mutation in the COL7A1 gene in the genome. The introduction of a COL7A1 gene can be carried out either by introducing a COL7A1 gene into the genome of the cell or by placing a nucleic acid construct comprising a COL7A1 gene in the cell so that the COL7A1 gene is expressed from the nucleic acid construct outside the genome. When a COL7A1 gene is introduced into the genome of a cell, the COL7A1 gene may be introduced at a specific site or may be introduced at random. In an embodiment, the COL7A1 gene is introduced into the COL7A1 locus of the genome, or a safe harbor such as the AAVS1 region.

The cell may be a cell obtained from a patient with dystrophic epidermolysis bullosa to which the cell is to be administered (ie, an autologous cell), or a cell obtained from a subject other than the patient (ie, an allogeneic cell). Subjects other than the patient include healthy individuals, especially HLA-matched healthy individuals, or the patient's mother. In an embodiment, the cell is a cell obtained from a patient with dystrophic epidermolysis bullosa. The cell obtained from a patient with dystrophic epidermolysis bullosa includes a cell that does not produce type VII collagen and a cell that produces type VII collagen with reduced function due to a mutation, and the "cell obtained from a patient with dystrophic epidermolysis bullosa" as used herein may be any of them.

The cell may be any cell as long as it produces type VII collagen in the vicinity of the epidermal basement membrane when administered to a patient. The cell can be a cell derived from skin, bone marrow, or blood (eg, peripheral blood). In an embodiment, the cell is a keratinocyte, skin fibroblast, or mesenchymal stem cell. In a different embodiment, the cell is an iPS cell induced from a cell obtained from a patient or a subject other than the patient or a cell induced from such an iPS cell. Thus, the cell may be a cell obtained from a patient or a subject other than the patient, or may be a cell induced from the obtained cell. When the cell is a genetically modified cell and also it is a cell induced from a cell obtained from a patient or a subject other than the patient, the genetic modification may have been carried out before or after the induction.

In the present disclosure, the term "cell" is used in the sense of including a cell after proliferation as needed. Proliferation of a cell can be carried out by culturing the cell. For example, "a cell obtained from a patient or a subject other than the patient" includes a cell collected from a patient or a subject other than the patient and then proliferated, and "a genetically modified cell" includes a cell that is proliferated from a cell obtained by genetic modification. When genetic modification is carried out, a cell may be prolifelated until the amount required for the genetic modification is obtained. Also, after genetic modification, the cell may be prolifelated until the amount required for treatment is obtained.

Keratinocytes and skin fibroblasts may be obtained by any method known in the art. For example, the epidermis and the dermis are separated by enzymatic treatment and/or mechanical treatment of the skin biopsy tissue, and each of the epidermis and the dermis thus separated is further subjected to enzymatic treatment. Keratinocytes can be obtained from the epidermis sample and skin fibroblasts can be obtained from the dermis sample.

In an embodiment, the cell is a mesenchymal stem cell. When administered to a patient, mesenchymal stem cells are considered to reside in a patient tissue longer than keratinocytes and skin fibroblasts. Also, while inflammatory reactions are expected when a genetically modified cell produces a protein that has not been produced in the patient so far, mesenchymal stem cells have an anti-inflammatory effect and thus would more advantageous than keratinocytes and skin fibroblasts.

A mesenchymal stem cell (also referred to herein as MSC) has adhesiveness to a solid phase (eg, a plastic culture vessel), and has both the self-renewal ability and the differentiation ability into mesenchymal tissues (such as bone, cartilage, fat, and muscle). In an embodiment, the mesenchymal stem cell is a cell capable of differentiating into at least one of an osteoblast, chondrocyte and adipocyte. In an embodiment, the mesenchymal stem cell is a cell capable of differentiating into an osteoblast, chondrocyte and adipocyte. When a cell population has the above-mentioned abilities, it is understood to include a mesenchymal stem cell. Mesenchymal stem cells can be obtained from bone marrow or other tissues (for example, blood, such as umbilical cord blood and peripheral blood, as well as skin, fat, and dental pulp). In an embodiment, the mesenchymal stem cell is a bone marrow-derived mesenchymal stem cell (also referred to herein as BM-MSC). The bone marrow-derived mesenchymal stem cell can be obtained from any site such as femur, vertebra, sternum, ilium, and tibia.

Mesenchymal stem cells may be obtained by any method known in the art. For example, methods based on adhesiveness, cell surface markers, and density difference can be mentioned. For example, cells obtained from bone marrow or other tissues containing mesenchymal stem cells are seeded on a plastic or glass culture vessel, and cells that adhere to the culture vessel and proliferate are collected. Alternatively, mesenchymal stem cells can also be obtained by cell sorting (such as FACS, MACS) using an antibody against a surface marker of mesenchymal stem cells. The surface marker of human mesenchymal stem cells may be one or more of the followings: PDGFRα positive, PDGERβ positive, Lin negative, CD45 negative, CD44 positive, CD90 positive, CD29 positive, Flk-negative, CD105 positive, CD73 positive, CD90 positive, CD71 positive, Stro-1 positive, CD106 positive, CD166 positive, CD31 negative, CD271 positive, and CD11b negative.

iPS cells may be produced by any method known in the art. For example, iPS cells can be produced by introducing three types of transcription factors, OCT4, SOX2, and NANOG into somatic cells such as fibroblasts obtained from a patient or a subject other than the patient (Budniatzky and Gepstein, Stem Cells Transl Med. 3 (4): 448-57, 2014; Barrett et al, Stem Cells Trans Med 3:1-6 sctm.2014-0121, 2014; Focosi et al., Blood Cancer Journal 4: e211, 2014).

As used herein, the term "cell" can mean a single cell or multiple cells, depending on the context. Further, the cell may be a cell population composed of one type of cell or a cell population including a plurality of types of cells.

As used herein, the term "COL7A1 gene" means a nucleic acid sequence encoding type VII collagen, and is used to include cDNA as well as a sequence containing one or more introns (for example, a genomic sequence or a minigene). The representative nucleic acid sequence of the human COL7A1 gene (CDNA) is shown in SEQ ID NO: 1, and the representative amino acid sequence of human type VII collagen is shown in SEQ ID NO: 2. The cDNA sequence of the COL7A1 gene is disclosed in GenBank: NM_000094.3, and the genome sequence is disclosed in GenBank: AC121252.4. The sequence of a COL7A1 gene is not limited to any specific sequence as long as it encodes a functional type VII collagen (ie, a type VII collagen capable of forming anchoring fibrils).

```
cDNA sequence of human COL7A1 gene (8835 bp)
                                    (SEQ ID NO: 1)
ATGACGCTGCGGCTTCTGGTGGCCGCGCTCTGCGCCGGGATCCTGGCAG

AGGCGCCCCGAGTGCGAGCCCAGCACAGGGAGAGAGTGACCTGCACGCG

CCTTTACGCCGCTGACATTGTGTTCTTACTGGATGGCTCCTCATCCATT

GGCCGCAGCAATTTCCGCGAGGTCCGCAGCTTTCTCGAAGGGCTGGTGC

TGCCTTTCTCTGGAGCAGCCAGTGCACAGGGTGTGCGCTTTGCCACAGT

GCAGTACAGCGATGATCCACGGACAGAGTTCGGCCTGGATGCACTTGGC

TCTGGGGGTGATGTGATCCGCGCCATCCGTGAGCTTAGCTACAAGGGGG

GCAACACTCGCACAGGGGCTGCAATTCTCCATGTGGCTGACCATGTCTT

CCTGCCCCAGCTGGCCCGACCTGGTGTCCCCAAGGTCTGCATCCTGATC

ACAGACGGGAAGTCCCAGGACCTGGTGGACACAGCTGCCCAAAGGCTGA

AGGGGCAGGGGGTCAAGCTATTTGCTGTGGGGATCAAGAATGCTGACCC

TGAGGAGCTGAAGCGAGTTGCCTCACAGCCCACCAGTGACTTCTTCTTC

TTCGTCAATGACTTCAGCATCTTGAGGACACTACTGCCCCTCGTTTCCC

GGAGAGTGTGCACGACTGCTGGTGGCGTGCCTGTGACCCGACCTCCGGA

TGACTCGACCTCTGCTCCACGAGACCTGGTGCTGTCTGAGCCAAGCAGC

CAATCCTTGAGAGTACAGTGGACAGCGGCCAGTGGCCCTGTGACTGGCT

ACAAGGTCCAGTACACTCCTCTGACGGGGCTGGGACAGCCACTGCCGAG

TGAGCGGCAGGAGGTGAACGTCCCAGCTGGTGAGACCAGTGTGCGGCTG

CGGGGTCTCCGGCCACTGACCGAGTACCAAGTGACTGTGATTGCCCTCT

ACGCCAACAGCATCGGGGAGGCTGTGAGCGGGACAGCTCGGACCACTGC

CCTAGAAGGGCCGGAACTGACCATCCAGAATACCACAGCCCACAGCCTC

CTGGTGGCCTGGCGGAGTGTGCCAGGTGCCACTGGCTACCGTGTGACAT

GGCGGGTCCTCAGTGGTGGGCCCACACAGCAGCAGGAGCTGGGCCCTGG

GCAGGGTTCAGTGTTGCTGCGTGACTTGGAGCCTGGCACGGACTATGAG

GTGACCGTGAGCACCCTATTTGGCCGCAGTGTGGGGCCCGCCACTTCCC

TGATGGCTCGCACTGACGCTTCTGTTGAGCAGACCCTGCGCCCGGTCAT

CCTGGGCCCCACATCCATCCTOCTTTCCTGGAACTTGGTGCCTGAGGCC

CGTGGCTACCGGTTGGAATGGCGGCGTGAGACTGGCTTGGAGCCACCGC

AGAAGGTGGTACTGCCCTCTGATGTGACCCGCTACCAGTTGGATGGGCT

GCAGCCGGGCACTGAGTACCGCCTCACACTCTACACTCTGCTGGAGGGC

CACGAGGTGGCCACCCCTGCAACCGTGGTTCCCACTGGACCAGAGCTGC

CTGTGAGCCCTGTAACAGACCTGCAAGCCACCGAGCTGCCCGGGCAGCG

GGTGCGAGTGTCCTGGAGCCCAGTCCCTGGTGCCACCCAGTACCGCATC
```

-continued

ATTGTGCGCAGCACCCAGGGGGTTGAGCGGACCCTGGTGCTTCCTGGGA

GTCAGACAGCATTCGACTTGGATGACGTTCAGGCTGGGCTTAGCTACAC

TGTGCGGGTGTCTGCTCGAGTGGGTCCCCGTGAGGGCAGTGCCAGTGTC

CTCACTGTCCGCCGGGAGCCGGAAACTCCACTTGCTGTTCCAGGGCTGC

GGGTTGTGGTGTCAGATGCAACGCGAGTGAGGGTGGCCTGGGGACCCGT

CCCTGGAGCCAGTGGATTTCGGATTAGCTGGAGCACAGGCAGTGGTCCG

GAGTCCAGCCAGACACTGCCCCCAGACTCTACTGCCACAGACATCACAG

GGCTGCAGCCTGGAACCACCTACCAGGTGGCTGTGTCGGTACTGCGAGG

CAGAGAGGAGGGCCCTGCTGCAGTCATCGTGGCTCGAACGGACCCACTG

GGCCCAGTGAGGACGGTCCATGTGACTCAGGCCAGCAGCTCATCTGTCA

CCATTACCTGGACCAGGGTTCCTGGCGCCACAGGATACAGGGTTTCCTG

GCACTCAGCCCACGGCCCAGAGAAATCCCAGTTGGTTTCTGGGGAGGCC

ACGGTGGCTGAGCTGGATGGACTGGAGCCAGATACTGAGTATACGGTGC

ATGTGAGGGCCCATGTGGCTGGCGTGGATGGGCCCCCTGCCTCTGTGGT

TGTGAGGACTGCCCCTGAGCCTGTGGGTCGTGTGTCGAGGCTGCAGATC

CTCAATGCTTCCAGCGACGTTCTACGGATCACCTGGGTAGGGGTCACTG

GAGCCACAGCTTACAGACTGGCCTGGGGCCGGAGTGAAGGCGGCCCCAT

GAGGCACCAGATACTCCCAGGAAACACAGACTCTGCAGAGATCCGGGGT

CTCGAAGGTGGAGTCAGCTACTCAGTGCGAGTGACTGCACTTGTCGGGG

ACCGCGAGGGCACACCTGTCTCCATTGTTGTCACTACGCCGCCTGAGGC

TCCGCCAGCCCTGGGGACGCTTCACGTGGTGCAGCGCGGGGAGCACTCG

CTGAGGCTGCGCTGGGAGCCGGTGCCCAGAGCGCAGGGCTTCCTTCTGC

ACTGGCAACCTGAGGGTGGCCAGGAACAGTCCCGGGTCCTGGGGCCCGA

GCTCAGCAGCTATCACCTGGACGGGCTGGAGCCAGCGACACAGTACCGC

GTGAGGCTGAGTGTCCTAGGGCCAGCTGGAGAAGGGCCCTCTGCAGAGG

TGACTGCGCGCACTGAGTCACCTCGTGTTCCAAGCATTGAACTACGTGT

GGTGGACACCTCGATCGACTCGGTGACTTTGGCCTGGACTCCAGTGTCC

AGGGCATCCAGCTACATCCTATCCTGGCGGCCACTCAGAGGCCCTGGCC

AGGAAGTGCCTGGGTCCCCGCAGACACTTCCAGGGATCTCAAGCTCCCA

GCGGGTGACAGGGCTAGAGCCTGGCGTCTCTTACATCTTCTCCCTGACG

CCTGTCCTGGATGGTGTGCGGGGTCCTGAGGCATCTGTCACACAGACGC

CAGTGTGCCCCCGTGGCCTGGCGGATGTGGTGTTCCTACCACATGCCAC

TCAAGACAATGCTCACCGTGCGGAGGCTACGAGGAGGGTCCTGGAGCGT

CTGGTGTTGGCACTTGGGCCTCTTGGGCCACAGGCAGTTCAGGTTGGCC

TGCTGTGTTACAGTCATCGGCCCTCCCCACTGTTCCCACTGAATGGCTC

CCATGACCTTGGCATTATCTTGCAAAGGATCCGTGACATGCCCTACATG

GACCCAAGTGGGAACAACCTGGGCACAGCCGTGGTCACAGCTCACAGAT

ACATGTTGGCACCAGATGCTCCTGGGCGCCGCCAGCACGTACCAGGGGT

GATGGTTCTGCTAGTGGATGAACCCTTGAGAGGTGACATATTCAGCCCC

ATCCGTGAGGCCCAGGCTTCTGGGCTTAATGTGGTGATGTTGGGAATGG

-continued

CTGGAGCGGACCCAGAGCAGCTGCGTCGCTTGGCGCCGGGTATGGACTC

TGTCCAGACCTTCTTCGCCGTGGATGATGGGCCAAGCCTGGACCAGGCA

GTCAGTGGTCTGGCCACAGCCCTGTGTCAGGCATCCTTCACTACTCAGC

CCCGGCCAGAGCCCTGCCCAGTGTATTGTCCAAAGGGCCAGAAGGGGGA

ACCTGGAGAGATGGGCCTGAGAGGACAAGTTGGGCCTCCTGGCGACCCT

GGCCTCCCGGGCAGGACCGGTGCTCCCGGCCCCCAGGGGCCCCCTGGAA

GTGCCACTGCCAAGGGCGAGAGGGGCTTCCCTGGAGCAGATGGGCGTCC

AGGCAGCCCTGGCCGCGCCGGGAATCCTGGGACCCCTGGAGCCCCTGGC

CTAAAGGGCTCTCCAGGGTTGCCTGGCCCTCGTGGGGACCCGGGAGAGC

GAGGACCTCGAGGCCCAAAGGGGGAGCCGGGGGCTCCCGGACAAGTCAT

CGGAGGTGAAGGACCTGGGCTTCCTGGGCGGAAAGGGGACCCTGGACCA

TCGGGCCCCCCTGGACCTCGTGGACCACTGGGGGACCCAGGACCCCGTG

GCCCCCCAGGGCTTCCTGGAACAGCCATGAAGGGTGACAAAGGCGATCG

TGGGGAGCGGGGTCCCCCTGGACCAGGTGAAGGTGGCATTGCTCCTGGG

GAGCCTGGGCTGCCGGGTCTTCCCGGAAGCCCTGGACCCCAAGGCCCCG

TTGGCCCCCCTGGAAAGAAAGGAGAAAAAGGTGACTCTGAGGATGGAGC

TCCAGGCCTCCCAGGACAACCTGGGTCTCCGGGTGAGCAGGGCCCACGG

GGACCTCCTGGAGCTATTGGCCCCAAAGGTGACCGGGGCTTTCCAGGGC

CCCTGGGTGAGGCTGGAGAGAAGGGCGAACGTGGACCCCCAGGCCCAGC

GGGATCCCGGGGGCTGCCAGGGGTTGCTGGACGTCCTGGAGCCAAGGGT

CCTGAAGGGCCACCAGGACCCACTGGCCGCCAAGGAGAGAAGGGGGAGC

CTGGTCGCCCTGGGGACCCTGCAGTGGTGGACCTGCTGTTGCTGGACC

CAAAGGAGAAAAGGGAGATGTGGGGCCCGCTGGGCCCAGAGGAGCTACC

GGAGTCCAAGGGGAACGGGGCCCACCCGGCTTGGTTCTTCCTGGAGACC

CTGGCCCCAAGGGAGACCCTGGAGACCGGGGTCCCATTGGCCTTACTGG

CAGAGCAGGACCCCCAGGTGACTCAGGGCCTCCTGGAGAGAAGGGAGAC

CCTGGGCGGCCTGGCCCCCAGGACCTGTTGGCCCCCGAGGACGAGATG

GTGAAGTTGGAGAGAAAGGTGACGAGGGTCCTCCGGGTGACCCGGGTTT

GCCTGGAAAAGCAGGCGAGCGTGGCCTTCGGGGGGCACCTGGAGTTCGG

GGGCCTGTGGGTGAAAAGGGAGACCAGGGAGATCCTGGAGAGGATGGAC

GAAATGGCAGCCCTGGATCATCTGGACCCAAGGGTGACCGTGGGGAGCC

GGGTCCCCCAGGACCCCCGGGACGGCTGGTAGACACAGGACCTGGAGCC

AGAGAGAAGGGAGAGCCTGGGGACCGCGGACAAGAGGGTCCTCGAGGGC

CCAAGGGTGATCCTGGCCTCCCTGGAGCCCCTGGGGAAAGGGGCATTGA

AGGGTTTCGGGGACCCCCAGGCCCACAGGGGGACCCAGGTGTCCGAGGC

CCAGCAGGAGAAAAGGGTGACCGGGGTCCCCCTGGGCTGGATGGCCGGA

GCGGACTGGATGGGAAACCAGGAGCCGCTGGGCCCTCTGGGCCGAATGG

TGCTGCAGGCAAAGCTGGGGACCCAGGGAGAGACGGGCTTCCAGGCCTC

CGTGGAGAACAGGGCCTCCCTGGCCCCTCTGGTCCCCCTGGATTACCGG

GAAAGCCAGGCGAGGATGGCAAACCTGGCCTGAATGGAAAAAACGGAGA

ACCTGGGGACCCTGGAGAAGACGGGAGGAAGGGAGAGAAAGGAGATTCA

-continued

GGCGCCTCTGGGAGAGAAGGTCGTGATGGCCCCAAGGGTGAGCGTGGAG

CTCCTGGTATCCTTGGACCCCAGGGGCCTCCAGGCCTCCCAGGGCCAGT

GGGCCCTCCTGGCCAGGGTTTTCCTGGTGTCCCAGGAGGCACGGGCCCC

AAGGGTGACCGTGGGGAGACTGGATCCAAAGGGGAGCAGGGCCTCCCTG

GAGAGCGTGGCCTGCGAGGAGAGCCTGGAAGTGTGCCGAATGTGGATCG

GTTGCTGGAAACTGCTGGCATCAAGGCATCTGCCCTGCGGGAGATCGTG

GAGACCTGGGATGAGAGCTCTGGTAGCTTCCTGCCTGTGCCCGAACGGC

GTCGAGGCCCCAAGGGGGACTCAGGCGAACAGGGCCCCCCAGGCAAGGA

GGGCCCCATCGGCTTTCCTGGAGAACGCGGGCTGAAGGGCGACCGTGGA

GACCCTGGCCCTCAGGGGCCACCTGGTCTGGCCCTTGGGGAGAGGGGCC

CCCCCGGGCCTTCCGGCCTTGCCGGGGAGCCTGGAAAGCCTGGTATTCC

CGGGCTCCCAGGCAGGGCTGGGGGTGTGGGAGAGGCAGGAAGGCCAGGA

GAGAGGGGAGAACGGGGAGAGAAAGGAGAACGTGGAGAACAGGGCAGAG

ATGGCCCTCCTGGACTCCCTGGAACCCCTGGGCCCCCCGGACCCCCTGG

CCCCAAGGTGTCTGTGGATGAGCCAGGTCCTGGACTCTCTGGAGAACAG

GGACCCCCTGGACTCAAGGGTGCTAAGGGGGAGCCGGGCAGCAATGGTG

ACCAAGGTCCCAAAGGAGACAGGGGTGTGCCAGGCATCAAAGGAGACCG

GGGAGAGCCTGGACCGAGGGGTCAGGACGGCAACCCGGGTCTACCAGGA

GAGCGTGGTATGGCTGGGCCTGAAGGGAAGCCGGGTCTGCAGGGTCCAA

GAGGCCCCCCTGGCCCAGTGGGTGGTCATGGAGACCCTGGACCACCTGG

TGCCCCGGGTCTTGCTGGCCCTGCAGGACCCCAAGGACCTTCTGGCCTG

AAGGGGGAGCCTGGAGAGACAGGACCTCCAGGACGGGGCCTGACTGGAC

CTACTGGAGCTGTGGGACTTCCTGGACCCCCCGGCCCTTCAGGCCTTGT

GGGTCCACAGGGGTCTCCAGGTTTGCCTGGACAAGTGGGGGAGACAGGG

AAGCCGGGAGCCCCAGGTCGAGATGGTGCCAGTGGAAAAGATGGAGACA

GAGGGAGCCCTGGTGTGCCAGGGTCACCAGGTCTGCCTGGCCCTGTCGG

ACCTAAAGGAGAACCTGGCCCCACGGGGGCCCCTGGACAGGCTGTGGTC

GGGCTCCCTGGAGCAAAGGGAGAGAAGGGAGCCCCTGGAGGCCTTGCTG

GAGACCTGGTGGGTGAGCCGGGAGCCAAAGGTGACCGAGGACTGCCAGG

GCCGCGAGGCGAGAAGGGTGAAGCTGGCCGTGCAGGGGAGCCCGGAGAC

CCTGGGGAAGATGGTCAGAAAGGGGCTCCAGGACCCAAAGGTTTCAAGG

GTGACCCAGGAGTCGGGGTCCCGGGCTCCCCTGGGCCTCCTGGCCCTCC

AGGTGTGAAGGGAGATCTGGGCCTCCCTGGCCTGCCCGGTGCTCCTGGT

GTTGTTGGGTTCCCGGGTCAGACAGGCCCTCGAGGAGAGATGGGTCAGC

CAGGCCCTAGTGGAGAGCGGGGTCTGGCAGGCCCCCCAGGGAGAGAAGG

AATCCCAGGACCCCTGGGGCCACCTGGACCACCGGGGTCAGTGGGACCA

CCTGGGGCCTCTGGACTCAAAGGAGACAAGGGAGACCCTGGAGTAGGGC

TGCCTGGGCCCCGAGGCGAGCGTGGGGAGCCAGGCATCCGGGGTGAAGA

TGGCCGCCCCGGCCAGGAGGGACCCCGAGGACTCACGGGGCCCCCTGGC

AGCAGGGGAGAGCGTGGGGAGAAGGGTGATGTTGGGAGTGCAGGACTAA

-continued

AGGGTGACAAGGGAGACTCAGCTGTGATCCTGGGGCCTCCAGGCCCACG

GGGTGCCAAGGGGGACATGGGTGAACGAGGGCCTCGGGGCTTGGATGGT

GACAAAGGACCTCGGGGAGACAATGGGGACCCTGGTGACAAGGGCAGCA

AGGGAGAGCCTGGTGACAAGGGCTCAGCCGGGTTGCCAGGACTGCGTGG

ACTCCTGGGACCCCAGGGTCAACCTGGTGCAGCAGGGATCCCTGGTGAC

CCGGGATCCCCAGGAAAGGATGGAGTGCCTGGTATCCGAGGAGAAAAAG

GAGATGTTGGCTTCATGGGTCCCCGGGGCCTCAAGGGTGAACGGGGAGT

GAAGGGAGCCTGTGGCCTTGATGGAGAGAAGGGAGACAAGGGAGAAGCT

GGTCCCCCAGGCCGCCCCGGGCTGGCAGGACACAAAGGAGAGATGGGGG

AGCCTGGTGTGCCGGGCCAGTCGGGGGCCCCTGGCAAGGAGGGCCTGAT

CGGTCCCAAGGGTGACCGAGGCTTTGACGGGCAGCCAGGCCCCAAGGGT

GACCAGGGCGAGAAAGGGGAGCGGGGAACCCCAGGAATTGGGGGCTTCC

CAGGCCCCAGTGGAAATGATGGCTCTGCTGGTCCCCCAGGGCCACCTGG

CAGTGTTGGTCCCAGAGGCCCCGAAGGACTTCAGGGCCAGAAGGGTGAG

CGAGGTCCCCCCGGAGAGAGAGTGGTGGGGGCTCCTGGGGTCCCTGGAG

CTCCTGGCGAGAGAGGGGAGCAGGGGCGGCCAGGGCCTGCCGGTCCTCG

AGGCGAGAAGGGAGAAGCTGCACTGACGGAGGATGACATCCGGGGCTTT

GTGCGCCAAGAGATGAGTCAGCACTGTGCCTGCCAGGGCCAGTTCATCG

CATCTGGATCACGACCCCTCCCTAGTTATGCTGCAGACACTGCCGGCTC

CCAGCTCCATGCTGTGCCTGTGCTCCGCGTCTCTCATGCAGAGGAGGAA

GAGCGGGTACCCCCTGAGGATGATGAGTACTCTGAATACTCCGAGTATT

CTGTGGAGGAGTACCAGGACCCTGAAGCTCCTTGGGATAGTGATGACCC

CTGTTCCCTGCCACTGGATGAGGGCTCCTGCACTGCCTACACCCTGCGC

TGGTACCATCGGGCTGTGACAGGCAGCACAGAGGCCTGTCACCCTTTTG

TCTATGGTGGCTGTGGAGGGAATGCCAACCGTTTTGGGACCCGTGAGGC

CTGCGAGCGCCGCTGCCCACCCCGGGTGGTCCAGAGCCAGGGGACAGGT

ACTGCCCAGGACTGA

Amino acid sequence of human type VII collagen (2944 AA)

(SEQ ID NO: 2)

MTLRLLVAALCAGILAEAPRVRAQHRERVTCTRLYAADIVFLLDGSSSI

GRSNFREVRSFLEGLVLPFSGAASAQGVRFATVQYSDDPRTEFGLDALG

SGGDVIRAIRELSYKGGNTRTGAAILHVADHVFLPQLARPGVPKVCILI

TDGKSQDLVDTAAQRLKGQGVKLFAVGIKNADPEELKRVASQPTSDFFF

FVNDFSILRTLLPLVSRRVCTTAGGVPVTRPPDDSTSAPRDLVLSEPSS

QSLRVQWTAASGPVTGYKVQYTPLTGLGQPLPSERQEVNVPAGETSVRL

RGLRPLTEYQVTVIALYANSIGEAVSGTARTTALEGPELTIQNTTAHSL

LVAWRSVPGATGYRVTWRVLSGGPTQQQELGPGQGSVLLRDLEPGTDYE

VTVSTLFGRSVGPATSLMARTDASVEQTLRPVILGPTSILLSWNLVPEA

RGYRLEWRRETGLEPPQKVVLPSDVTRYQLDGLQPGTEYRLTLYTLLEG

HEVATPATVVPTGPELPVSPVTDLQATELPGQRVRVSWSPVPGATQYRI

IVRSTQGVERTLVLPGSQTAFDLDDVQAGLSYTVRVSARVGPREGSASV

-continued

LTVRREPETPLAVPGLRVVVSDATRVRVAWGPVPGASGFRISWSTGSGP

ESSQTLPPDSTATDITGLQPGTTYQVAVSVLRGREEGPAAVIVARTDPL

GPVRTVHVTQASSSSVTITWTRVPGATGYRVSWHSAHGPEKSQLVSGEA

TVAELDGLEPDTEYTVHVRAHVAGVDGPPASVVVRTAPEPVGRVSRLQI

LNASSDVLRITWVGVTGATAYRLAWGRSEGGPMRHQILPGNTDSAEIRG

LEGGVSYSVRVTALVGDREGTPVSIVVTTPPEAPPALGTLHVVQRGEHS

LRLRWEPVPRAQGFLLHWQPEGGQEQSRVLGPELSSYHLDGLEPATQYR

VRLSVLGPAGEGPSAEVTARTESPRVPSIELRVVDTSIDSVTLAWTPVS

RASSYILSWRPLRGPGQEVPGSPQTLPGISSSQRVTGLEPGVSYIFSLT

PVLDGVRGPEASVTQTPVCPRGLADVVFLPHATQDNAHRAEATRRVLER

LVLALGPLGPQAVQVGLLSYSHRPSPLFPLNGSHDLGIILQRIRDMPYM

DPSGNNLGTAVVTAHRYMLAPDAPGRRQHVPGVMVLLVDEPLRGDIFSP

IREAQASGLNVVMLGMAGADPEQLRRLAPGMDSVQTFFAVDDGPSLDQA

VSGLATALCQASFTTQPRPEPCPVYCPKGQKGEPGEMGLRGQVGPPGDP

GLPGRTGAPGPQGPPGSATAKGERGFPGADGRPGSPGRAGNPGTPGAPG

LKGSPGLPGPRGDPGERGPRGPKGEPGAPGQVIGGEGPGLPGRKGDPGP

SGPPGPRGPLGDPGPRGPPGLPGTAMKGDKGDRGERGPPGPGEGGIAPG

EPGLPGLPGSPGPQGPVGPPGKKGEKGDSEDGAPGLPGQPGSPGEQGPR

GPPGAIGPKGDRGFPGPLGEAGEKGERGPPGPAGSRGLPGVAGRPGAKG

PEGPPGPTGRQGEKGEPGRPGDPAVVGPAVAGPKGEKGDVGPAGPRGAT

GVQGERGPPGLVLPGDPGPKGDPGDRGPIGLTGRAGPPGDSGPPGEKGD

PGRPGPPGPVGPRGRDGEVGEKGDEGPPGDPGLPGKAGERGLRGAPGVR

GPVGEKGDQGDPGEDGRNGSPGSSGPKGDRGEPGPPGPPGRLVDTGPGA

REKGEPGDRGQEGPRGPKGDPGLPGAPGERGIEGFRGPPGPQGDPGVRG

PAGEKGDRGPPGLDGRSGLDGKPGAAGPSGPNGAAGKAGDPGRDGLPGL

RGEQGLPGPSGPPGLPGKPGEDGKPGLNGKNGEPGDPGEDGRKGEKGDS

GASGREGRDGPKGERGAPGILGPQGPPGLPGPVGPPGQGFPGVPGGTGP

KGDRGETGSKGEQGLPGERGLRGEPGSVPNVDRLLETAGIKASALREIV

ETWDESSGSFLPVPERRRGPKGDSGEQGPPGKEGPIGFPGERGLKGDRG

DPGPQGPPGLALGERGPPGPSGLAGEPGKPGIPGLPGRAGGVGEAGRPG

ERGERGEKGERGEQGRDGPPGLPGTPGPPGPPGPKVSVDEPGPGLSGEQ

GPPGLKGAKGEPGSNGDQGPKGDRGVPGIKGDRGEPGPRGQDGNPGLPG

ERGMAGPEGKPGLQGPRGPPGPVGGHGDPGPPGAPGLAGPAGPQGPSGL

KGEPGETGPPGRGLTGPTGAVGLPGPPGPSGLVGPQGSPGLPGQVGETG

KPGAPGRDGASGKDGDRGSPGVPGSPGLPGPVGPKGEPGPTGAPGQAVV

GLPGAKGEKGAPGGLAGDLVGEPGAKGDRGLPGPRGEKGEAGRAGEPGD

PGEDGQKGAPGPKGFKGDPGVGVPGSPGPPGPPGVKGDLGLPGLPGAPG

VVGFPGQTGPRGEMGQPGPSGERGLAGPPGREGIPGPLGPPGPPGSVGP

PGASGLKGDKGDPGVGLPGPRGERGEPGIRGEDGRPGQEGPRGLTGPPG

SRGERGEKGDVGSAGLKGDKGDSAVILGPPGPRGAKGDMGERGPRGLDG

DKGPRGDNGDPGDKGSKGEPGDKGSAGLPGLRGLLGPQGQPGAAGIPGD

-continued

PGSPGKDGVPGIRGEKGDVGFMGPRGLKGERGVKGACGLDGEKGDKGEA

GPPGRPGLAGHKGEMGEPGVPGQSGAPGKEGLIGPKGDRGFDGQPGPKG

DQGEKGERGTPGIGGFPGPSGNDGSAGPPGPPGSVGPRGPEGLQGQKGE

RGPPGERVVGAPGVPGAPGERGEQGRPGPAGPRGEKGEAALTEDDIRGF

VRQEMSQHCACQGQFIASGSRPLPSYAADTAGSQLHAVPVLRVSHAEEE

ERVPPEDDEYSEYSEYSVEEYQDPEAPWDSDDPCSLPLDEGSCTAYTLR

WYHRAVTGSTEACHPFVYGGCGGNANRFGTREACERRCPPRVVQSQGTG

TAQD*

In an embodiment, the COL7A1 gene comprises or consists of a nucleic acid sequence having 70%, 80%, 85%, 90%, 95%, 96%, 97%, 98% or 99% or more sequence identity with the nucleic acid sequence of SEQ ID NO: 1. In a different embodiment, the COL7A1 gene comprises or consists of a nucleic acid sequence wherein 0 to 30, 0 to 20, 0 to 10, 0 to 5, 0 to 3, 0 to 2 or 0 to 1 base(s) is deleted, substituted, or added with respect to the nucleic acid sequence of SEQ ID NO: 1. In a further embodiment, the COL7A1 gene comprises or consists of the nucleic acid sequence of SEQ ID NO: 1.

In an embodiment, the type VII collagen comprises or consists of an amino acid sequence having 70%, 80%, 85%, 90%, 95%, 96%, 97%, 98% or 99% or more sequence identity with the amino acid sequence of SEQ ID NO: 2. In a different embodiment, the type VII collagen comprises or consists of an amino acid sequence wherein 0 to 30, 0 to 20, 0 to 10, 0 to 5, 0 to 3, 0 to 2 or 0 to 1 amino acid residue(s) is deleted, substituted, or added with respect to the amino acid sequence of SEQ ID NO: 2. In a further embodiment, the type VII collagen comprises or consists of the amino acid sequence of SEQ ID NO: 2.

In an embodiment, the COL7A1 gene comprises or consists of a nucleic acid sequence that encodes an amino acid sequence having 70%, 80%, 85%, 90%, 95%, 96%, 97%, 98% or 99% or more sequence identity with the amino acid sequence of SEQ ID NO: 2. In a different embodiment, the COL7A1 gene comprises or consists of a nucleic acid sequence that encodes an amino acid sequence wherein 0 to 30, 0 to 20, 0 to 10, 0 to 5, 0 to 3, 0 to 2 or 0 to 1 amino acid residue(s) is deleted, substituted, or added with respect to the amino acid sequence of SEQ ID NO: 2.

As used herein, the term “sequence identity” with respect to a nucleic acid sequence or an amino acid sequence means the proportion of bases or amino acid residues that match between two sequences that are optimally aligned (aligned to be maximally matched) over the entire region of the sequence to be compared. The sequence to be compared may have an addition or a deletion (eg, a gap) in the optimal alignment of the two sequences. The sequence identity can be calculated using a program such as FASTA, BLAST, or CLUSTAL W provided in a public database (for example, DDBJ (http://www.ddbj.nig.ac.jp)). Alternatively, the sequence identity can be obtained using a commercially available sequence analysis software (for example, Vector NTI® software, GENETYX® ver. 12).

The cell may be genetically modified by any method. In an embodiment, the cell is genetically modified by genome editing such as the CRISPR system (eg, CRISPR/Cas9, CRISPR/Cpf1), TALEN, or ZFN. In a different embodiment, the cell is genetically modified by a viral vector such as a retroviral vector, lentiviral vector, adenoviral vector, or adeno-associated viral vector. In a further embodiment, the cell is genetically modified by CRISPR/Cas9. In a further embodiment, the cell is genetically modified by a retroviral vector or a lentiviral vector.

In genome editing, causing cleavage in the genome and introducing a donor vector comprising a sequence of interest into the cell can insert the sequence of interest into the cleavage site of the genome. The sequence to be inserted into the genome can be a COL7A1 gene or a sequence to be replaced with a portion containing a mutation in the COL7A1 gene (for example, a partial sequence of a COL7A1 gene). In addition to the sequence of interest, the donor vector may comprise a regulatory sequence such as a promoter or enhancer that controls the expression of the sequence of interest, or other elements such as a drug resistance gene for cell selection, and also may comprise, at both ends, sequences homogeneous to both ends of the insertion site of the genome. The donor vector can be introduced into a desired site as a result of non-homologous end binding or homologous recombination. As the donor vector, a plasmid, an adeno-associated viral vector, an integrase-deficient lentiviral vector, or any of other viral vectors can be used.

In the CRISPR system, an endonuclease such as Cas9 or Cas12 (eg, Cas12a (also called Cpf1), Cas12b, Cas12e) recognizes a specific base sequence, called PAM sequence, and the double strand of the target DNA is cleaved by the action of the endonuclease. When the endonuclease is Cas9, it cleaves about 3-4 bases upstream of the PAM sequence. Examples of endonucleases include Cas9 of *S. pyogenes, S. aureus, N. meningitidis, S. thermophilus*, or *T. denticola*, and Cpf1 of *L. bacterium* ND2006 or Acidaminococcus sp. BV3L6. The PAM sequence varies depending on the endonuclease, and the PAM sequence of Cas9 in *S. pyogenes* is NGG, for example. A gRNA comprises a sequence of about 20 bases upstream of the PAM sequence (target sequence) or a sequence complementary thereto on the 5' end side, and plays a role of recruiting an endonuclease to the target sequence. The sequences other than the target sequence (or a sequence complementary thereto) of a gRNA can be appropriately determined by those skilled in the art depending on the endonuclease to be used. A gRNA may comprises a crRNA (CRISPR RNA), which comprises the target sequence or a sequence complementary thereto and is responsible for the sequence specificity of the gRNA, and a tracrRNA (Trans-activating crRNA), which contributes to the formation of a complex with Cas9 by forming a double strand. The crRNA and tracrRNA may exist as separate molecules. When the endonuclease is Cpf1, the crRNA alone functions as a gRNA. In the present specification, a gRNA comprising elements necessary for the function as a gRNA on a single strand may be particularly referred to as a sgRNA. The gRNA sequence can be determined by a tool available for target sequence selection and gRNA design, such as CRISPRdirect (https://crispr.dbcls.jp/).

A vector comprising a nucleic acid sequence encoding a gRNA and a nucleic acid sequence encoding an endonuclease may be introduced into and expressed in a cell, or a gRNA and an endonuclease protein that have been prepared extracellularly may be introduced into a cell. The endonuclease may include a nuclear localization signal. The nucleic acid sequence encoding a gRNA and the nucleic acid sequence encoding an endonuclease may be present on different vectors. Methods for introducing the vector, gRNA, and endonuclease into a cell include, but are not limited to, lipofection, electroporation, microinjection, calcium phosphate method, and DEAE-dextran method.

The present disclosure provides a gRNA and a vector comprising a nucleic acid sequence encoding a gRNA that can be used for the introduction of a COL7A1 gene into the genome. In an embodiment, the gRNA comprises any of the sequences of SEQ ID NOs: 3-5 or a sequence complementary thereto.

In the case of viral vectors, a COL7A1 gene can be introduced into the genome of a cell when a retroviral vector or a lentiviral vector having integrase activity is used. Alternatively, an integrase-deficient retroviral or lentiviral vector may be used. Integrase-deficient vectors lack integrase activity, for example, due to a mutation in the integrase gene. When an integrase-deficient vector, or an adenoviral vector or an adeno-associated viral vector is used, the sequence incorporated into the vector is not usually introduced into the genome of a cell. For example, when a COL7A1 gene is incorporated into an integrase-deficient lentiviral vector or an adenoviral vector, type VII collagen is expressed from the COL7A1 gene of the vector existing in the cell (in the nucleus).

A viral vector comprises a sequence encoding a COL7A1 gene and may contain a regulatory sequence such as a promoter or enhancer that controls the expression of the COL7A1 gene and other elements such as a drug resistance gene for cell selection. A viral vector may be prepared by any method known in the art. For example, a retroviral or lentiviral vector can be prepared by introducing a viral 1 vector plasmid comprising LTR sequences at both ends (5' LTR and 3' LTR), a packaging signal, and a sequence of interest into a packaging cell with one or more plasmid vectors expressing structural proteins of the virus, such as Gag, Pol, and Env, or into a packaging cell that expresses such structural proteins. Examples of packaging cells include, but are not limited to, 293T cells, 293 cells, Hela cells, COS1 cells, and COS7 cells. The viral vector may be pseudotyped and may express an envelope protein such as the vesicular stomatitis virus G protein (VSV-G). The sequence of interest can be introduced into a target cell by infecting the target cell with a viral vector thus prepared.

In an embodiment, the viral vector is a lentiviral vector. Examples of lentiviral vectors include, but are not limited to, HIV (human immunodeficiency virus) (for example, HIV-1 and HIV-2), SIV (simian immunodeficiency virus), FIV (feline immunodeficiency virus), MVV (Maedi-Visna virus), EV1 (Maedi-Visna-like virus), EIAV (equine infectious anemia virus), and CAEV (caprine arthritis encephalitis virus). In an embodiment, the lentiviral vector is HIV.

As an example, a lentiviral vector can be prepared as follows. First, a viral vector plasmid encoding the viral genome, one or more plasmid vectors expressing Gag, Pol, and Rev (and optionally Tat), and one or more plasmid vectors expressing envelope proteins such as VSV-G are introduced into a packaging cell. The viral vector plasmid comprises LTR sequences at both ends (5' LTR and 3' LTR), a packaging signal, and a COL7A1 gene and a promoter that controls its expression (eg, CMV promoter, EF1α promoter, or hCEF promoter). The 5' LTR functions as a promoter that induces transcription of the viral RNA genome, but may be replaced with a different promoter, such as CMV promoter, to enhance the expression of the RNA genome. Within the cell, the viral RNA genome is transcribed from the vector plasmid and packaged to form a viral core. The viral core is transported to the cell membrane of the packaging cell, encapsulated in the cell membrane, and released as a viral particle from the packaging cell. The released virus particle can be recovered from the culture supernatant of the packaging cell. For example, the virus particle can be recovered by any of conventional purification methods such as centrifugation, filter filtration, and column purification. A lentiviral vector can also be prepared by using a kit such as Lentiviral High Titer Packaging Mix, Lenti-X™ Packaging Single Shots (Takara Bio Inc.), and ViraSafe™ Lentivirus Complete Expression System (Cell Biolabs Inc.). An adeno-associated viral vector can be prepared by using a kit such as AAVpro® Helper Free System (Takara Bio Inc.).

A cell into which a sequence of interest has been introduced can be detected by Southern blotting or PCR. The sequence of interest need only be introduced into at least one of the alleles.

In an embodiment of the composition of the present disclosure, the mesenchymal stem cell is the most abundant cell in the composition. In a further embodiment, the mesenchymal stem cell accounts for 708, 808, 858, 90%, 95%, 96%, 97%, 98% or 99% or more of cells comprised in the composition. In a further embodiment, the composition of the present disclosure is substantially free of cells other than the mesenchymal stem cell. The expression "substantially free of cells other than the mesenchymal stem cell" means that the composition only comprises a cell obtained by a method that is usually understood by those skilled in the art to be a method for obtaining a mesenchymal stem cell.

The number of cells comprised in a composition is an amount required to exert a desired effect (also referred to herein as an effective amount), and it is appropriately determined by those skilled in the art in consideration of factors such as the age, body weight, and medical condition of the patient, the type of cells and method for genetic modification. The number of cells is not limited to, but can be, for example, 1 cell to $1\times10^7$ cells, 1x10 cells to $1\times10^7$ cells, $1\times10^2$ cells to $1\times10^7$ cells, $1\times10^3$ cells to $1\times10^7$ cells, $1\times10^4$ cells to $1\times10^7$ cells, $1\times10^5$ cells to $1\times 10^7$ cells, $1\times10^5$ cells to $5\times10^6$ cells, $5\times10^5$ cells to $1\times10^6$ cells, or $1\times10^5$ cells to $1\times10^6$ cells. The composition may comprise a pharmaceutically acceptable carrier and/or an additive in addition to the cell. Examples of pharmaceutically acceptable carriers include water, medium, saline, infusion containing glucose, D-sorbitol, D-mannitol or others, and phosphate buffered saline (PBS). Examples of additives include solubilizers, stabilizers, and preservatives. The dosage form of the composition is not particularly limited to, but can be a parenteral preparation such as an injection. Examples of injections include solution injections, suspension injections, emulsion injections, and injections to be prepared before use. The composition may be frozen and may contain a cryoprotectant such as DMSO, glycerol, polyvinylpyrrolidone, polyethylene glycol, dextran, or sucrose.

The composition of the present disclosure can be administered systemically or topically. In an embodiment, the composition is administered to an affected area of a patient with dystrophic epidermolysis bullosa. As used herein, the affected area means a blister or an area in the vicinity of a blister. In a further embodiment, the composition is administered intradermally at the site of a blister or administered into a blister. In a further embodiment, the composition is administered into a blister. In the present specification, administration into a blister means administration to the space under the epidermis of a blister. The intrablister administration can reduce patient distress as compared to intradermal or subcutaneous administration, and type VII collagen can be well expressed near the basement membrane. The number of cells administered per site is an amount required to exert a desired effect (effective amount), and it is appropriately determined by those skilled in the art in consideration of factors such as the age, body weight, and medical condition of the patient, the type of cells, and method for genetic modification. The number of cells is not limited to, but can be for example, cell to $1\times10^7$ cells, 1x10 cells to $1\times10^7$ cells, $1\times10^2$ cells to $1\times10^7$ cells, $1\times10^3$ cells to $1\times10^7$ cells, $1\times10^4$ cells to $1\times10^7$ cells, $1\times10^5$ cells to $1\times10^7$ cells, $1\times10^5$ cells to $5\times10^6$ cells, $5\times10^5$ cells to $1\times10^6$ cells, or $1\times10^5$ cells to $1\times10^6$ cells. In an embodiment, the number of cells to be administered per blister is 1 cell to $1\times10^7$ cells, 1x10 cells to $1\times10^7$ cells, $1\times10^2$ cells to $1\times10^7$ cells, $1\times10^3$ cells to $1\times10^7$ cells, $1\times10^4$ cells to $1\times10^7$ cells, $1\times10^5$ cells to $1\times10^7$ cells, $1\times10^5$ cells to $5\times10^6$ cells, $5\times10^5$ cells to $1\times10^6$ cells, or $1\times10^5$ cells to $1\times10^6$ cells. The amount to be administered per blister may be adjusted according to the size of a blister when the above amount is considered for a standard blister having a diameter of 7 to 8 mm when circularly approximated.

Exemplary embodiments of the present invention are described below.

[1] A composition for use in the treatment of dystrophic epidermolysis bullosa, comprising a cell obtained from a patient with dystrophic epidermolysis bullosa, wherein the cell is a mesenchymal stem cell and genetically modified to produce type VII collagen.

[2] The composition according to item 1, wherein the cell is genetically modified by introducing a COL7A1 gene.

[3] The composition according to item 2, wherein the COL7A1 gene is introduced into the genome of the cell.

[4] The composition according to item 2 or 3, wherein the COL7A1 gene comprises a nucleic acid sequence having 70%, 80%, 85%, 90%, 95%, 96%, 97%, 98% or 99% or more sequence identity with the nucleic acid sequence of SEQ ID NO: 1, or a nucleic acid sequence that encodes an amino acid sequence having 70%, 80%, 85%, 90%, 95%, 96%, 97%, 98% or 99% or more sequence identity with the amino acid sequence of SEQ ID NO: 2.

[5] The composition according to any one of items 1 to 4, wherein the mesenchymal stem cell is a bone marrow-derived mesenchymal stem cell.

[6] The composition according to any one of items 1 to 5, wherein the mesenchymal stem cell is the most abundant cell in the composition.

[7] The composition according to any one of items 1 to 6, wherein the mesenchymal stem cell accounts for 70%, 808, 85%, 90%, 95%, 96%, 97%, 98% or 99% or more of cells comprised in the composition.

[8] The composition according to any one of items 1 to 7, wherein the composition does not substantially comprise cells other than the mesenchymal stem cell.

[9] The composition according to any one of items 1 to 8, which is to be administered to an affected area.

[10] The composition according to any one of items 1 to 9, which is to be administered into a blister.

[11] The composition according to any one of items 1 to 10, wherein the cell is genetically modified by genome editing.

[12] The composition according to item 11, wherein the genome editing is carried out by CRISPR/Cas9.

[13] The composition according to any one of items 1 to 10, wherein the cell is genetically modified by a viral vector.

[14] The composition according to item 13, wherein the viral vector is a retroviral vector or a lentiviral vector.

[15] The composition according to item 13 or 14, wherein the viral vector is a lentiviral vector.

[16] A composition for use in the treatment of dystrophic epidermolysis bullosa, comprising a cell that produces type VII collagen, wherein the composition is to be administered into a blister.

[17] The composition according to item 16, wherein the cell is a cell genetically modified to produce type VII collagen.

[18] The composition according to item 17, wherein the cell is genetically modified by introducing a COL7A1 gene.

[19] The composition according to item 18, wherein the COL7A1 gene is introduced into the genome of the cell.

[20] The composition according to item 18 or 19, wherein the COL7A1 gene comprises a nucleic acid sequence having 70%, 80%, 85%, 90%, 95%, 96%, 97%, 98% or 99% or more sequence identity with the nucleic acid sequence of SEQ ID NO: 1, or a nucleic acid sequence that encodes an amino acid sequence having 70%, 80%, 85%, 90%, 95%, 96%, 97%, 98% or 99% or more sequence identity with the amino acid sequence of SEQ ID NO: 2.

[21] The composition according to any one of items 17 to 20, wherein the cell is a cell obtained from a patient with dystrophic epidermolysis bullosa.

[22] The composition according to any one of items 16 to 21, wherein the cell is a cell obtained from bone marrow.

[23] The composition according to any one of items 16 to 22, wherein the cell is a mesenchymal stem cell.

[24] The composition according to item 23, wherein the mesenchymal stem cell is a bone marrow-derived mesenchymal stem cell.

[25] The composition according to item 23 or 24, wherein the mesenchymal stem cell is the most abundant cell in the composition.

[26] The composition according to any one of items 23 to 25, wherein the mesenchymal stem cell accounts for 708, 80%, 85%, 90%, 95%, 96%, 97%, 98% or 99% or more of cells comprised in the composition.

[27] The composition according to any one of items 23 to 26, wherein the composition does not substantially comprise cells other than the mesenchymal stem cell.

[28] The composition according to any one of items 17 to 27, wherein the cell is genetically modified by genome editing.

[29] The composition according to item 28, wherein the genome editing is carried out by CRISPR/Cas9.

[30] The composition according to any one of items 17 to 27, wherein the cell is genetically modified by a viral vector.

[31] The composition according to item 30, wherein the viral vector is a retroviral vector or a lentiviral vector.

[32] The composition according to item 30 or 31, wherein the viral vector is a lentiviral vector.

[33] A method of producing a composition for use in the treatment of dystrophic epidermolysis bullosa, comprising genetically modifying a cell to produce type VII collagen, and, preparing a composition comprising the genetically modified cell.

[34] A method of treating dystrophic epidermolysis bullosa, comprising administering to a patient of dystrophic epidermolysis bullosa a composition comprising a cell that produces type VII collagen.

[35] The method according to item 34, wherein the cell is genetically modified to produce type VII collagen.

[36] The method according to item 35, wherein the cell is genetically modified by introducing a COL7A1 gene.

[37] The method according to item 36, wherein the COL7A1 gene is introduced into the genome of the cell.

[38] The composition according to item 36 or 37, wherein the COL7A1 gene comprises a nucleic acid sequence having 70%, 80%, 85%, 90%, 95%, 96%, 97%, 98% or 99% or more sequence identity with the nucleic acid sequence of SEQ ID NO: 1, or a nucleic acid sequence that encodes an amino acid sequence having 70%, 80%, 85%, 90%, 95%, 96%, 97%, 98% or 99% or more sequence identity with the amino acid sequence of SEQ ID NO: 2.

[39] The method according to any one of items 35 to 38, wherein the cell is genetically modified by genome editing.

[40] The method according to item 39, wherein the genome editing is carried out by CRISPR/Cas9.

[41] The method according to any one of items 35 to 38, wherein the cell is genetically modified by a viral vector.

[42] The method according to item 41, wherein the viral vector is a retroviral vector or a lentiviral vector.

[43] The method according to item 41 or 42, wherein the viral vector is a lentiviral vector.

[44] The method according to any one of items 35 to 43, further comprising, prior to the administering to the patient, genetically modifying a cell to produce type VII collagen.

[45] The method according to item 33 or 44, comprising genetically modifying the cell by introducing a COL7A1 gene.

[46] The method according to item 45, comprising introducing the COL7A1 gene into the genome of the cell.

[47] The method according to item 45 or 46, wherein the COL7A1 gene comprises a nucleic acid sequence having 70%, 80%, 85%, 90%, 95%, 96%, 97%, 98% or 99% or more sequence identity with the nucleic acid sequence of SEQ ID NO: 1, or a nucleic acid sequence that encodes an amino acid sequence having 70%, 80%, 85%, 90%, 95%, 96%, 97%, 98% or 99% or more sequence identity with the amino acid sequence of SEQ ID NO: 2.

[48] The method according to any one of items 33 and 44 to 47, comprising genetically modifying the cell by genome editing.

[49] The method according to item 48, wherein the genome editing is carried out by CRISPR/Cas9.

[50] The method according to any one of items 33 and 44 to 47, comprising genetically modifying the cell with a viral vector.

[51] The method according to item 50, wherein the viral vector is a retroviral vector or a lentiviral vector.

[52] The method according to item 50 or 51, wherein the viral vector is a lentiviral vector.

[53] The method according to any one of items 33 to 52, wherein the cell is a cell obtained from a patient with dystrophic epidermolysis bullosa.

[54] The method according to any one of items 33 and 44 to 53, further comprising, prior to the genetically modifying, obtaining a cell from a patient with dystrophic epidermolysis bullosa.

[55] The method according to any one of items 33 to 54, wherein the cell is a cell obtained from bone marrow.

[56] The method according to any one of items 33 to 55, wherein the cell is a mesenchymal stem cell.

[57] The method according to item 56, wherein the mesenchymal stem cell is a bone marrow-derived mesenchymal stem cell.

[58] The method according to item 56 or 57, wherein the mesenchymal stem cell is the most abundant cell in the composition.

[59] The method according to any one of items 56 to 58, wherein the mesenchymal stem cell accounts for 708, 80%, 85%, 90%, 95%, 96%, 97%, 98% or 99% or more of cells comprised in the composition.

[60] The method according to any one of items 56 to 59, wherein the composition does not substantially comprise cells other than the mesenchymal stem cell.

[61] The method according to any one of items 34 to 60, comprising administering the composition to an affected area.

[62] The method according to any one of items 34 to 61, comprising administering the composition into a blister.

[63] Use of a composition comprising a cell obtained from a patient with dystrophic epidermolysis bullosa for the manufacture of a medicament for treating dystrophic epidermolysis bullosa, wherein comprises the cell a mesenchymal stem cell and the cell is genetically modified to produce type VII collagen.

[64] Use of a composition comprising a cell that produces type VII collagen for the manufacture of a medicament for treating dystrophic epidermolysis bullosa, wherein the composition is to be administered into a blister.

[65] Use of a composition comprising a cell obtained from a patient with dystrophic epidermolysis bullosa for treating dystrophic epidermolysis bullosa, wherein the cell comprises a mesenchymal stem cell and the cell is genetically modified to produce type VII collagen.

[66] Use of a composition comprising a cell that produces type VII collagen for treating dystrophic epidermolysis bullosa, wherein the composition is to be administered into a blister.

[67] A gRNA comprising a sequence of any one of SEQ ID NOS: to 5 or a sequence complementary thereto.

[68] A vector comprising a nucleic acid sequence encoding the gRNA of item 67.

The present invention is described in more detail with reference to the examples hereinafter, but not limited to the embodiments described below.

EXAMPLES

1. Design of Genome Editing

Three types of sgRNAs were prepared in order to select a site with good cleavage efficiency by the CRISPR-Cas9 system in the AAVS1 (Adeno-associated virus integration site 1) region in the human genome. The AAVS1 region is a safe region that is not easily affected by gene transfer (safe harbor). Since the CRISPR-Cas9 system recognized the base sequence of "NGG" and cleaved 3 bases upstream of the sequence, regions each having "GG" at the end were selected and sgRNAs each containing a sequence of 20 bases upstream of "NGG" were designed (sgAAVS1-#1 to #3) (FIG. 1, top; Table 1).

TABLE 1

| sgRNA | Target sequence | SEQ ID NO. |
|---|---|---|
| sgAAVS1-#1 | ACCCCACAGTGGGGCCACTA | 3 |
| sgAAVS1-#2 | GTCACCAATCCTGTCCCTAG | 4 |
| sgAAVS1-#3 | GGGGCCACTAGGGACAGGAT | 5 |

An oligonucleotide consisting of a sequence of any one of SEQ ID NOS: 3 to 5 was annealed with its complementary strand and cloned into the Bbs1 site of eSpCas9 (1.1) (Addgene plasmid #71814). This plasmid (2.5 μg) was introduced into HEK293 cells (human fetal kidney cell line) seeded in 6-well dishes by Lipofectamin 3000 (Thermo Fisher Scientific). Forty-eight hours after transfection, genomic DNA was extracted from the cells and the region containing the target site was amplified by PCR. The PCR amplified fragments were subjected to heat treatment to be a single chain, annealed by slow cooling, and then treated with a mismatch site-specific endonuclease. The resulting product was fractionated by electrophoresis, the degree of insertion or deletion mutation introduced by the genome cleavage was measured from the density of the band, and the genome editing efficiency was calculated by the following formula (In the formula, "a" indicates the concentration of the band that was not digested, and "b" and "c" indicate the concentrations of the cleaved bands.).

$$\text{Indel (\%)}=100\times(1-\sqrt{(1-f\text{cut})}),\ f_{cut}=(b+c)/(a+b+c)$$

All sgRNAs of sgAAVS1-#1 to #3 produced a short DNA fragment different from the control, confirming that double-strand break occurred (FIG. 1, bottom). In the following experiments, sgAAVS1-#3, which had the highest cleavage efficiency, was used.

2. Introduction of COL7A1 Gene into BM-MSCs

Figure 2:
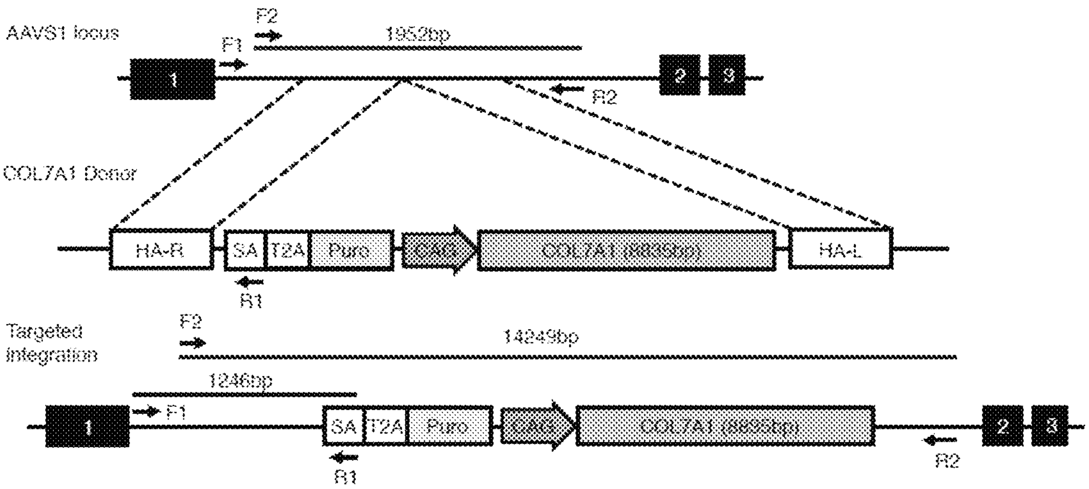
FIG. 2 is an explanatory diagram of genome editing in which a COL7A1 gene is introduced into the AAVS1 region. HA-R and HA-L indicate portions having homologous sequences, SA indicates a splice acceptor sequence, T2A indicates a T2A sequence encoding a T2A peptide, Puro indicates a puromycin resistance gene, and CAG indicates a CAG promoter sequence. The length from F2 to R2 in the wild-type genome (top) is 1952 bp, and the length from F1 to R1 and that from F2 to R2 in the genome into which the COL7A1 gene was introduced (bottom) is 1246 bp and 14249 bp, respectively.

For the introduction of a COL7A1 gene into the AAVS1 region, a plasmid expressing the COL7A1 gene under the control of the CAG promoter was designed (FIG. 2). The COL7A1 CDNA was obtained from Flexi ORF sequence-verified clone (Promega, Madison, WI, USA). The COL7A1 CDNA was subcloned into the pENTR1A plasmid (ThermoFisher Scientific) to prepare pENTR1A-COL7A1, and pAAVS-P-CAG-COL7A1 was obtained by using LR recombinase (ThermoFisher Scientific) and pAAVS-P-CAG-DEST (Addgene plasmid #80490) and pENTR1A-COL7A1.

Figure 3:
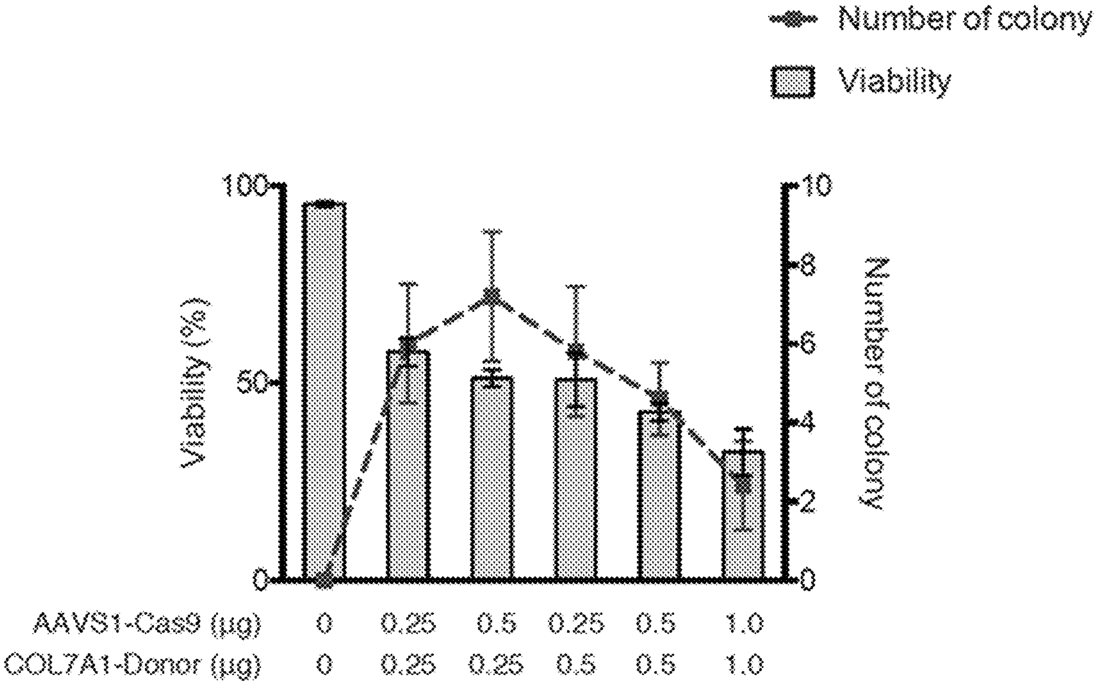
FIG. 3 shows the gene transfer efficiency by the CRISPR-Cas9 system and the cell viability after gene transfer in mesenchymal stem cells (MSCs). The dashed line indicates the number of genome-edited cells, and the column indicates the cell viability.

Since the transfer efficiency increased but the cell viability decreased as the amount of plasmid increased with respect to the cells, first, the experimental conditions in which both the cell viability and the transfer efficiency were good were examined. To human bone marrow-derived mesenchymal stem cells (BM-MSCs) [PromoCell (Heidelberg, Germany) or Lonza (Basel, Switzerland)] ($1\times10^5$ cells), pAAVS-P-CAG-COL7A1 (0 μg, 0.25 μg, 0.5 μg or 1.0 μg) and eSpCas9 (1.1) expressing sgAAVS1-#3 (0 μg, 0.25 μg, 0.5 μg, or 1.0 μg) were introduced by electroporation. All cells were collected 24 hours after transfection, and the viability was calculated from the number of trypan blue staining-positive cells (dead cells) with respect to the total number of cells. In addition, 48 hours after transfection, BM-MSCs were cultured in a medium containing 0.5 μg/mL puromycin (Invivogen, San Diego, CA, USA) for about 2 weeks for selection, and the number of isolated colonies was determined to measure the efficiency of genome editing. Based on the results shown in FIG. 3, 0.25 μg of pAAVS-P-CAG-COL7A1 and 0.5 μg of eSpCas9 (1.1) were used in the following experiments.

To BM-MSCs ($1\times10^5$ cells), pAAVS-P-CAG-COL7A1 (0.25 μg) and eSpCas9 (1.1) expressing sgAAVS1-#3 (0.5 μg) were introduced by electroporation. Forty-eight hours after transfection, BM-MSCs were cultured in a medium containing 0.5 μg/mL puromycin (Invivogen, San Diego, CA, USA) for about weeks for selection. Genomic DNA was extracted from the BM-MSCs, and genome editing and introduction of the COL7A1 gene were confirmed by PCR.

Figure 4:
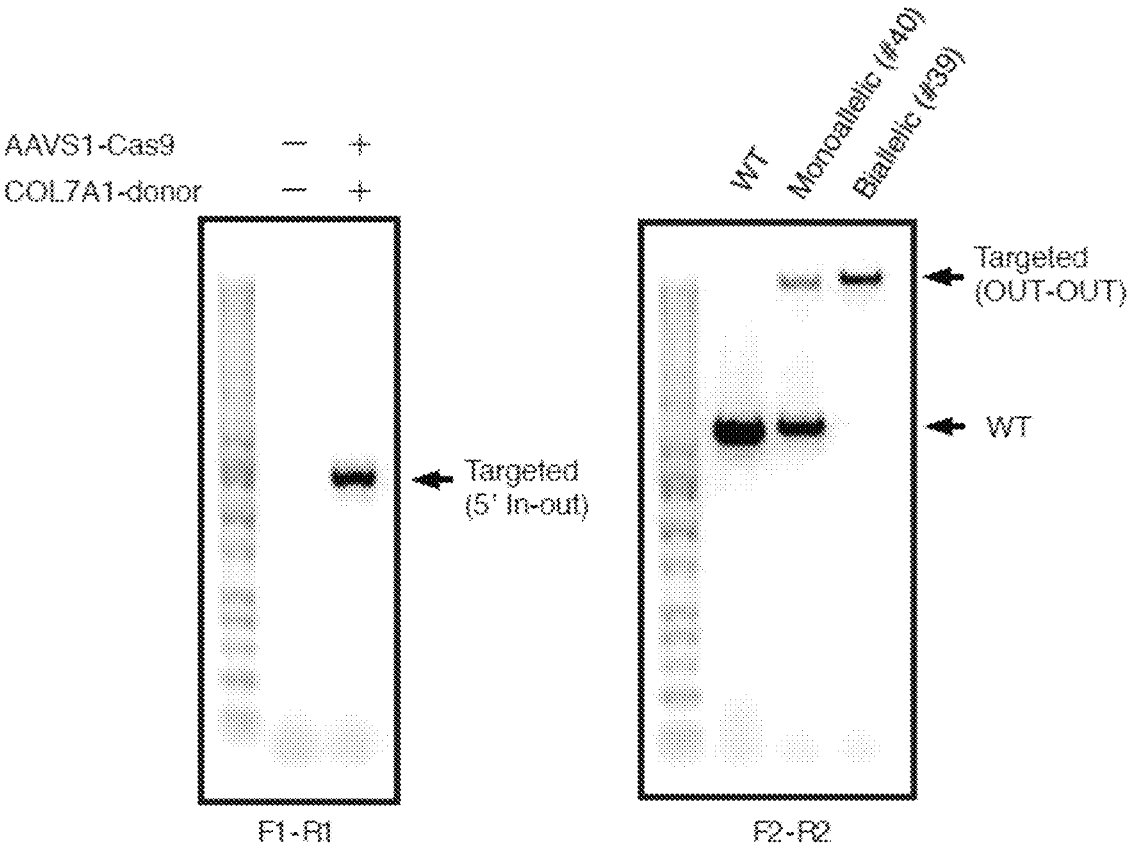
FIG. 4 shows the results of confirming the introduction of the COL7A1 gene by genome editing.

The PCR product was obtained by amplification between F1-R1, confirming that genome editing had occurred (FIG. 4, F1-R1). Also, long DNA not present in the wild type (WT) was detected in the PCR product between F2-R2, and it indicated that the COL7A1 gene was introduced (FIG. 4, F2-R2). The COL7A1 gene was introduced into one of the alleles (FIG. 4, Monoallelic) or both (FIG. 4, Biallelic).

Figure 5:
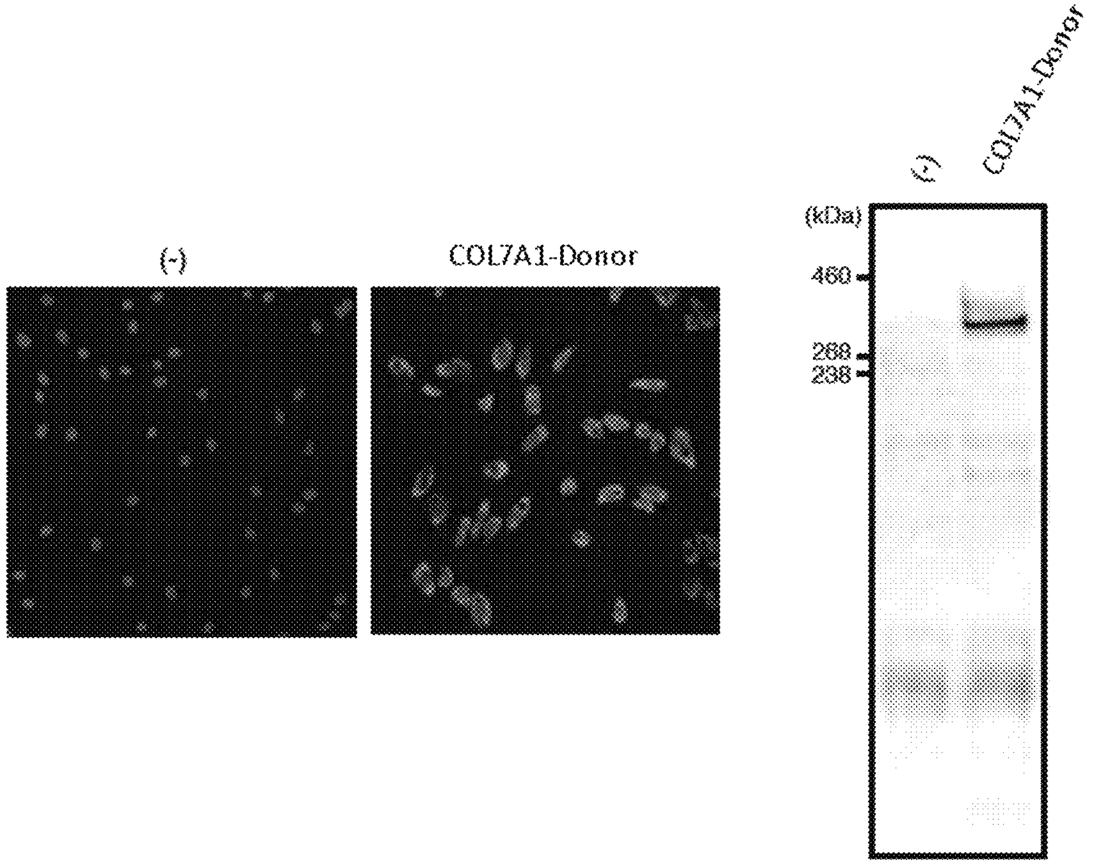
FIG. 5 shows the expression of type VII collagen in MSCs. The symbol "(-)" indicates a control without genome editing, and the symbol "COL7A1-Donor" indicates genetically modified MSCs in which a COL7A1 gene was introduced by genome editing. The photo on the left shows the results of immunostaining of the cells, and the graph on the right shows the results of Western blotting of the culture supernatant of the cells.

Since collagen was a secretory protein and exuded to the outside of cells, expression of type VII collagen in BM-MSCs was observed by immunostaining with an anti-type VII collagen antibody (Sigma Aldrich, St. Louis, MO, USA)

and western blotting of the culture supernatant. As shown in FIG. 5, the expression of type VII collagen was confirmed in the genetically modified MSCs.

3. Expression of Type VII Collagen in Epidermolysis Bullosa Model Mice

Figure 6:
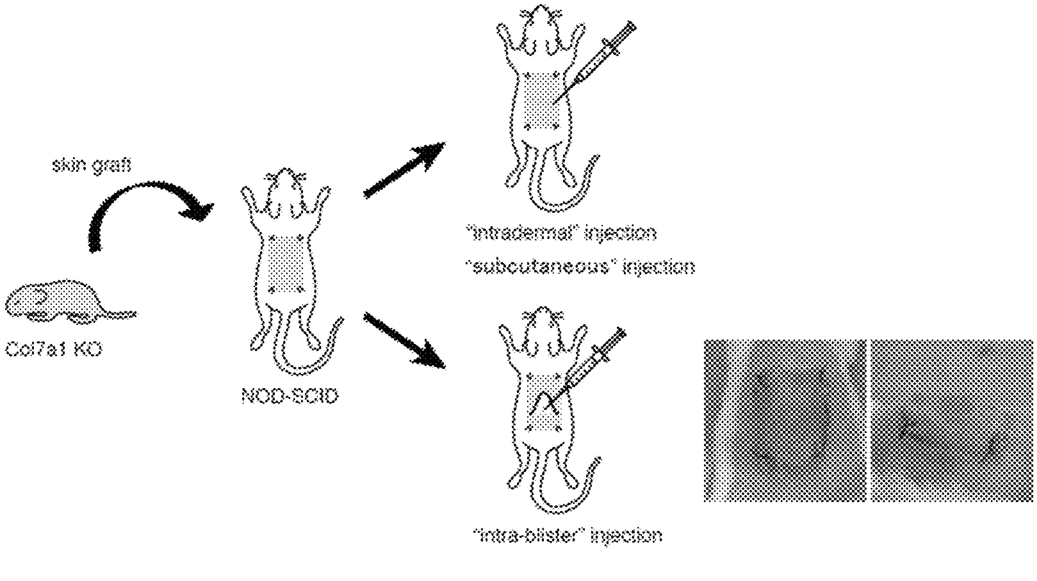
FIG. 6 is an explanatory diagram of the production of epidermolysis bullosa model mice. The photo on the right shows the formed blisters.

Expression of type VII collagen in epidermolysis bullosa model mice that received genetically modified MSCs was examined. The full-thickness skin of a neonatal Col7A1 gene knockout mouse (Col7a1−/−) showing blistering was excised and transplanted to the back of an immunodeficient mouse (NOD-SCID). One week after transplantation, the genetically modified MSCs described in section 2 above were injected subcutaneously or intradermally with 0.1 to $1.0\times10^6$ cells (FIG. 6). For intrablister injection, immediately after transplantation, the skin surface was pinched and rubbed to form blisters, and 0.1 to $1.0\times10^6$ cells of genetically modified MSCs were immediately injected into the space under the epidermis. Four weeks after each injection, the transplanted skin was excised, and the expression of type VII collagen was evaluated by immunostaining with an anti-type VII collagen antibody (Sigma Aldrich, St. Louis, MO, USA).

Figure 7:
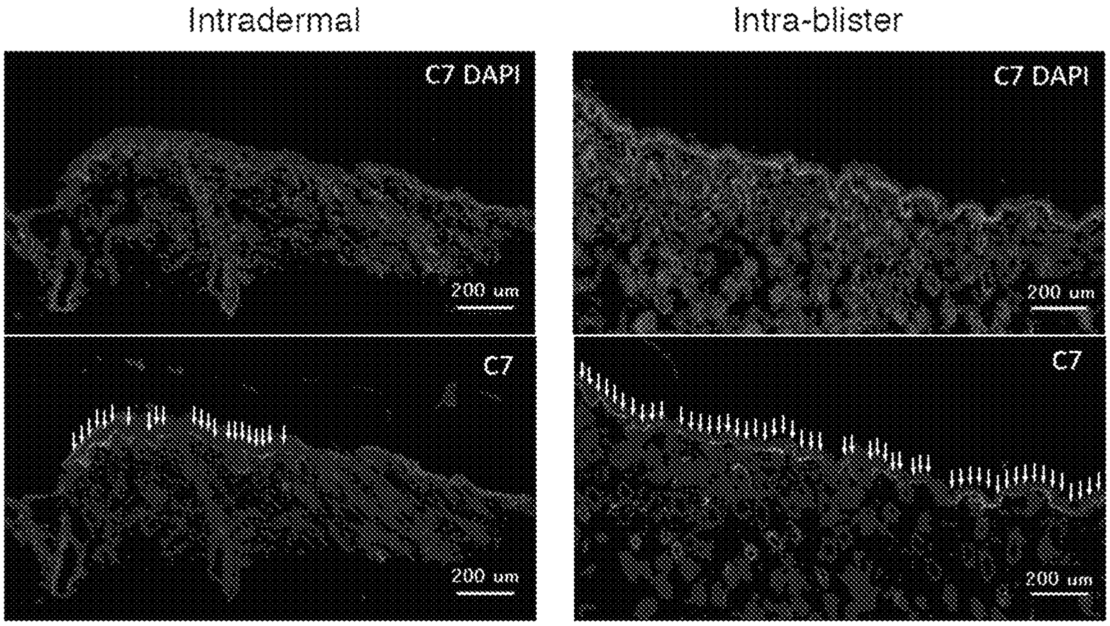
FIG. 7 shows a skin tomographic image of an epidermolysis bullosa model mouse to which genetically modified MSCs were injected by intradermal or intrablister injection. The upper photo shows a merged image of DAPI staining and immunostaining for type VII collagen, and the lower photo shows the results of immunostaining for type VII collagen. The arrows indicate the expression of type VII collagen.
Figure 8:
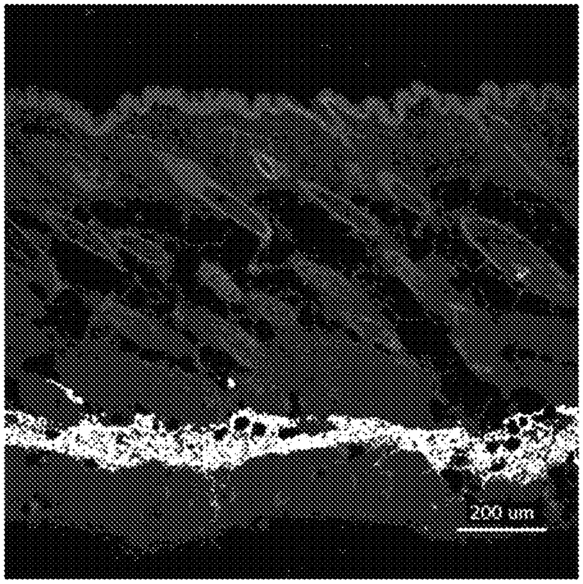
FIG. 8 shows a skin tomographic image of an epidermolysis bullosa model mouse to which genetically modified MSCs were injected by subcutaneous injection.

As shown in FIG. 7, the expression of type VII collagen was observed near the basement membrane in the intradermal injection and the intrablister injection, but the expression in the intradermal injection was partial. In the subcutaneous injection, collagen was expressed in a deep layer different from the basement membrane (FIG. 8). These results show that an excellent therapeutic effect is expected especially by intrablister injection.

Figure 9:
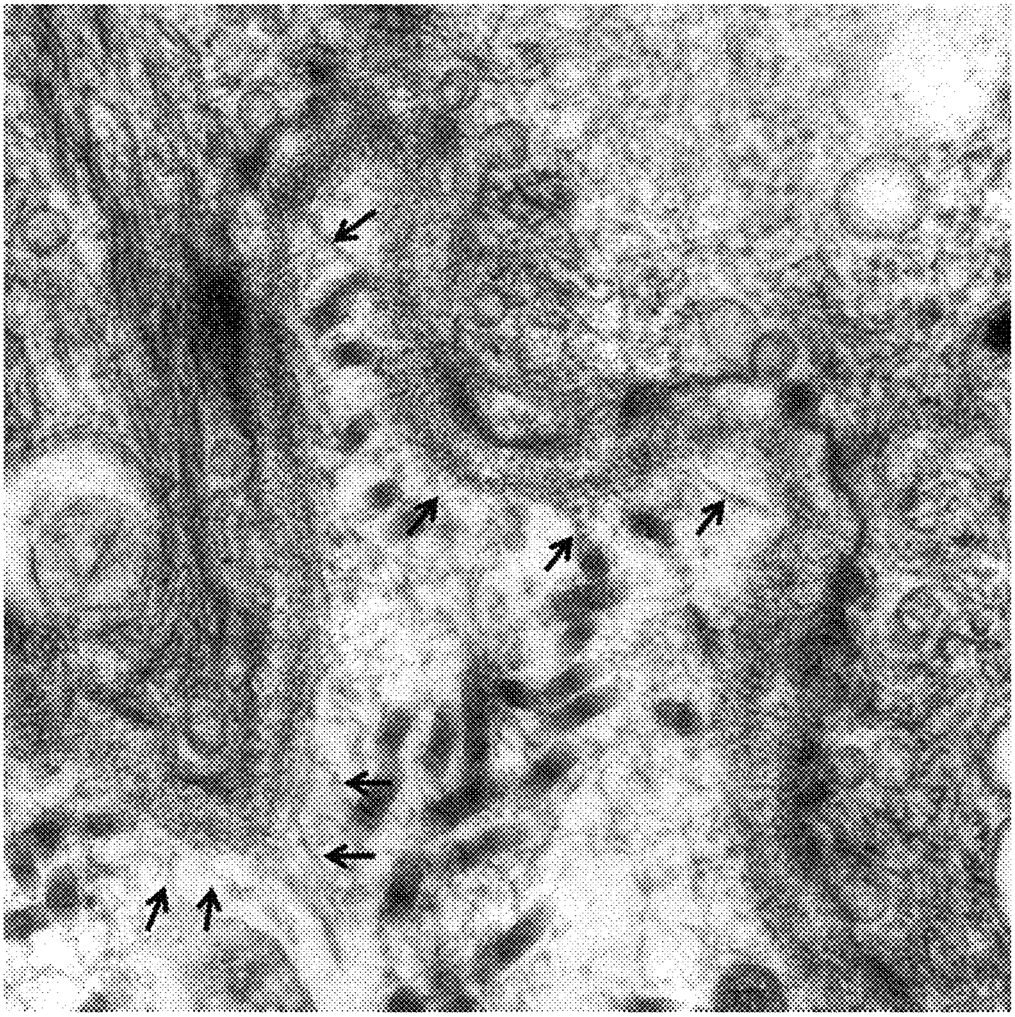
FIG. 9 shows an electron microscopic image of the skin of an epidermolysis bullosa model mouse to which genetically modified MSCs were injected by intrablister injection. The arrows indicate anchoring fibrils.

Further, in the same manner as above, $2.0\times10^6$ cells of the genetically modified MSCs described in section 2 above was injected into blisters. Four weeks after that, the transplanted skin was excised and observed with an electron microscope. Formation of anchoring fibrils was confirmed (FIG. 9).

The invention claimed is:

1. A method of treating dystrophic epidermolysis bullosa, comprising the steps of:

(a) obtaining mesenchymal stem cells from a patient with dystrophic epidermolysis bullosa;

(b) genetically modifying the cells to produce type VII collagen; and (c) administering the cells of (b) into a blister of the patient, wherein genetically modifying the cells of (b) includes delivering a COL7A1 gene to the cells.

2. The method of claim 1, wherein the COL7A1 gene comprises a nucleic acid sequence having 90% or more sequence identity with the nucleic acid sequence of SEQ ID NO: 1, or a nucleic acid sequence that encodes an amino acid sequence having 90% or more sequence identity with the amino acid sequence of SEQ ID NO: 2.

3. The method of claim 1, wherein the mesenchymal stem cells are bone marrow-derived mesenchymal stem cells.

4. The method of claim 1, wherein administering the cells to the patient comprises administering a population of cells to the patient, wherein the mesenchymal stem cells are the most abundant cells in the population.

5. The method of claim 1, wherein the cells are administered to the patient by intrablister injection, and wherein the intrablister injection is an injection of the cells into a space formed between the basement membrane and the dermis of the patient's skin, at a place where the basement membrane is detached from the dermis.

6. A method of treating dystrophic epidermolysis bullosa, comprising:

administering cells which produce type VII collagen to a patient in need thereof, the administering being intrablister administration.

7. The method of claim 6, wherein the cells have been genetically modified to produce type VII collagen, wherein the cells have been genetically modified by delivering a COL7A1 gene to the cells.

8. The method of claim 7, wherein the COL7A1 gene comprises a nucleic acid sequence having 90% or more sequence identity with the nucleic acid sequence of SEQ ID NO: 1, or a nucleic acid sequence that encodes an amino acid sequence having 90% or more sequence identity with the amino acid sequence of SEQ ID NO: 2.

9. The method of claim 6, wherein the cells have been obtained from the patient with dystrophic epidermolysis bullosa.

10. The method of claim 6, wherein the cells have been obtained from bone marrow.

11. The method of claim 6, wherein the cells are mesenchymal stem cells.

12. The method of claim 11, wherein the mesenchymal stem cells are bone marrow-derived mesenchymal stem cells.

13. The method of claim 11, wherein administering the cells to the patient comprises administering a population of cells to the patient, wherein the mesenchymal stem cells are the most abundant cells in the population.

14. The method of claim 6, wherein the intrablister administration is injection of the cells into a space formed between the basement membrane and the dermis of the patient's skin, at a place where the basement membrane is detached from the dermis.

15. A method of treating dystrophic epidermolysis bullosa, comprising:

administering cells which produce type VII collagen into a blister of a patient in need thereof, the cells being mesenchymal stem cells having been previously obtained from the patient and genetically modified to produce type VII collagen.

16. The method of claim 1, wherein the blister of the step (c) is a blister formed on the skin of the patient.

17. The method of claim 1, further comprising a step of artificially forming a blister on the skin of the patient before the step (c), wherein the cells of (b) are administered into the artificially formed blister in the step (c).

18. The method of claim 6, wherein the intrablister administration is administration into a blister formed on the skin of the patient.

19. The method of claim 6, wherein the cells are keratinocytes or skin fibroblasts.

* * * * *

SEQUENCE LISTING

```
<160> NUMBER OF SEQ ID NOS: 7

<210> SEQ ID NO 1
<211> LENGTH: 8835
<212> TYPE: DNA
<213> ORGANISM: Homo sapiens

<400> SEQUENCE: 1

atgacgctgc ggcttctggt ggccgcgctc tgcgccggga tcctggcaga ggcgccccga      60

gtgcgagccc agcacaggga gagagtgacc tgcacgcgcc tttacgccgc tgacattgtg     120

ttcttactgg atggctcctc atccattggc cgcagcaatt tccgcgaggt ccgcagcttt     180

ctcgaagggc tggtgctgcc tttctctgga gcagccagtg cacagggtgt gcgctttgcc     240

acagtgcagt acagcgatga tccacggaca gagttcggcc tggatgcact tggctctggg     300

ggtgatgtga tccgcgccat ccgtgagctt agctacaagg ggggcaacac tcgcacaggg     360

gctgcaattc tccatgtggc tgaccatgtc ttcctgcccc agctggcccg acctggtgtc     420

cccaaggtct gcatcctgat cacagacggg aagtcccagg acctggtgga cacagctgcc     480

caaaggctga aggggcaggg ggtcaagcta tttgctgtgg ggatcaagaa tgctgaccct     540

gaggagctga agcgagttgc ctcacagccc accagtgact tcttcttctt cgtcaatgac     600

ttcagcatct tgaggacact actgcccctc gtttcccgga gagtgtgcac gactgctggt     660

ggcgtgcctg tgacccgacc tccggatgac tcgacctctg ctccacgaga cctggtgctg     720

tctgagccaa gcagccaatc cttgagagta cagtggacag cggccagtgg ccctgtgact     780

ggctacaagg tccagtacac tcctctgacg gggctgggac agccactgcc gagtgagcgg     840

caggaggtga acgtcccagc tggtgagacc agtgtgcggc tgcggggtct ccggccactg     900

accgagtacc aagtgactgt gattgccctc tacgccaaca gcatcgggga ggctgtgagc     960

gggacagctc ggaccactgc cctagaaggg ccggaactga ccatccagaa taccacagcc    1020

cacagcctcc tggtggcctg gcggagtgtg ccaggtgcca ctggctaccg tgtgacatgg    1080

cgggtcctca gtggtgggcc cacacagcag caggagctgg gccctgggca gggttcagtg    1140

ttgctgcgtg acttggagcc tggcacggac tatgaggtga ccgtgagcac cctatttggc    1200

cgcagtgtgg ggcccgccac ttccctgatg gctcgcactg acgcttctgt tgagcagacc    1260

ctgcgcccgg tcatcctggg ccccacatcc atcctccttt cctggaactt ggtgcctgag    1320

gcccgtggct accggttgga atggcggcgt gagactggct tggagccacc gcagaaggtg    1380
```

-continued

```
gtactgccct ctgatgtgac ccgctaccag ttggatgggc tgcagccggg cactgagtac   1440
cgcctcacac tctacactct gctggagggc cacgaggtgg ccacccctgc aaccgtggtt   1500
cccactggac cagagctgcc tgtgagccct gtaacagacc tgcaagccac cgagctgccc   1560
gggcagcggg tgcgagtgtc ctggagccca gtccctggtg ccacccagta ccgcatcatt   1620
gtgcgcagca cccaggggt tgagcggacc ctggtgcttc ctgggagtca gacagcattc    1680
gacttggatg acgttcaggc tgggcttagc tacactgtgc gggtgtctgc tcgagtgggt   1740
ccccgtgagg gcagtgccag tgtcctcact gtccgccggg agccggaaac tccacttgct   1800
gttccagggc tgcgggttgt ggtgtcagat gcaacgcgag tgagggtggc ctggggaccc   1860
gtccctggag ccagtggatt tcggattagc tggagcacag gcagtggtcc ggagtccagc   1920
cagacactgc cccagactc tactgccaca gacatcacag ggctgcagcc tggaaccacc    1980
taccaggtgg ctgtgtcggt actgcgaggc agagaggagg gccctgctgc agtcatcgtg   2040
gctcgaacgg acccactggg cccagtgagg acggtccatg tgactcaggc cagcagctca   2100
tctgtcacca ttacctggac cagggttcct ggcgccacag gatacagggt ttcctggcac   2160
tcagcccacg gcccagagaa atcccagttg gtttctgggg aggccacggt ggctgagctg   2220
gatggactgg agccagatac tgagtatacg gtgcatgtga gggcccatgt ggctggcgtg   2280
gatgggcccc ctgcctctgt ggttgtgagg actgcccctg agcctgtggg tcgtgtgtcg   2340
aggctgcaga tcctcaatgc ttccagcgac gttctacgga tcacctgggt aggggtcact   2400
ggagccacag cttacagact ggcctggggc cggagtgaag gcggccccat gaggcaccag   2460
atactcccag gaaacacaga ctctgcagag atccggggtc tcgaaggtgg agtcagctac   2520
tcagtgcgag tgactgcact tgtcggggac cgcgagggca cacctgtctc cattgttgtc   2580
actacgccgc ctgaggctcc gccagccctg ggacgcttc acgtggtgca gcgcggggag    2640
cactcgctga ggctgcgctg ggagccggtg cccagagcgc agggcttcct tctgcactgg   2700
caacctgagg gtggccagga acagtcccgg gtcctggggc ccgagctcag cagctatcac   2760
ctggacgggc tggagccagc gacacagtac cgcgtgaggc tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgcccccgt ggcctggcgg atgtggtgtt cctaccacat   3180
gccactcaag acaatgctca ccgtgcggag gctacgagga gggtcctgga gcgtctggtg   3240
ttggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgccctacat ggacccaagt gggaacaacc tgggcacagc cgtggtcaca   3420
gctcacagat acatgttggc accagatgct cctgggcgcc gccagcacgt accaggggtg   3480
atggttctgc tagtggatga acccttgaga ggtgacatat tcagccccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
```

-continued

```
gagatgggcc tgagaggaca agttgggcct cctggcgacc ctggcctccc gggcaggacc   3840
ggtgctcccg gcccccaggg gcccccctgga agtgccactg ccaagggcga gaggggcttc   3900
cctggagcag atgggcgtcc aggcagccct ggccgcgccg ggaatcctgg gacccctgga   3960
gcccctggcc taaagggctc tccagggttg cctggccctc gtggggaccc gggagagcga   4020
ggacctcgag gcccaaaggg ggagccgggg gctcccggac aagtcatcgg aggtgaagga   4080
cctgggcttc ctgggcggaa aggggaccct ggaccatcgg gcccccctgg acctcgtgga   4140
ccactggggg acccaggacc ccgtggcccc ccagggcttc ctggaacagc catgaagggt   4200
gacaaaggcg atcgtgggga gcggggtccc cctggaccag gtgaaggtgg cattgctcct   4260
ggggagcctg ggctgccggg tcttcccgga agccctggac cccaaggccc cgttggcccc   4320
cctggaaaga aaggagaaaa aggtgactct gaggatggag ctccaggcct cccaggacaa   4380
cctgggtctc cgggtgagca gggcccacgg ggacctcctg gagctattgg ccccaaaggt   4440
gaccggggct ttccagggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgccctggg   4620
gaccctgcag tggtgggacc tgctgttgct ggacccaaag gagaaaaggg agatgtgggg   4680
cccgctgggc ccagaggagc taccggagtc caaggggaac ggggcccacc cggcttggtt   4740
cttcctggag accctggccc caagggagac cctggagacc ggggtcccat tggccttact   4800
ggcagagcag gacccccagg tgactcaggg cctcctggag agaagggaga ccctgggcgg   4860
cctggccccc caggacctgt tggcccccga ggacgagatg gtgaagttgg agagaaaggt   4920
gacgagggtc ctccgggtga cccgggtttg cctggaaaag caggcgagcg tggccttcgg   4980
ggggcacctg gagttcgggg gcctgtgggt gaaaagggag accagggaga tcctggagag   5040
gatggacgaa atggcagccc tggatcatct ggacccaagg gtgaccgtgg ggagccgggt   5100
cccccaggac ccccgggacg gctggtagac acaggacctg gagccagaga gaagggagag   5160
cctggggacc gcggacaaga gggtcctcga gggcccaagg gtgatcctgg cctccctgga   5220
gcccctgggg aaaggggcat tgaagggttt cggggacccc caggcccaca gggggaccca   5280
ggtgtccgag gcccagcagg agaaaagggt gaccggggtc cccctgggct ggatggccgg   5340
agcggactgg atgggaaacc aggagccgct gggccctctg ggccgaatgg tgctgcaggc   5400
aaagctgggg acccagggag agacgggctt ccaggcctcc gtggagaaca gggcctccct   5460
ggcccctctg gtccccctgg attaccggga aagccaggcg aggatggcaa acctggcctg   5520
aatggaaaaa acggagaacc tggggaccct ggagaagacg ggaggaaggg agagaaagga   5580
gattcaggcg cctctgggag agaaggtcgt gatggcccca agggtgagcg tggagctcct   5640
ggtatccttg gaccccaggg gcctccaggc ctcccagggc cagtgggccc tcctggccag   5700
ggttttcctg gtgtcccagg aggcacgggc cccaagggtg accgtgggga gactggatcc   5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacggcg tcgaggcccc   5940
aagggggact caggcgaaca gggcccccca ggcaaggagg gccccatcgg ctttcctgga   6000
gaacgcgggc tgaagggcga ccgtggagac cctggccctc aggggccacc tggtctggcc   6060
cttggggaga ggggcccccc cgggccttcc ggccttgccg gggagcctgg aaagcctggt   6120
```

-continued

```
attcccgggc tcccaggcag ggctgggggt gtgggagagg caggaaggcc aggagagagg   6180
ggagaacggg gagagaaagg agaacgtgga gaacagggca gagatggccc tcctggactc   6240
cctggaaccc ctgggccccc cggaccccct ggccccaagg tgtctgtgga tgagccaggt   6300
cctggactct ctggagaaca gggaccccct ggactcaagg gtgctaaggg ggagccgggc   6360
agcaatggtg accaaggtcc caaaggagac aggggtgtgc caggcatcaa aggagaccgg   6420
ggagagcctg gaccgagggg tcaggacggc aacccgggtc taccaggaga gcgtggtatg   6480
gctgggcctg aagggaagcc gggtctgcag ggtccaagag gcccccctgg cccagtgggt   6540
ggtcatggag accctggacc acctggtgcc ccgggtcttg ctggccctgc aggaccccaa   6600
ggaccttctg gcctgaaggg ggagcctgga gagacaggac ctccaggacg gggcctgact   6660
ggacctactg gagctgtggg acttcctgga ccccccggcc cttcaggcct tgtgggtcca   6720
caggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gccctgtcgg acctaaagga gaacctggcc ccacgggggc ccctggacag   6900
gctgtggtcg ggctccctgg agcaaaggga gagaagggag cccctggagg ccttgctgga   6960
gacctggtgg gtgagccggg agccaaaggt gaccgaggac tgccagggcc gcgaggcgag   7020
aagggtgaag ctggccgtgc aggggagccc ggagaccctg ggaagatggg tcagaaaggg   7080
gctccaggac ccaaaggttt caagggtgac ccaggagtcg ggtcccgggg ctcccctggg   7140
cctcctggcc ctccaggtgt gaagggagat ctgggcctcc ctggcctgcc cggtgctcct   7200
ggtgttgttg ggttcccggg tcagacaggc cctcgaggag agatgggtca gccaggccct   7260
agtggagagc ggggtctggc aggcccccca gggagagaag gaatcccagg acccctgggg   7320
ccacctggac caccggggtc agtgggacca cctggggcct ctggactcaa aggagacaag   7380
ggagaccctg gagtagggct gcctgggccc cgaggcgagc gtggggagcc aggcatccgg   7440
ggtgaagatg gccgccccgg ccaggaggga ccccgaggac tcacggggcc ccctggcagc   7500
aggggagagc gtggggagaa gggtgatgtt gggagtgcag gactaaaggg tgacaaggga   7560
gactcagctg tgatcctggg gcctccaggc ccacggggtg ccaaggggga catgggtgaa   7620
cgagggcctc ggggcttgga tggtgacaaa ggacctcggg gagacaatgg ggaccctggt   7680
gacaagggca gcaagggaga gcctggtgac aagggctcag ccgggttgcc aggactgcgt   7740
ggactcctgg gaccccaggg tcaacctggt gcagcaggga tccctggtga cccgggatcc   7800
ccaggaaagg atggagtgcc tggtatccga ggagaaaaag gagatgttgg cttcatgggt   7860
ccccggggcc tcaagggtga acggggagtg aagggagcct gtggccttga tggagagaag   7920
ggagacaagg gagaagctgg tcccccaggc cgccccgggc tggcaggaca caaaggagag   7980
atgggggagc ctggtgtgcc gggccagtcg ggggcccctg gcaaggaggg cctgatcggt   8040
cccaagggtg accgaggctt tgacgggcag ccaggcccca agggtgacca gggcgagaaa   8100
ggggagcggg gaaccccagg aattgggggc ttcccaggcc ccagtggaaa tgatggctct   8160
gctggtcccc cagggccacc tggcagtgtt ggtcccagag gccccgaagg acttcagggc   8220
cagaagggtg agcgaggtcc ccccggagag agagtggtgg gggctcctgg ggtccctgga   8280
gctcctggcg agagagggga gcaggggcgg ccagggcctg ccggtcctcg aggcgagaag   8340
ggagaagctg cactgacgga ggatgacatc cggggctttg tgcgccaaga gatgagtcag   8400
cactgtgcct gccagggcca gttcatcgca tctggatcac gacccctccc tagttatgct   8460
gcagacactg ccggctccca gctccatgct gtgcctgtgc tccgcgtctc tcatgcagag   8520
```

-continued gaggaagagc gggtaccccc tgaggatgat gagtactctg aatactccga gtattctgtg 8580
gaggagtacc aggaccctga agctccttgg gatagtgatg acccctgttc cctgccactg 8640
gatgagggct cctgcactgc ctacaccctg cgctggtacc atcgggctgt gacaggcagc 8700
acagaggcct gtcacccttt tgtctatggt ggctgtggag ggaatgccaa ccgttttggg 8760
acccgtgagg cctgcgagcg ccgctgccca ccccgggtgg tccagagcca ggggacaggt 8820
actgcccagg actga 8835

<210> SEQ ID NO 2
<211> LENGTH: 2944
<212> TYPE: PRT
<213> ORGANISM: Homo sapiens

<400> SEQUENCE: 2

Met Thr Leu Arg Leu Leu Val Ala Ala Leu Cys Ala Gly Ile Leu Ala
1 5 10 15

Glu Ala Pro Arg Val Arg Ala Gln His Arg Glu Arg Val Thr Cys Thr
20 25 30

Arg Leu Tyr Ala Ala Asp Ile Val Phe Leu Leu Asp Gly Ser Ser Ser
35 40 45

Ile Gly Arg Ser Asn Phe Arg Glu Val Arg Ser Phe Leu Glu Gly Leu
50 55 60

Val Leu Pro Phe Ser Gly Ala Ala Ser Ala Gln Gly Val Arg Phe Ala
65 70 75 80

Thr Val Gln Tyr Ser Asp Asp Pro Arg Thr Glu Phe Gly Leu Asp Ala
85 90 95

Leu Gly Ser Gly Gly Asp Val Ile Arg Ala Ile Arg Glu Leu Ser Tyr
100 105 110

Lys Gly Gly Asn Thr Arg Thr Gly Ala Ala Ile Leu His Val Ala Asp
115 120 125

His Val Phe Leu Pro Gln Leu Ala Arg Pro Gly Val Pro Lys Val Cys
130 135 140

Ile Leu Ile Thr Asp Gly Lys Ser Gln Asp Leu Val Asp Thr Ala Ala
145 150 155 160

Gln Arg Leu Lys Gly Gln Gly Val Lys Leu Phe Ala Val Gly Ile Lys
165 170 175

Asn Ala Asp Pro Glu Glu Leu Lys Arg Val Ala Ser Gln Pro Thr Ser
180 185 190

Asp Phe Phe Phe Phe Val Asn Asp Phe Ser Ile Leu Arg Thr Leu Leu
195 200 205

Pro Leu Val Ser Arg Arg Val Cys Thr Thr Ala Gly Gly Val Pro Val
210 215 220

Thr Arg Pro Pro Asp Asp Ser Thr Ser Ala Pro Arg Asp Leu Val Leu
225 230 235 240

Ser Glu Pro Ser Ser Gln Ser Leu Arg Val Gln Trp Thr Ala Ala Ser
245 250 255

Gly Pro Val Thr Gly Tyr Lys Val Gln Tyr Thr Pro Leu Thr Gly Leu
260 265 270

Gly Gln Pro Leu Pro Ser Glu Arg Gln Glu Val Asn Val Pro Ala Gly
275 280 285

Glu Thr Ser Val Arg Leu Arg Gly Leu Arg Pro Leu Thr Glu Tyr Gln
290 295 300

Val Thr Val Ile Ala Leu Tyr Ala Asn Ser Ile Gly Glu Ala Val Ser

-continued

```
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
    370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
    450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
        515                 520                 525

Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575

Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
        595                 600                 605

Ser Asp Ala Thr Arg Val Arg Val Ala Trp Gly Pro Val Pro Gly Ala
    610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735
```

-continued

```
Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro  Gly Ser Pro Gln Thr  Leu Pro Gly
        995                 1000                 1005

Ile Ser  Ser Ser Gln Arg Val  Thr Gly Leu Glu Pro  Gly Val Ser
    1010                 1015                 1020

Tyr Ile  Phe Ser Leu Thr Pro  Val Leu Asp Gly Val  Arg Gly Pro
    1025                 1030                 1035

Glu Ala  Ser Val Thr Gln Thr  Pro Val Cys Pro Arg  Gly Leu Ala
    1040                 1045                 1050

Asp Val  Val Phe Leu Pro His  Ala Thr Gln Asp Asn  Ala His Arg
    1055                 1060                 1065

Ala Glu  Ala Thr Arg Arg Val  Leu Glu Arg Leu Val  Leu Ala Leu
    1070                 1075                 1080

Gly Pro  Leu Gly Pro Gln Ala  Val Gln Val Gly Leu  Leu Ser Tyr
    1085                 1090                 1095

Ser His  Arg Pro Ser Pro Leu  Phe Pro Leu Asn Gly  Ser His Asp
    1100                 1105                 1110

Leu Gly  Ile Ile Leu Gln Arg  Ile Arg Asp Met Pro  Tyr Met Asp
    1115                 1120                 1125

Pro Ser  Gly Asn Asn Leu Gly  Thr Ala Val Val Thr  Ala His Arg
    1130                 1135                 1140
```

-continued

```
Tyr Met  Leu Ala Pro Asp Ala  Pro Gly Arg Arg Gln  His Val Pro
    1145                 1150                 1155

Gly Val  Met Val Leu Leu Val  Asp Glu Pro Leu Arg  Gly Asp Ile
    1160                 1165                 1170

Phe Ser  Pro Ile Arg Glu Ala  Gln Ala Ser Gly Leu  Asn Val Val
    1175                 1180                 1185

Met Leu  Gly Met Ala Gly Ala  Asp Pro Glu Gln Leu  Arg Arg Leu
    1190                 1195                 1200

Ala Pro  Gly Met Asp Ser Val  Gln Thr Phe Phe Ala  Val Asp Asp
    1205                 1210                 1215

Gly Pro  Ser Leu Asp Gln Ala  Val Ser Gly Leu Ala  Thr Ala Leu
    1220                 1225                 1230

Cys Gln  Ala Ser Phe Thr Thr  Gln Pro Arg Pro Glu  Pro Cys Pro
    1235                 1240                 1245

Val Tyr  Cys Pro Lys Gly Gln  Lys Gly Glu Pro Gly  Glu Met Gly
    1250                 1255                 1260

Leu Arg  Gly Gln Val Gly Pro  Pro Gly Asp Pro Gly  Leu Pro Gly
    1265                 1270                 1275

Arg Thr  Gly Ala Pro Gly Pro  Gln Gly Pro Pro Gly  Ser Ala Thr
    1280                 1285                 1290

Ala Lys  Gly Glu Arg Gly Phe  Pro Gly Ala Asp Gly  Arg Pro Gly
    1295                 1300                 1305

Ser Pro  Gly Arg Ala Gly Asn  Pro Gly Thr Pro Gly  Ala Pro Gly
    1310                 1315                 1320

Leu Lys  Gly Ser Pro Gly Leu  Pro Gly Pro Arg Gly  Asp Pro Gly
    1325                 1330                 1335

Glu Arg  Gly Pro Arg Gly Pro  Lys Gly Glu Pro Gly  Ala Pro Gly
    1340                 1345                 1350

Gln Val  Ile Gly Gly Glu Gly  Pro Gly Leu Pro Gly  Arg Lys Gly
    1355                 1360                 1365

Asp Pro  Gly Pro Ser Gly Pro  Pro Gly Pro Arg Gly  Pro Leu Gly
    1370                 1375                 1380

Asp Pro  Gly Pro Arg Gly Pro  Pro Gly Leu Pro Gly  Thr Ala Met
    1385                 1390                 1395

Lys Gly  Asp Lys Gly Asp Arg  Gly Glu Arg Gly Pro  Pro Gly Pro
    1400                 1405                 1410

Gly Glu  Gly Gly Ile Ala Pro  Gly Glu Pro Gly Leu  Pro Gly Leu
    1415                 1420                 1425

Pro Gly  Ser Pro Gly Pro Gln  Gly Pro Val Gly Pro  Pro Gly Lys
    1430                 1435                 1440

Lys Gly  Glu Lys Gly Asp Ser  Glu Asp Gly Ala Pro  Gly Leu Pro
    1445                 1450                 1455

Gly Gln  Pro Gly Ser Pro Gly  Glu Gln Gly Pro Arg  Gly Pro Pro
    1460                 1465                 1470

Gly Ala  Ile Gly Pro Lys Gly  Asp Arg Gly Phe Pro  Gly Pro Leu
    1475                 1480                 1485

Gly Glu  Ala Gly Glu Lys Gly  Glu Arg Gly Pro Pro  Gly Pro Ala
    1490                 1495                 1500

Gly Ser  Arg Gly Leu Pro Gly  Val Ala Gly Arg Pro  Gly Ala Lys
    1505                 1510                 1515

Gly Pro  Glu Gly Pro Pro Gly  Pro Thr Gly Arg Gln  Gly Glu Lys
    1520                 1525                 1530

Gly Glu  Pro Gly Arg Pro Gly  Asp Pro Ala Val Val  Gly Pro Ala
```

```
    1535                1540                1545

Val Ala  Gly Pro Lys Gly Glu  Lys Gly Asp Val Gly  Pro Ala Gly
    1550                1555                1560

Pro Arg  Gly Ala Thr Gly Val  Gln Gly Glu Arg Gly  Pro Pro Gly
    1565                1570                1575

Leu Val  Leu Pro Gly Asp Pro  Gly Pro Lys Gly Asp  Pro Gly Asp
    1580                1585                1590

Arg Gly  Pro Ile Gly Leu Thr  Gly Arg Ala Gly Pro  Pro Gly Asp
    1595                1600                1605

Ser Gly  Pro Pro Gly Glu Lys  Gly Asp Pro Gly Arg  Pro Gly Pro
    1610                1615                1620

Pro Gly  Pro Val Gly Pro Arg  Gly Arg Asp Gly Glu  Val Gly Glu
    1625                1630                1635

Lys Gly  Asp Glu Gly Pro Pro  Gly Asp Pro Gly Leu  Pro Gly Lys
    1640                1645                1650

Ala Gly  Glu Arg Gly Leu Arg  Gly Ala Pro Gly Val  Arg Gly Pro
    1655                1660                1665

Val Gly  Glu Lys Gly Asp Gln  Gly Asp Pro Gly Glu  Asp Gly Arg
    1670                1675                1680

Asn Gly  Ser Pro Gly Ser Ser  Gly Pro Lys Gly Asp  Arg Gly Glu
    1685                1690                1695

Pro Gly  Pro Pro Gly Pro Pro  Gly Arg Leu Val Asp  Thr Gly Pro
    1700                1705                1710

Gly Ala  Arg Glu Lys Gly Glu  Pro Gly Asp Arg Gly  Gln Glu Gly
    1715                1720                1725

Pro Arg  Gly Pro Lys Gly Asp  Pro Gly Leu Pro Gly  Ala Pro Gly
    1730                1735                1740

Glu Arg  Gly Ile Glu Gly Phe  Arg Gly Pro Pro Gly  Pro Gln Gly
    1745                1750                1755

Asp Pro  Gly Val Arg Gly Pro  Ala Gly Glu Lys Gly  Asp Arg Gly
    1760                1765                1770

Pro Pro  Gly Leu Asp Gly Arg  Ser Gly Leu Asp Gly  Lys Pro Gly
    1775                1780                1785

Ala Ala  Gly Pro Ser Gly Pro  Asn Gly Ala Ala Gly  Lys Ala Gly
    1790                1795                1800

Asp Pro  Gly Arg Asp Gly Leu  Pro Gly Leu Arg Gly  Glu Gln Gly
    1805                1810                1815

Leu Pro  Gly Pro Ser Gly Pro  Pro Gly Leu Pro Gly  Lys Pro Gly
    1820                1825                1830

Glu Asp  Gly Lys Pro Gly Leu  Asn Gly Lys Asn Gly  Glu Pro Gly
    1835                1840                1845

Asp Pro  Gly Glu Asp Gly Arg  Lys Gly Glu Lys Gly  Asp Ser Gly
    1850                1855                1860

Ala Ser  Gly Arg Glu Gly Arg  Asp Gly Pro Lys Gly  Glu Arg Gly
    1865                1870                1875

Ala Pro  Gly Ile Leu Gly Pro  Gln Gly Pro Pro Gly  Leu Pro Gly
    1880                1885                1890

Pro Val  Gly Pro Pro Gly Gln  Gly Phe Pro Gly Val  Pro Gly Gly
    1895                1900                1905

Thr Gly  Pro Lys Gly Asp Arg  Gly Glu Thr Gly Ser  Lys Gly Glu
    1910                1915                1920

Gln Gly  Leu Pro Gly Glu Arg  Gly Leu Arg Gly Glu  Pro Gly Ser
    1925                1930                1935
```

-continued

```
Val Pro Asn Val Asp Arg Leu Leu Glu Thr Ala Gly Ile Lys Ala
    1940                1945                1950

Ser Ala Leu Arg Glu Ile Val Glu Thr Trp Asp Glu Ser Ser Gly
    1955                1960                1965

Ser Phe Leu Pro Val Pro Glu Arg Arg Arg Gly Pro Lys Gly Asp
    1970                1975                1980

Ser Gly Glu Gln Gly Pro Pro Gly Lys Glu Gly Pro Ile Gly Phe
    1985                1990                1995

Pro Gly Glu Arg Gly Leu Lys Gly Asp Arg Gly Asp Pro Gly Pro
    2000                2005                2010

Gln Gly Pro Pro Gly Leu Ala Leu Gly Glu Arg Gly Pro Pro Gly
    2015                2020                2025

Pro Ser Gly Leu Ala Gly Glu Pro Gly Lys Pro Gly Ile Pro Gly
    2030                2035                2040

Leu Pro Gly Arg Ala Gly Gly Val Gly Glu Ala Gly Arg Pro Gly
    2045                2050                2055

Glu Arg Gly Glu Arg Gly Glu Lys Gly Glu Arg Gly Glu Gln Gly
    2060                2065                2070

Arg Asp Gly Pro Pro Gly Leu Pro Gly Thr Pro Gly Pro Pro Gly
    2075                2080                2085

Pro Pro Gly Pro Lys Val Ser Val Asp Glu Pro Gly Pro Gly Leu
    2090                2095                2100

Ser Gly Glu Gln Gly Pro Pro Gly Leu Lys Gly Ala Lys Gly Glu
    2105                2110                2115

Pro Gly Ser Asn Gly Asp Gln Gly Pro Lys Gly Asp Arg Gly Val
    2120                2125                2130

Pro Gly Ile Lys Gly Asp Arg Gly Glu Pro Gly Pro Arg Gly Gln
    2135                2140                2145

Asp Gly Asn Pro Gly Leu Pro Gly Glu Arg Gly Met Ala Gly Pro
    2150                2155                2160

Glu Gly Lys Pro Gly Leu Gln Gly Pro Arg Gly Pro Pro Gly Pro
    2165                2170                2175

Val Gly Gly His Gly Asp Pro Gly Pro Pro Gly Ala Pro Gly Leu
    2180                2185                2190

Ala Gly Pro Ala Gly Pro Gln Gly Pro Ser Gly Leu Lys Gly Glu
    2195                2200                2205

Pro Gly Glu Thr Gly Pro Pro Gly Arg Gly Leu Thr Gly Pro Thr
    2210                2215                2220

Gly Ala Val Gly Leu Pro Gly Pro Pro Gly Pro Ser Gly Leu Val
    2225                2230                2235

Gly Pro Gln Gly Ser Pro Gly Leu Pro Gly Gln Val Gly Glu Thr
    2240                2245                2250

Gly Lys Pro Gly Ala Pro Gly Arg Asp Gly Ala Ser Gly Lys Asp
    2255                2260                2265

Gly Asp Arg Gly Ser Pro Gly Val Pro Gly Ser Pro Gly Leu Pro
    2270                2275                2280

Gly Pro Val Gly Pro Lys Gly Glu Pro Gly Pro Thr Gly Ala Pro
    2285                2290                2295

Gly Gln Ala Val Val Gly Leu Pro Gly Ala Lys Gly Glu Lys Gly
    2300                2305                2310

Ala Pro Gly Gly Leu Ala Gly Asp Leu Val Gly Glu Pro Gly Ala
    2315                2320                2325
```

```
Lys Gly Asp Arg Gly Leu Pro Gly Pro Arg Gly Glu Lys Gly Glu
    2330                2335                2340

Ala Gly Arg Ala Gly Glu Pro Gly Asp Pro Gly Glu Asp Gly Gln
    2345                2350                2355

Lys Gly Ala Pro Gly Pro Lys Gly Phe Lys Gly Asp Pro Gly Val
    2360                2365                2370

Gly Val Pro Gly Ser Pro Gly Pro Pro Gly Pro Pro Gly Val Lys
    2375                2380                2385

Gly Asp Leu Gly Leu Pro Gly Leu Pro Gly Ala Pro Gly Val Val
    2390                2395                2400

Gly Phe Pro Gly Gln Thr Gly Pro Arg Gly Glu Met Gly Gln Pro
    2405                2410                2415

Gly Pro Ser Gly Glu Arg Gly Leu Ala Gly Pro Pro Gly Arg Glu
    2420                2425                2430

Gly Ile Pro Gly Pro Leu Gly Pro Pro Gly Pro Pro Gly Ser Val
    2435                2440                2445

Gly Pro Pro Gly Ala Ser Gly Leu Lys Gly Asp Lys Gly Asp Pro
    2450                2455                2460

Gly Val Gly Leu Pro Gly Pro Arg Gly Glu Arg Gly Glu Pro Gly
    2465                2470                2475

Ile Arg Gly Glu Asp Gly Arg Pro Gly Gln Glu Gly Pro Arg Gly
    2480                2485                2490

Leu Thr Gly Pro Pro Gly Ser Arg Gly Glu Arg Gly Glu Lys Gly
    2495                2500                2505

Asp Val Gly Ser Ala Gly Leu Lys Gly Asp Lys Gly Asp Ser Ala
    2510                2515                2520

Val Ile Leu Gly Pro Pro Gly Pro Arg Gly Ala Lys Gly Asp Met
    2525                2530                2535

Gly Glu Arg Gly Pro Arg Gly Leu Asp Gly Asp Lys Gly Pro Arg
    2540                2545                2550

Gly Asp Asn Gly Asp Pro Gly Asp Lys Gly Ser Lys Gly Glu Pro
    2555                2560                2565

Gly Asp Lys Gly Ser Ala Gly Leu Pro Gly Leu Arg Gly Leu Leu
    2570                2575                2580

Gly Pro Gln Gly Gln Pro Gly Ala Ala Gly Ile Pro Gly Asp Pro
    2585                2590                2595

Gly Ser Pro Gly Lys Asp Gly Val Pro Gly Ile Arg Gly Glu Lys
    2600                2605                2610

Gly Asp Val Gly Phe Met Gly Pro Arg Gly Leu Lys Gly Glu Arg
    2615                2620                2625

Gly Val Lys Gly Ala Cys Gly Leu Asp Gly Glu Lys Gly Asp Lys
    2630                2635                2640

Gly Glu Ala Gly Pro Pro Gly Arg Pro Gly Leu Ala Gly His Lys
    2645                2650                2655

Gly Glu Met Gly Glu Pro Gly Val Pro Gly Gln Ser Gly Ala Pro
    2660                2665                2670

Gly Lys Glu Gly Leu Ile Gly Pro Lys Gly Asp Arg Gly Phe Asp
    2675                2680                2685

Gly Gln Pro Gly Pro Lys Gly Asp Gln Gly Glu Lys Gly Glu Arg
    2690                2695                2700

Gly Thr Pro Gly Ile Gly Gly Phe Pro Gly Pro Ser Gly Asn Asp
    2705                2710                2715

Gly Ser Ala Gly Pro Pro Gly Pro Pro Gly Ser Val Gly Pro Arg
```

```
    2720                2725                2730

Gly Pro  Glu Gly Leu Gln Gly  Gln Lys Gly Glu Arg  Gly Pro Pro
    2735                2740                2745

Gly Glu  Arg Val Val Gly Ala  Pro Gly Val Pro Gly  Ala Pro Gly
    2750                2755                2760

Glu Arg  Gly Glu Gln Gly Arg  Pro Gly Pro Ala Gly  Pro Arg Gly
    2765                2770                2775

Glu Lys  Gly Glu Ala Ala Leu  Thr Glu Asp Asp Ile  Arg Gly Phe
    2780                2785                2790

Val Arg  Gln Glu Met Ser Gln  His Cys Ala Cys Gln  Gly Gln Phe
    2795                2800                2805

Ile Ala  Ser Gly Ser Arg Pro  Leu Pro Ser Tyr Ala  Ala Asp Thr
    2810                2815                2820

Ala Gly  Ser Gln Leu His Ala  Val Pro Val Leu Arg  Val Ser His
    2825                2830                2835

Ala Glu  Glu Glu Glu Arg Val  Pro Pro Glu Asp Asp  Glu Tyr Ser
    2840                2845                2850

Glu Tyr  Ser Glu Tyr Ser Val  Glu Glu Tyr Gln Asp  Pro Glu Ala
    2855                2860                2865

Pro Trp  Asp Ser Asp Asp Pro  Cys Ser Leu Pro Leu  Asp Glu Gly
    2870                2875                2880

Ser Cys  Thr Ala Tyr Thr Leu  Arg Trp Tyr His Arg  Ala Val Thr
    2885                2890                2895

Gly Ser  Thr Glu Ala Cys His  Pro Phe Val Tyr Gly  Gly Cys Gly
    2900                2905                2910

Gly Asn  Ala Asn Arg Phe Gly  Thr Arg Glu Ala Cys  Glu Arg Arg
    2915                2920                2925

Cys Pro  Pro Arg Val Val Gln  Ser Gln Gly Thr Gly  Thr Ala Gln
    2930                2935                2940

Asp


<210> SEQ ID NO 3
<211> LENGTH: 20
<212> TYPE: DNA
<213> ORGANISM: Homo sapiens

<400> SEQUENCE: 3

accccacagt ggggccacta                                              20


<210> SEQ ID NO 4
<211> LENGTH: 20
<212> TYPE: DNA
<213> ORGANISM: Homo sapiens

<400> SEQUENCE: 4

gtcaccaatc ctgtccctag                                              20


<210> SEQ ID NO 5
<211> LENGTH: 20
<212> TYPE: DNA
<213> ORGANISM: Homo sapiens

<400> SEQUENCE: 5

ggggccacta gggacaggat                                              20


<210> SEQ ID NO 6
<211> LENGTH: 60
```

-continued

```
<212> TYPE: DNA
<213> ORGANISM: Homo sapiens

<400> SEQUENCE: 6

ctgtcccctc caccccacag tggggccact agggacagga ttggtgacag aaaagcccca     60


<210> SEQ ID NO 7
<211> LENGTH: 60
<212> TYPE: DNA
<213> ORGANISM: Homo sapiens

<400> SEQUENCE: 7

tggggctttt ctgtcaccaa tcctgtccct agtggcccca ctgtggggtg gaggggacag     60
```